US009492561B2

(12) United States Patent
Chang et al.

(10) Patent No.: US 9,492,561 B2
(45) Date of Patent: *Nov. 15, 2016

(54) DOCK-AND-LOCK (DNL) COMPLEXES FOR DELIVERY OF INTERFERENCE RNA

(71) Applicant: IBC Pharmaceuticals, Inc., Morris Plains, NJ (US)

(72) Inventors: Chien-Hsing Chang, Downingtown, PA (US); David M. Goldenberg, Mendham, NJ (US)

(73) Assignee: IBC Pharmaceuticals, Inc., Morris Plains, NJ (US)

( * ) Notice: Subject to any disclaimer, the term of this patent is extended or adjusted under 35 U.S.C. 154(b) by 75 days.

This patent is subject to a terminal disclaimer.

(21) Appl. No.: 13/908,914

(22) Filed: Jun. 3, 2013

(65) Prior Publication Data

US 2013/0289244 A1 Oct. 31, 2013

Related U.S. Application Data

(60) Continuation of application No. 12/964,021, filed on Dec. 9, 2010, now Pat. No. 8,491,914, which is a continuation-in-part of application No. 12/949,536, filed on Nov. 18, 2010, now Pat. No. 8,211,440, (Continued)

(51) Int. Cl.
*A61K 47/48* (2006.01)
*C07K 16/28* (2006.01)
*C07K 16/30* (2006.01)
*C07K 16/00* (2006.01)
*B82Y 5/00* (2011.01)
*C07K 16/46* (2006.01)

(52) U.S. Cl.
CPC ....... *A61K 47/484* (2013.01); *A61K 47/48561* (2013.01); *A61K 47/48576* (2013.01); *A61K 47/48723* (2013.01); *B82Y 5/00* (2013.01); *C07K 16/2803* (2013.01); *C07K 16/2887* (2013.01); *C07K 16/3007* (2013.01); *C07K 16/468* (2013.01); *C07K 2317/31* (2013.01); *C07K 2317/55* (2013.01); *C07K 2317/77* (2013.01); *C07K 2317/92* (2013.01); *C07K 2318/10* (2013.01); *C07K 2319/00* (2013.01); *C07K 2319/30* (2013.01)

(58) Field of Classification Search
CPC ..................... A61K 47/484; A61K 47/48561; A61K 47/48723; B82Y 5/00; C07K 16/2803; C07K 16/2887; C07K 16/3007; C07K 16/48576; C07K 16/468; C07K 2317/31; C07K 2317/54; C07K 2317/55; C07K 2317/622; C07K 2317/77; C07K 2317/92; C07K 2316/52; C07K 2319/00; C07K 2319/30; C07K 2319/73
See application file for complete search history.

(56) References Cited

U.S. PATENT DOCUMENTS

| 4,046,722 | A | 9/1977 | Rowland |
| 4,699,784 | A | 10/1987 | Shih et al. |
| 4,868,109 | A | 9/1989 | Lansdorp et al. |
| 5,196,193 | A | 3/1993 | Carroll |
| 5,770,198 | A | 6/1998 | Coller et al. |
| 5,871,945 | A | 2/1999 | Lockerbie et al. |
| 6,261,537 | B1 | 7/2001 | Klaveness |
| 6,306,393 | B1 | 10/2001 | Goldenberg et al. |
| 6,416,958 | B2 | 7/2002 | Vidovic et al. |
| 6,524,854 | B1 | 2/2003 | Mania et al. |
| 6,617,135 | B1 | 9/2003 | Gillies et al. |
| 6,894,149 | B2 | 5/2005 | Tso et al. |
| 7,060,506 | B2 | 6/2006 | Craig |
| 7,151,164 | B2 | 12/2006 | Hansen et al. |
| 7,262,278 | B2 | 8/2007 | Tawara et al. |
| 7,432,342 | B2 | 10/2008 | Braun et al. |
| 7,521,056 | B2 | 4/2009 | Chang et al. |
| 7,527,787 | B2 | 5/2009 | Chang et al. |
| 7,534,866 | B2 | 5/2009 | Chang et al. |
| 7,534,878 | B2 * | 5/2009 | Liu et al. ............. 536/24.5 |
| 7,541,440 | B2 | 6/2009 | Goldenberg et al. |
| 7,550,143 | B2 | 6/2009 | Chang et al. |
| 7,591,994 | B2 | 9/2009 | Govindan et al. |
| 7,858,070 | B2 | 12/2010 | Chang et al. |

(Continued)

FOREIGN PATENT DOCUMENTS

| WO | WO0068248 | 11/2000 |
| WO | WO2005/076999 | * 8/2005 |

(Continued)

OTHER PUBLICATIONS

Colman et al., Research in Immunology (145(1):33-35, 1994.*

(Continued)

*Primary Examiner* — Phuong Huynh

(74) *Attorney, Agent, or Firm* — Richard A. Nakashima

(57) ABSTRACT

Described herein are compositions and methods of use of targeted delivery complexes for delivery of siRNA to a disease-associated cell, tissue or pathogen. The targeted delivery complex comprises a targeting molecule, such as an antibody or fragment thereof, conjugated to one or more siRNA carriers. In preferred embodiments the siRNA carrier is a dendrimer or protamine and the targeting molecule is an anti-cancer antibody, such as hRS7. More preferably, the antibody or fragment is rapidly internalized into the target cell to facilitate uptake of the siRNA. Most preferably, the targeted delivery complex is made by the DNL technique. The compositions and methods are of use to treat a variety of disease states, such as cancer, autoimmune disease, immune dysfunction, cardiac disease, neurologic disease, inflammatory disease or infectious disease.

4 Claims, 4 Drawing Sheets

Related U.S. Application Data which is a division of application No. 12/396,605, filed on Mar. 3, 2009, now Pat. No. 7,858,070, which is a division of application No. 11/633,729, filed on Dec. 5, 2006, now Pat. No. 7,527,787, which is a continuation-in-part of application No. 11/389,358, filed on Mar. 24, 2006, now Pat. No. 7,550,143, and a continuation-in-part of application No. 11/391,584, filed on Mar. 28, 2006, now Pat. No. 7,521,056, and a continuation-in-part of application No. 11/478,021, filed on Jun. 29, 2006, now Pat. No. 7,534,866, said application No. 12/964,021 is a continuation-in-part of application No. 12/915,515, filed on Oct. 29, 2010, now abandoned, and a continuation-in-part of application No. 12/871,345, filed on Aug. 30, 2010, now Pat. No. 8,551,480, which is a continuation-in-part of application No. 12/754,740, filed on Apr. 6, 2010, now Pat. No. 8,562,988, and a continuation-in-part of application No. 12/754,140, filed on Apr. 5, 2010, now Pat. No. 8,722,047, and a continuation-in-part of application No. 12/752,649, filed on Apr. 1, 2010, now Pat. No. 8,034,352, and a continuation-in-part of application No. 12/731,781, filed on Mar. 25, 2010, now Pat. No. 8,003,111, and a continuation-in-part of application No. 12/644,146, filed on Dec. 22, 2009, now Pat. No. 7,981,398, and a continuation-in-part of application No. 12/544,476, filed on Aug. 20, 2009, now Pat. No. 7,901,680, and a continuation-in-part of application No. 12/537,803, filed on Aug. 7, 2009, now Pat. No. 8,491,896, and a continuation-in-part of application No. 12/479,250, filed on Jun. 5, 2009, now Pat. No. 8,192,739, which is a continuation of application No. 11/056,182, filed on Feb. 14, 2005, now Pat. No. 7,544,487, said application No. 12/871,345 is a continuation-in-part of application No. 12/468,589, filed on May 19, 2009, now Pat. No. 8,163,291, and a continuation-in-part of application No. 12/418,877, filed on Apr. 6, 2009, now Pat. No. 7,906,118, and a continuation-in-part of application No. 12/417,917, filed on Apr. 3, 2009, now Pat. No. 7,906,121, and a continuation-in-part of application No. 12/396,965, filed on Mar. 3, 2009, now Pat. No. 7,871,622, and a continuation-in-part of application No. 12/396,605, filed on Mar. 3, 2009, now Pat. No. 7,858,070, said application No. 12/964,021 is a continuation-in-part of application No. 12/869,823, filed on Aug. 27, 2010, and a continuation-in-part of application No. 12/754,740, filed on Apr. 6, 2010, now Pat. No. 8,562,988, and a continuation-in-part of application No. 12/752,649, filed on Apr. 1, 2010, now Pat. No. 8,034,352, and a continuation-in-part of application No. 12/731,781, filed on Mar. 25, 2010, now Pat. No. 8,003,111, and a continuation-in-part of application No. 12/644,146, filed on Dec. 22, 2009, now Pat. No. 7,981,398, which is a division of application No. 11/925,408, filed on Oct. 26, 2007, now Pat. No. 7,666,400, which is a continuation-in-part of application No. 11/391,584, filed on Mar. 28, 2006, now Pat. No. 7,521,056, said application No. 12/964,021 is a continuation-in-part of application No. 12/544,476, filed on Aug. 20, 2009, now Pat. No. 7,901,680, and a continuation-in-part of application No. 12/468,589, filed on May 19, 2009, now Pat. No. 8,163,291, which is a division of application No. 11/389,358, filed on Mar. 24, 2006, now Pat. No. 7,550,143, said application No. 12/964,021 is a continuation-in-part of application No. 12/418,877, filed on Apr. 6, 2009, now Pat. No. 7,906,118, and a continuation-in-part of application No. 12/417,917, filed on Apr. 3, 2009, now Pat. No. 7,906,121, which is a division of application No. 11/478,021, filed on Jun. 29, 2006, now Pat. No. 7,534,866, said application No. 12/964,021 is a continuation-in-part of application No. 12/396,965, filed on Mar. 3, 2009, now Pat. No. 7,871,622, which is a division of application No. 11/391,584, filed on Mar. 28, 2006, now Pat. No. 7,521,056.

(60) Provisional application No. 60/782,332, filed on Mar. 14, 2006, provisional application No. 60/728,292, filed on Oct. 19, 2005, provisional application No. 60/751,196, filed on Dec. 16, 2005, provisional application No. 60/864,530, filed on Nov. 6, 2006, provisional application No. 61/258,369, filed on Nov. 5, 2009, provisional application No. 61/258,729, filed on Nov. 6, 2009, provisional application No. 61/378,059, filed on Aug. 30, 2010, provisional application No. 61/166,809, filed on Apr. 6, 2009, provisional application No. 61/168,715, filed on Apr. 13, 2009, provisional application No. 60/544,227, filed on Feb. 13, 2004, provisional application No. 61/238,473, filed on Aug. 31, 2009, provisional application No. 61/266,305, filed on Dec. 3, 2009, provisional application No. 61/316,996, filed on Mar. 24, 2010, provisional application No. 61/323,960, filed on Apr. 14, 2010, provisional application No. 61/238,424, filed on Aug. 31, 2009, provisional application No. 61/168,290, filed on Apr. 10, 2009, provisional application No. 61/168,657, filed on Apr. 13, 2009, provisional application No. 61/168,668, filed on Apr. 13, 2009, provisional application No. 61/163,666, filed on Mar. 26, 2009, provisional application No. 60/668,603, filed on Apr. 6, 2005, provisional application No. 61/090,487, filed on Aug. 20, 2008, provisional application No. 61/043,932, filed on Apr. 10, 2008, provisional application No. 61/104,916, filed on Oct. 13, 2008, provisional application No. 61/119,542, filed on Dec. 3, 2008, provisional application No. 61/267,877, filed on Dec. 9, 2009, provisional application No. 61/302,682, filed on Feb. 9, 2010, provisional application No. 61/414,592, filed on Nov. 17, 2010.

(56) References Cited

U.S. PATENT DOCUMENTS

| | | |
|---|---|---|
| 7,871,622 B2 | 1/2011 | Chang et al. |
| 7,901,680 B2 | 3/2011 | Chang et al. |
| 7,906,121 B2 | 3/2011 | Chang et al. |
| 7,981,398 B2 | 7/2011 | Chang et al. |
| 8,003,111 B2 | 8/2011 | Chang et al. |
| 8,034,352 B2 | 10/2011 | Chang et al. |
| 8,158,129 B2 | 4/2012 | Chang et al. |
| 8,163,291 B2 | 4/2012 | Chang et al. |
| 8,211,440 B2 | 7/2012 | Chang et al. |
| 8,246,960 B2 | 8/2012 | Chang et al. |
| 8,277,817 B2 | 10/2012 | Chang et al. |
| 8,282,934 B2 | 10/2012 | Chang et al. |
| 8,349,332 B2 | 1/2013 | Chang et al. |
| 8,435,540 B2 | 5/2013 | Chang et al. |
| 8,475,794 B2 | 7/2013 | Chang et al. |
| 8,481,041 B2 | 7/2013 | Chang et al. |
| 8,491,914 B2 | 7/2013 | Chang et al. |
| 8,551,480 B2 | 10/2013 | Chang et al. |

(56) References Cited

U.S. PATENT DOCUMENTS

| | | | |
|---|---|---|---|
| 8,562,988 | B2 | 10/2013 | Chang et al. |
| 8,597,659 | B2 | 12/2013 | Chang et al. |
| 2002/0040130 | A1 | 4/2002 | Braun |
| 2003/0198956 | A1 | 10/2003 | Makowski et al. |
| 2003/0232420 | A1 | 12/2003 | Braun et al. |
| 2004/0018587 | A1 | 1/2004 | Makowski et al. |
| 2005/0003403 | A1 | 1/2005 | Rossi et al. |
| 2005/0255487 | A1* | 11/2005 | Khvorova et al. ............ 435/6 |
| 2006/0154330 | A1 | 7/2006 | Klussmann et al. |
| 2006/0210475 | A1 | 9/2006 | Goldenberg et al. |
| 2006/0228300 | A1 | 10/2006 | Chang et al. |
| 2006/0228357 | A1 | 10/2006 | Chang et al. |
| 2007/0020259 | A1 | 1/2007 | Hansen et al. |
| 2007/0086942 | A1 | 4/2007 | Chang et al. |
| 2009/0060862 | A1 | 3/2009 | Chang et al. |
| 2009/0111143 | A1 | 4/2009 | Goldenberg et al. |
| 2009/0202433 | A1 | 8/2009 | Chang et al. |
| 2009/0202487 | A1 | 8/2009 | Chang et al. |
| 2009/0304580 | A1 | 12/2009 | Goldenberg et al. |
| 2010/0068137 | A1 | 3/2010 | Chang et al. |
| 2010/0189641 | A1 | 7/2010 | Chang et al. |
| 2010/0189689 | A1 | 7/2010 | Chang et al. |
| 2010/0196266 | A1 | 8/2010 | Goldenberg et al. |
| 2011/0020273 | A1 | 1/2011 | Chang et al. |
| 2011/0064754 | A1 | 3/2011 | Taylor et al. |
| 2011/0143417 | A1 | 6/2011 | Chang et al. |
| 2011/0158905 | A1 | 6/2011 | Goldenberg et al. |
| 2011/0189083 | A1 | 8/2011 | Chang et al. |
| 2012/0093769 | A1 | 4/2012 | Chang et al. |
| 2012/0196346 | A1 | 8/2012 | Chang et al. |
| 2012/0276100 | A1 | 11/2012 | Chang et al. |
| 2012/0276608 | A1 | 11/2012 | Chang et al. |
| 2013/0078183 | A1 | 3/2013 | Chang et al. |
| 2013/0109073 | A1 | 5/2013 | Chang et al. |
| 2013/0164816 | A1 | 6/2013 | Chang et al. |
| 2013/0177532 | A1 | 7/2013 | Chang et al. |
| 2013/0217091 | A1 | 8/2013 | Chang et al. |
| 2013/0295005 | A1 | 11/2013 | Chang et al. |

FOREIGN PATENT DOCUMENTS

| | | |
|---|---|---|
| WO | 2006/107617 | 10/2006 |
| WO | 2006/107786 | 10/2006 |
| WO | 2007046893 A2 | 4/2007 |
| WO | WO2007075270 | 7/2007 |
| WO | 2007134037 | 11/2007 |
| WO | 2008/033413 | 3/2008 |
| WO | 2009055653 | 4/2009 |
| WO | 2009126558 | 10/2009 |

OTHER PUBLICATIONS

Golay et al., Archives of Biochemistry and Biophysics 526: 146-153, 2012.*

Jubala et al., Vet Pathol 42: 468-476, 2005.*

Yu et al., Investigative Ophthalmology & Visual Science 49(2): 522-527, Feb. 2008.*

Dykxhoorn et al., cell 126: 231-235, Jul. 28, 2006.*

Rossi et al., Bioconjugate Chemistry 24: 63-71, Jan. 16, 2013.*

Kim et al., Trends in Molecular Medicine 15(11): 491-500, 2009.*

Eck et al., Gene-Based Therapy, In: The Pharmacological Basis of Therapeutics, Goodman and Gilman, Ed.s, 1996, pp. 77-101.*

Hay et al., Nature Biotechnology 32(1): 40-51, Jan. 2014.*

Gupta et al., Cancer Res 70(8): Abstract No. LB-34, Apr. 15, 2010.*

Abbas et al., Cellular and Molecular Immunology, W.B. Saunders Company, 1991, p. 43.

Alto et al., "Bioinformatic design of A-kinase anchoring protein-in silico: A potent and selective peptide antagonist of type II protein kinase A anchoring", PNAS USA 100:4445-50, 2003.

Backer et al., "Self-Assembled "Dock and Lock" System for Linking Payloads to Targeting Proteins", Bioconjugate Chem., 17 (4), pp. 912-919, 2006.

Baillie et al., "Compartmentalisation of phospodiesterases and protein kinase A: opposites attract", FEBS Letters 2005; 579:3264-3270.

Banky et al., "Dimerization/Docking Domain of the Type Iα Regulatory Subunit of cAMP-dependent Protein Kinase", J. Biol. Chem. 273:35048-55, 1998.

Basu et al., "Structure-Function Engineering of Interferon-β-1b for Improving Stability, Solubility, Potency, Immunogenicity, and Pharmacokinetic Properties by Site-Selective Mono-PEGylation", Bioconjugate Chem. 2006; 17:618-630.

Belardelli et al., "Interferon-alpha in tumor immunity and immunotherapy" Cytokine Growth Factor Rev. 13(2):119-134 (2002).

Belardelli et al., "International Meeting on Cancer Vaccines: How Can We Enhance Efficacy of Therapeutic Vaccines?" Cancer Res. 64:6827-6830 (2004).

Belardelli et al., "The neglected role of type I interferon in the T-cell response: implications for its clinical use" Immunol. Today 17(8):369-72 (1996).

Biron et al., "Natural killer cells in antiviral defense: function and regulation by innate cytokines" Annu. Rev. Immunol. 17:189-220 (1999).

Brunda et al., "Modulation of Murine Natural Killer Cell Activity in Vitro and in Vivo by Recombinant Human Interferons" Cancer Res. 44:597-601 (1984).

Burns-Hamuro et al., "Distinct interaction modes of an AKAP bound to two regulatory subunit isoforms of protein kinase A revealed by amide hydrogen/deuterium exchange" Protein Science (2005), 14:2982-2992.

Carr et al., "Interaction of the Regulatory Subunit (RII) of cAMP-dependent Protein Kinase with RII-anchoring Proteins Occurs through an Amphipathic Helix Binding Motif", J. Biol. Chem. 266:14188-92 (1991).

Carr et al., "Identification of Sperm-specific Proteins That Interact with A-kinase Anchoring Proteins in a Manner Similar to the Type II Regulatory Subunit of PKA" J. Biol. Chem. 276(20):17332-17338 (2001).

Carrero et al., "Lymphocytes are detrimental during the early innate immune response against Listeria monocytogenes" J. Exp. Med. 203(4):933-940 (2006).

Chang et al., "The Dock and Lock Method: A Novel Platform Technology for Building Multivalent, Multifunctional Structures of Defined Composition with Retained Bioactivity" Clin. Cancer Res. Sep. 15, 2007;13(18 Suppl), pp. 5586-5591.

Chmura et al., "Antibodies with infinite affinity" Proc. Natl. Acad. Sci. USA 98(15):8480-8484 (2001).

Colledge et al., "AKAPs: from structure to function", Trends Cell Biol. 6:216-21 (1999).

Corbin et al., "Regulation of Adenosine 3',5'-Monophosphate-dependent Protein Kinase", J. Biol. Chem. 248:1813-21 (1973).

Dhalluin et al., "Structural and Biophysical Characterization of the 40 kDa PEG-Interferon-α2a and Its Individual Positional Isomers" Bioconjugate Chem. 2005;16:504-517.

Dodart et al., "Immunotherapy for Alzheimer's Disease: will vaccination work?" Trends Mol. Med. 9(3):85-87 (2003).

Doherty et al., "Site-Specific PEGylation of Engineered Cysteine Analogues of Recombinant Human Granulocyte-Macrophage Colony-Stimulating Factor", Bioconjugate Chem. 2005;16:1291-1298.

Ferrantini et al., "IFN-α1 Gene Expression into a Metastatic Murine Adenocarcinoma (TS/A) Results in CD8+ T Cell-Mediated Tumor Rejection and Development of Antitumor Immunity" J. Immunol. 153:4604-15 (1994).

Ferrantini et al., "Interferon-α and cancer: Mechanisms of action and new perspectives of clinical use" Biochimie 89: 884-893 (2007).

Gillies et al., "High-level expression of chimeric antibodies using adapted cDNA variable region cassettes", J. Immunol. Methods 125 (1989) 191-202.

Glennie et al., "Mechanisms of killing by anti-CD20 monoclonal antibodies" Mol. Immunol. 44:3823-3837 (2007).

Gold et al., "A Novel Bispecific, Trivalent Antibody Construct for Targeting Pancreatic Carcinoma", Cancer Res. 68:4819-26, 2008.

(56) References Cited

OTHER PUBLICATIONS

Gold et al., "Molecular Basis of AKAP Specificity for PKA Regulatory Subunits" Mol. Cell Nov. 3, 2006;24(3):383-95.
Goldenberg et al., "Multifunctional Antibodies by the Dock-and-Lock Method for Improved Cancer Imaging and Therapy by Pretargeting", J. Nucl. Med. 49:158-63, 2008.
Goldenberg et al., "Properties and structure-function relationships of veltuzumab (hA20), a humanized anti-CD20 monoclonal antibody" Blood 113:1062-70 (2009).
Goodson et al., "Site-Directed PEGylation of Recombinant Interleukin-2 at its Glycosylation Site", Nat. Biotechnology Apr. 1990;8(4):343-6.
Grace et al., "Site of Pegylation and Polyethylene Glycol Molecule Size Attenuate Interferon-α Antiviral and Antiproliferative Activities through the JAK/STAT Signaling Pathway" J. Biol. Chem. 2005;280(8):6327-6336.
Grimley et al., "Prolonged STAT1 Activation Related to the Growth Arrest of Malignant Lymphoma Cells by Interferon-α" Blood 91(8):3017-27 (1998).
Gutterman et al., "Leukocyte Interferon-Induced Tumor Regression in Human Metastatic Breast Cancer, Multiple Myeloma, and Malignant Lymphoma" Ann. Intern. Med. 93(3):399-406 (1980).
Gutterman et al., "Cytokine therapeutics: Lessons from interferon α" Proc. Natl. Acad. Sci. USA 91:1198-205 (1994).
Harris et al., "Effect of pegylation on pharmaceuticals" Nat. Rev. Drug. Discov. 2:214-221 (2003).
Hausken et al. "Mutational Analysis of the A-Kinase Anchoring Protein (AKAP)-binding Site on RII", J. Biol. Chem. 271:29016-22 (1996).
Hodneland et al., "Selective immobilization of proteins to self-assembled monolayers presenting active site-directed capture ligands", Proc. Natl. Acd. Sci. USA 2002; 99:5048-5052.
Huang et al., "Targeting IFN-α to B Cell Lymphoma by a Tumor-Specific Antibody Elicits Potent Antitumor Activities" J. Immunol. 179:6881-88 (2007).
Hundsrucker et al., "High-affinity AKAP7δ-protein kinase A interaction yields novel protein kinase A-anchoring disruptor peptides" Biochem. J. (2006) 396, 297-306.
Kimby et al., "Long-term molecular remissions in patients with indolent lymphoma treated with rituximab as a single agent or in combination with interferon alpha-2a: A randomized phase II study from the Nordic Lymphoma Group" Leuk. Lymphoma 49(1):102-112 (2008).
Kinderman et al., "A Dynamic Mechanism for AKAP Binding to RII Isoforms of cAMP-Dependent Protein Kinase" Mol. Cell 24(3):397-408 (2006).
Kinstler et al., "Characterization and Stability of N-terminally PEGylated rhG-CSF" Pharm. Res. 1996;13 (7):996-1002.
Kramer et al., "Cell and virus sensitivity studies with recombinant human alpha interferons" J. Interferon. Res. 3 (4):425-35 (1983).
Le Bon et al., "Type I Interferons Potently Enhance Humoral Immunity and Can Promote Isotype Switching by Stimulating Dendritic Cells In Vivo" Immunity 14:461-470 (2001).
Lee et al., "Solid-Phase PEGylation of Recombinant Interferon α-2a for Site-Specific Modification: Process Performance, Characterization, and in Vitro Bioactivity" Bioconjugate Chem. 2007; 18:1728-34.
Lohmann et al., "High-affinity binding of the regulatory subunit (RII) of cAMP-dependent protein kinase to microtubule-associated and other cellular proteins", Proc. Natl. Acad. Sci. USA 81:6723-27 (1984).
Luft et al., "Type I IFNs Enhance the Terminal Differentiation of Dendritic Cells" J. Immunol. 161:1947-1953 (1998).
Mason, Anthony J., "Functional Analysis of the Cysteine Residues of Activin A", Mol. Endocrinol. 8:325-32, 1994.
Matarrese et al., "Type I Interferon Gene Transfer Sensitizes Melanoma Cells to Apoptosis via a Target Activity on Mitochondrial Function" Am. J. Pathol. 2002, 160(4):1507-1520.
Mecchia et al., "Type I consensus interferon (CIFN) gene transfer into human melanoma cells up-regulates p53 and enhances cisplatin-induced apoptosis: implications for new therapeutic strategies with IFN-alpha" Gene Ther. (2000) 7, 167-179.
Newlon et al., "A Novel Mechanism of PKA Anchoring Revealed by Solution Structures of Anchoring Complexes", EMBO J. 2001; 20:1651-1662.
Newlon et al., "The molecular basis for protein kinase A anchoring revealed by solution NMR", Nature Stud. Biol. 1999; 3:222-227.
Ngo et al., "Computational Complexity, Protein Structure Prediction, and the Levinthal Paradox", The Protein Folding Problem and Tertiary Structure Prediction, Ch. 14, pp. 492-495, (Mertz & Le Grand, Eds.), Birkhauser Boston, 1994.
Nordstrom et al., "First Bispecific Antibody Immunocytokine (Anti-CD20/HLA-DR-Interferon-α2b) is Highly Toxic for Human Lymphoma Cells in Vitro", 2009 ASH Annual Meeting Abstracts, Nov. 20, 2009; 114(22):675, Abstract # 1695.
Osborn et al., "Pharmacokinetic and Pharmacodynamic Studies of a Human Serum Albumin-Interferon-α Fusion Protein in Cynomolgus Monkeys" J. Pharmacol. Exp. Ther. 303(2):540-548 (2002).
Oyen et al., "Human testis cDNA for the regulatory subunit RIIα of cAMP-dependent protein kinase encodes an alternate amino-terminal region", FEBS Letters 246:57-64, 1989.
Ozzello et al., "Conjugation of interferon alpha to a humanized monoclonal antibody (HuBrE-3vl) enhances the selective localization and antitumor effects of interferon in breast cancer xenografts" Breast Cancer Res. Treat. 48: 135-147 (1998).
Paquette et al., "Interferon-α and granulocyte-macrophage colony-stimulating factor differentiate peripheral blood monocytes into potent antigen-presenting cells" J. Leukoc. Biol. 64:358-367; 1998.
Pelham et al., "Interferon-α conjugation to human osteogenic sarcoma monoclonal antibody 791T/36" Cancer Immunol. Immuother. 1983;15(3):210-216.
Pepinsky et al., "Improved Pharmacokinetic Properties of a Polyethylene Glycol-Modified Form of Interferon-β-1a with Preserved in Vitro Bioactivity" Pharmacol. Exp. Ther. 2001; 297(3):1059-1066.
Pilling et al., "Interferon-β mediates stromal cell rescue of T cells from apoptosis" Eur. J. Immunol. 29:1041-1050 (1999).
Rabjohn et al., "Molecular Cloning and Epitope Analysis of the Peanut Allergen Ara h 3" J. Clinical Investigation 103 (4):535-542 (1999).
Raefsky et al., "Studies of Interferon as a regulator of hematopoietic cells proliferation" J. Immunol. 135 (4):2507-2512 (1985).
Rose et al., "Structural basis of dimerization, coactivator recognition and MODY3 mutations in HNF-1α", Nature Struct. Biol. 2000; 7:744-748.
Rosendahl et al., "A Long-Acting, Highly Potent Interferon α-2 Conjugate Created Using Site-Specific PEGylation" Bioconjugate Chem. 2005;16:200-207.
Rossi et al., "Novel Designs of Multivalent Anti-CD20 Humanized Antibodies as Improved Lymphoma Therapeutics", Cancer Res. 68:8384-92, 2008.
Rossi et al., "Stably tethered multifunctional structures of defined composition made by the dock and lock method for use in cancer targeting" Proc. Natl. Acad. Sci. Epub Apr. 24, 2006, vol. 103, No. 18, pp. 6841-6846.
Rossi et al., "CD20-targeted tetrameric interferon-α, a novel and potent immunocytokine for the therapy of B-cell lymphomas", Blood 2009;114:3864-3871.
Rossi et al., "A veltuzumab-IFNα2b conjugate with potent in vitro and in vivo anti-lymphoma activity", Proceedings of the American Association for Cancer Research, Apr. 2009;50:783-784, Abstract # 3237.
Rustandi et al., "The Ca2+-Dependent Interaction of S100B(ββ) with a Peptide Derived from p53", Biochemistry 1998; 37: 1951-1960.
Sabaawy et al., "Enhancement of 5-fluorouracil cytotoxicity on human colon cancer cells by retrovirus-mediated interferon-α gene transfer" Int. J. Oncol. Jun. 1999; 14(6):1143-51.
Salles et al., "Rituximab combined with chemotherapy and interferon in follicular lymphoma patients: results of the Gela-Goelams FL2000 study" Blood 2008; 112:4824-4831.

(56) References Cited

OTHER PUBLICATIONS

Santini et al., "Type I Interferon as a Powerful Adjuvant for Monocyte-derived Dendritic Cell Development and Activity In Vivo and in Hu-PBL-SCID Mice" J. Exp. Med. 191(10):1777-1788 (2000).

Scott et al., "Type II Regulatory Subunit Dimerization Determines the Subcellular Localization of the cAMP-dependent Protein Kinase", J. Biol. Chem. 265:21561-66 (1990).

Scott et al., "Cyclic nucleotide-dependent protein kinases" Pharmacol. Ther. 1991;50(1):123-45.

Seffernick et al., "Melamine Deaminase and Atrazine Chlorohydrolase: 98 Percent Identical but Functionally Different" J. Bacteriol. 183(8):2405-2410 (2001).

Sharkey et al., "Improved Therapeutic Results by Pretargeted Radioimmunotherapy of Non-Hodgkin's Lymphoma with a New Recombinant, Trivalent, Anti-CD20, Bispecific Antibody", Cancer Res. 68:5282-90, 2008.

Sharkey et al., "Metastatic Human Colonic Carcinoma: Molecular Imaging with Pretargeted SPECT and PET in a Mouse Model", Radiology 246:497-507, 2008.

Sidky et al., "Inhibition of Angiogenesis by Interferons: Effects on Tumor- and Lymphocyte-induced Vascular Responses" Cancer Res. 47:5155-5161, Oct. 1, 1987.

Stein et al., "Characterization of a New Humanized Anti-CD20 Monoclonal Antibody, IMMU-106, and Its Use in Combination with the Humanized Anti-CD22 Antibody, Epratuzumab, for the Therapy of Non-Hodgkin's Lymphoma" Clin. Cancer Res. vol. 10, 2868-2878, Apr. 15, 2004.

Stein et al., "Characterization of a humanized IgG4 anti-HLA-DR monoclonal antibody that lacks effector cell functions but retains direct antilymphoma activity and increases the potency of rituximab" Blood 2006;108:2736-2744.

Stokka et al., "Characterization of A-kinase-anchoring disruption using a solution-based assay" Biochem. J. (2006) 400, 493-499.

Stryer et al., "Levels of Structure in Protein Architecture", Biochemistry, 3rd Ed., pp. 31-33, W.H. Freeman & Co., New York, 1988.

Takaoka et al., "Integration of interferon-α/β signalling to p53 responses in tumour suppression and antiviral defence" Nature Jul. 31, 2003;424(6948):516-23.

Taylor, S., "cAMP-dependent Protein Kinase" J. Biol. Chem. 1989;264(15):8443-8446.

Walsh et al., "An Adenosine 3', 5'-Monophosphate-dependant Protein Kinase from Rabbit Skeletal Muscle" J. Biol. Chem. 243(13):3763-3774 (1968).

Weck et al., "Comparison of the Antiviral Activities of Various Cloned Human Interferon-α Subtypes in Mammalian Cell Cultures" J. Gen. Virol. (1981), 57, 233-237.

Winkler et al., "Changing the Antigen Binding Specificity by Single Point Mutations of an Anti-p24 (HIV-1) Antibody", J. Immunol. 165:4505-14, 2000.

Witkowski et al., "Conversion of a β-Ketoacyl Synthase to a Malonyl Decarboxylase by Replacement of the Active-Site Cysteine with Glutamine" Biochemistry 38(36):11643-50 (1999).

Wong et al., "AKAP Signalling Complexes: Focal Points in Space and Time", Nat. Rev. Mol. Cell Biol. 12:959-70 (2004).

Zhu et al., "Inhibition of tumor growth and metastasis by targeting tumor-associated angiogenesis with antagonists to the receptors of vascular endothelial growth factor", Invest. New Drugs 17:195-212, 1999.

Belyakov et al., "Shared modes of protection against poxvirus infection by attenuated and conventional smallpox vaccine viruses", Proc Natl Acad Sci U S A. Aug. 5, 2003;100(16):9458-63. Epub Jul. 17, 2003.

Berhanu et al., Vaccination of BALB/c mice with *Escherichia coli*-expressed vaccinia virus proteins A27L, B5R, and D8L protects mice from lethal vaccinia virus challenge, J Virol. Apr. 2008;82(7):3517-29. Epub Jan. 16, 2008.

Born et al., "A poxvirus protein that binds to and inactivates IL-18, and inhibits NK cell response", J Immunol. Mar. 15, 2000;164(6):3246-54.

Carayanniotis et al., "Characterization of the adjuvant-free serological response to protein antigens coupled to antibodies specific for class II MHC determinants", Vaccine. Apr. 1990;8(2):137-44.

Chung et al., "A27L protein mediates vaccinia virus interaction with cell surface heparan sulfate", J Virol. Feb. 1998;72(2):1577-85.

Ding et al., "Targeting of antigens to B cells augments antigen-specific T-cell responses and breaks immune tolerance to tumor-associated antigen MUC1", Blood. Oct. 1, 2008;112(7):2817-25. Epub Jul. 31, 2008.

Grandpre et al., "Immunogenicity of recombinant Modified Vaccinia Ankara following a single or multi-dose vaccine regimen in rhesus monkeys", Vaccine. Mar. 4, 2009;27(10):1549-56. Epub Jan. 23, 2009.

He et al., "Antibodies to the A27 protein of vaccinia virus neutralize and protect against infection but represent a minor component of Dryvax vaccine—induced immunity", J Infect Dis. Oct. 1, 2007;196(7):1026-32. Epub Aug. 20, 2007.

Hsiao et al., "Vaccinia virus envelope D8L protein binds to cell surface chondroitin sulfate and mediates the adsorption of intracellular mature virions to cells", J Virol. Oct. 1999;73(10):8750-61.

Jackson et al., "Role of genes that modulate host immune responses in the immunogenicity and pathogenicity of vaccinia virus", J Virol. May 2005;79(10):6554-9.

Kan-Mitchell et al., "The HIV-1 HLA-A2-SLYNTVATL is a help-independent CTL epitope", J Immunol. May 1, 2004;172(9):5249-61.

Kretz-Rommel et al., "In vivo targeting of antigens to human dendritic cells through DC-SIGN elicits stimulatory immune responses and inhibits tumor growth in grafted mouse models", J Immunother. Oct. 2007;30(7):715-26.

Livingston et al., "A rational strategy to design multiepitope immunogens based on multiple Th lymphocyte epitopes", J Immunol. Jun. 1, 2002;168(11):5499-506.

O'Neill et al., "Exploiting dendritic cells for active immunotherapy of cancer and chronic infections", Mol Biotechnol. Jun. 2007;36(2):131-41.

Pien et al., "A unique mechanism for innate cytokine promotion of T cell responses to viral infections", J Immunol. Nov. 15, 2002;169(10):5827-37.

Rosenthal et al., "Developing new smallpox vaccines", Emerg Infect Dis. Nov.-Dec. 2001;7(6):920-6.

Scott et al., "IFN-gamma modulates the early development of Th1 and Th2 responses in a murine model of cutaneous leishmaniasis", J Immunol. Nov. 1, 1991;147(9):3149-55.

Song et al., "Antibody mediated in vivo delivery of small interfering RNAs via cell-surface receptors", Nat Biotechnol. Jun. 2005;23(6):709-17.

Tacken et al., "Dendritic-cell immunotherapy: from ex vivo loading to in vivo targeting", Nat Rev Immunol. Oct. 2007;7(10)190-802.

Tew et al., "Follicular dendritic cells and presentation of antigen and costimulatory signals to B cells", Immunol Rev. Apr. 1997;156:39-52.

Vulink et al., "Dendritic cells in cancer immunotherapy", Adv Cancer Res. 2008;99:363-407.

Xiang et al., "IL-18 binding and inhibition of interferon gamma induction by human poxvirus-encoded proteins", Proc Natl Acad Sci U S A. Sep. 28, 1999;96(20):11537-42.

Xu et al., "The orthopoxvirus type I IFN binding protein is essential for virulence and an effective target for vaccination", J Exp Med. Apr. 14, 2008;205(4):981-92. Epub Apr. 7, 2008.

Cardillo et al., "Targeting both IGF-1R and mTOR synergistically inhibits growth of renal cell carcinoma in vitro", BMC Cancer. Apr. 1, 2013;13:170.

Chang et al., "A new method to produce monoPEGylated dimeric cytokines shown with human interferon-α2b", Bioconjug Chem. Oct. 21, 2009;20(10):1899-907.

Chang et al., "A novel class of anti-HIV agents with multiple copies of enfuvirtide enhances inhibition of viral replication and cellular transmission in vitro", PLoS One. 2012;7(7):e41235.

(56) References Cited

OTHER PUBLICATIONS

Chang et al., "Evaluation of a novel hexavalent humanized anti-IGF-1R antibody and its bivalent parental IgG in diverse cancer cell lines", PLoS One. 2012;7(8):e44235.

Goldenberg et al., "Cancer Imaging and Therapy with Bispecific Antibody Pretargeting", Update Cancer Ther. Mar. 2007;2(1):19-31.

Govindan et al., "Designing immunoconjugates for cancer therapy", Expert Opin Biol Ther. Jul. 2012;12(7):873-90.

Rossi et al., "Hexavalent bispecific antibodies represent a new class of anticancer therapeutics: 1. Properties of anti-CD20/CD22 antibodies in lymphoma", Blood. Jun. 11, 2009;113(24):6161-71.

Rossi et al., "The dock-and-lock method combines recombinant engineering with site-specific covalent conjugation to generate multifunctional structures", Bioconjug Chem. Mar. 21, 2012;23(3):309-23.

Rossi et al., "Complex and defined biostructures with the dock-and-lock method", Trends Pharmacol Sci. Sep. 2012;33(9):474-81.

Rossi et al., "Optimization of multivalent bispecific antibodies and immunocytokines with improved in vivo properties", Bioconjug Chem. Jan. 16, 2013;24(1):63-71.

Rossi et al., "A new class of bispecific antibodies to redirect T cells for cancer immunotherapy", MAbs. Mar.-Apr. 2014;6(2):381-91.

Sharkey et al., "Improved cancer therapy and molecular imaging with multivalent, multispecific antibodies", Cancer Biother Radiopharm. Feb. 2010;25(1):1-12.

Liu et al., "Trop-2-targeting tetrakis-ranpirnase has potent antitumor activity against triple-negative breast cancer", Mol Cancer Mar. 10, 2014;13:53.

\* cited by examiner

Gel shift assay using a 200-bp DNA fragment, E1-L-thP1, and 2% agarose

Lanes *c-g* contain increasing amount of E1-L-thP1;
Lane *a* contains hRS7-IgG-AD2;

DOCK-AND-LOCK (DNL) COMPLEXES FOR DELIVERY OF INTERFERENCE RNA

RELATED APPLICATIONS

This application is a continuation of U.S. patent application Ser. No. 12/964,021, filed Dec. 9, 2010, which was a continuation-in-part of U.S. patent application Ser. No. 12/949,536 (now U.S. Pat. No. 8,211,440), filed Nov. 18, 2010, (which was a divisional of Ser. No. 12/396,605 (now U.S. Pat. No. 7,858,070), filed Mar. 3, 2009, which was a divisional of U.S. Pat. No. 7,527,787); Ser. No. 12/915,515, filed Oct. 29, 2010; Ser. No. 12/871,345, filed Aug. 30, 2010; Ser. No. 12/869,823, filed Aug. 27, 2010; Ser. No. 12/754,740, filed Apr. 6, 2010; Ser. No. 12/752,649 (now U.S. Pat. No. 8,034,352), filed Apr. 1, 2010; Ser. No. 12/731,781 (now U.S. Pat. No. 8,003,111), filed Mar. 25, 2010; Ser. No. 12/644,146 (now U.S. Pat. No. 7,981,398), (which was a divisional of U.S. Pat. No. 7,666,400), filed Dec. 22, 2009; Ser. No. 12/544,476 (now U.S. Pat. No. 7,901,680), filed Aug. 20, 2009; Ser. No. 12/468,589 (now U.S. Pat. No. 8,163,291), (which was a divisional of U.S. Pat. No. 7,550,143), filed May 19, 2009; Ser. No. 12/418,877 (now U.S. Pat. No. 7,906,118), filed Apr. 6, 2009; Ser. No. 12/417,917 (now U.S. Pat. No. 7,906,121), (which was a divisional of U.S. Pat. No. 7,534,866), filed Apr. 3, 2009; and Ser. No. 12/396,965 (now U.S. Pat. No. 7,871,622), (which was a divisional of U.S. Pat. No. 7,521,056), filed Mar. 3, 2009. Those applications claimed the benefit under 35 U.S.C. 119(e) of provisional U.S. Patent Applications 61/378,059, filed Aug. 30, 2010; 61/323,960, filed Apr. 14, 2010; 61/316,996, filed Mar. 24, 2010; 61/266,305, filed Dec. 3, 2009; 61/258,729, filed Nov. 6, 2009; 61/258,369, filed Nov. 5, 2009; 61/238,424, filed Aug. 31, 2009; 61/238,473, filed Aug. 31, 2009; 61/168,715, filed Apr. 13, 2009; 61/168,668, filed Apr. 13, 2009; 61/168,657, filed Apr. 13, 2009; 61/168,290, filed Apr. 10, 2009; 61/166,809, filed Apr. 6, 2009; 61/163,666, filed Mar. 26, 2009; 61/119,542, filed Dec. 3, 2008; 61/104,916, filed Oct. 13, 2008; 61/090,487, filed Aug. 20, 2008; 61/043,932, filed Apr. 6, 2008; 60/864,530, filed Nov. 6, 2006; 60/782,332, filed Mar. 14, 2006; 60/751,196, filed Dec. 16, 2005; 60/728,292, filed Oct. 19, 2005; 60/668,603, filed Apr. 6, 2005; and 60/544,227, filed Feb. 13, 2004. This application claims the benefit under 35 U.S.C. 119(e) of U.S. Provisional Patent Application Ser. Nos. 61/267,877, filed Dec. 9, 2009; 61/302,682, filed Feb. 8, 2010 and 61/414,592, filed Nov. 17, 2010. The text of each priority application is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Dec. 23, 2010, is named IBC125US.txt and is 29,000 bytes in size.

BACKGROUND OF THE INVENTION

1. Field of the Invention

This invention concerns compositions and methods for targeted delivery of RNAi species, such as siRNA. Preferably, the targeted delivery complexes comprise an antibody, antibody fragment or other targeting molecule conjugated to a carrier molecule for siRNA, such as a protamine or a dendrimer. More preferably, the targeted delivery complexes are made by the dock-and-lock (DNL) technique. The targeted delivery complex may comprise one or more siRNA species for delivery to a targeted cell or tissue. Most preferably, delivery of siRNA is effective to treat a disease, syndrome or disorder, such as cancer, autoimmune disease, immune dysfunction (e.g., graft-versus-host disease or organ transplant rejection), inflammation, infectious disease, cardiovascular disease, endocrine or metabolic disease or neurodegenerative disease. For disease therapy, the antibody or other targeting molecule binds to a target antigen produced by a diseased cell or tissue or otherwise associated with the disease state. The DNL complex may comprise multiple copies of a carrier molecule to efficiently deliver therapeutic siRNA to a target cell. The antibody or other targeting molecule may be a rapidly internalizing species to facilitate intracellular uptake of siRNA.

2. Related Art

RNA interference (RNAi) is a naturally occurring regulatory mechanism for control of gene expression in cells (Fire et al., 1998, Nature 391:806-11). RNAi is mediated by the RNA-induced silencing complex (RISC) and is initiated by short double-stranded RNA molecules that interact with the catalytic RISC component argonaute (Rand et al., 2005, Cell 123:621-29). Types of RNAi molecules include micro-RNA (miRNA) and small interfering RNA (siRNA). RNAi species can bind with messenger RNA (mRNA) through complementary base-pairing and inhibits gene expression by post-transcriptional gene silencing. Upon binding to a complementary mRNA species, RNAi induces cleavage of the mRNA molecule by the argonaute component of RISC. Among other characteristics, miRNA and siRNA differ in the degree of specificity for particular gene targets, with siRNA being relatively specific for a particular target gene and miRNA inhibiting translation of multiple mRNA species.

Therapeutic use of RNAi by inhibition of selected gene expression has been attempted for a variety of disease states, such as macular degeneration and respiratory syncytial virus infection (Sah, 2006, Life Sci 79:1773-80). It has been suggested that siRNA functions in host cell defenses against viral infection and siRNA has been widely examined as an approach to anti-viral therapy (see, e.g., Zhang et al., 2004, Nature Med 11:56-62; Novina et al., 2002, Nature Med 8:681-86; Palliser et al., 2006, Nature 439:89-94). The use of siRNA for cancer therapy has also been attempted. Fujii et al. (2006, Int J Oncol 29:541-48) transfected HPV positive cervical cancer cells with siRNA against HPV E6 and E7 and suppressed tumor growth. siRNA-mediated knockdown of metadherin expression in breast cancer cells was reported to inhibit experimental lung metastasis (Brown and Ruoslahti, 2004, Cancer Cell 5:365-74).

Difficulties with siRNA-based therapies have included poor cellular uptake of exogenous siRNA and potential off-target effects on other genes (see, e.g., Kim et al., 2009, Trends Molec Med 15:491-500). Jackson et al. (2003, Nat Biotechnol 21:635-37) designed different siRNAs targeting IGF-1R and MAPK14 and showed silencing of nontargeted genes containing as few as eleven contiguous identical nucleotides to the siRNA species.

Attempts have been made to provide targeted delivery of siRNA to reduce the potential for off-target toxicity. Song et al. (2005, Nat Biotechnol 23:709-17) used protamine-conjugated Fab fragments against HIV envelope protein to deliver siRNA to circulating cells. Schiffelers et al. (2004, Nucl Acids Res 32:e149) conjugated RGD peptides to nanoparticles to deliver anti-VEGF R2 siRNA to tumors and inhibited tumor angiogenesis and growth rate in nude mice.

Dickerson et al. used nanogels functionalized with anti-EphA2 receptor peptides to chemosensitize ovarian cancer cells with siRNA against EGFR. Dendrimer-conjugated magnetic nanoparticles have been applied to the targeted delivery of antisense survivin oligodeoxynucleotides (Pan et al., 2007, Cancer Res 67:8156-63).

Despite recent progress, a need exists in the field for more effective means of targeted delivery of therapeutic siRNA, to increase cellular uptake and minimize siRNA-related toxic side effects (Kim et al., 2009).

SUMMARY

The present invention concerns methods and compositions for efficient delivery of siRNA species to disease-associated target cells, tissues or pathogens. Preferably, delivery is facilitated by use of targeted delivery complexes, which comprise an antibody, antibody fragment or other targeting molecule conjugated to a carrier molecule for siRNA, such as a protamine, dendrimer or nanoparticle. More preferably, the targeting molecule provides for highly selective or specific delivery of therapeutic siRNA to diseased cells or tissues. Most preferably, the targeted delivery complex facilitates intracellular uptake of siRNA into target cells.

The siRNA species to be delivered and the corresponding specificity of the targeting molecule will be determined by the disease state to be treated. As discussed in more detail below, tens of thousands of siRNA sequences directed to mRNAs associated with a broad variety of disease states are known in the art and may be obtained from public databases, such as siRNAdb database at the Stockholm Bioinformatics Centre, the MIT/ICBP siRNA Database, the RNAi Consortium shRNA Library at the Broad Institute, and the Probe database at NCBI. Many siRNA species may also be purchased from commercial vendors like Sigma-Aldrich (St Louis, Mo.), Invitrogen (Carlsbad, Calif.), Santa Cruz Biotechnology (Santa Cruz, Calif.), Ambion (Austin, Tex.), Dharmacon (Thermo Scientific, Lafayette, Colo.), Promega (Madison, Wis.), Minis Bio (Madison, Wis.) and Qiagen (Valencia, Calif.).

A variety of carrier moieties for siRNA have been reported and any such known carrier may be incorporated into a targeted delivery complex for use. Non-limiting examples of carriers include protamine (Rossi, 2005, Nat Biotech 23:682-84; Song et al., 2005, Nat Biotech 23:709-17); dendrimers such as PAMAM dendrimers (Pan et al., 2007, Cancer Res. 67:8156-8163); polyethylenimine (Schiffelers et al., 2004, Nucl Acids Res 32:e149); polypropyleneimine (Taratula et al., 2009, J Control Release 140: 284-93); polylysine (Inoue et al., 2008, J Control Release 126:59-66); histidine-containing reducible polycations (Stevenson et al., 2008, J Control Release 130:46-56); histone H1 protein (Haberland et al., 2009, Mol Biol Rep 26:1083-93); cationic comb-type copolymers (Sato et al., 2007, J Control Release 122:209-16); polymeric micelles (U.S. Patent Application Publ. No. 20100121043); and chitosan-thiamine pyrophosphate (Rojanarata et al., 2008, Pharm Res 25:2807-14). The skilled artisan will realize that in general, polycationic proteins or polymers are of use as siRNA carriers. The skilled artisan will further realize that siRNA carriers can also be used to carry other oligonucleotide or nucleic acid species, such as anti-sense oligonucleotides or short DNA genes.

Various embodiments may concern use of the targeted delivery complexes to treat a disease, including but not limited to non-Hodgkin's lymphomas, B-cell acute and chronic lymphoid leukemias, Burkitt lymphoma, Hodgkin's lymphoma, hairy cell leukemia, acute and chronic myeloid leukemias, T-cell lymphomas and leukemias, multiple myeloma, glioma, Waldenstrom's macroglobulinemia, carcinomas, melanomas, sarcomas, gliomas, and skin cancers. The carcinomas may be selected from the group consisting of carcinomas of the oral cavity, gastrointestinal tract, colon, stomach, pulmonary tract, lung, breast, ovary, prostate, uterus, endometrium, cervix, urinary bladder, pancreas, bone, liver, gall bladder, kidney, skin, and testes.

In addition, the targeted delivery complexes may be used to treat an autoimmune disease, for example acute idiopathic thrombocytopenic purpura, chronic idiopathic thrombocytopenic purpura, dermatomyositis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcal nephritis, erythema nodosum, Takayasu's arteritis, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitis obliterans, Sjogren's syndrome, primary biliary cirrhosis, Hashimoto's thyroiditis, thyrotoxicosis, scleroderma, chronic active hepatitis, polymyositis/dermatomyositis, polychondritis, pemphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis, psoriasis, or fibrosing alveolitis.

The compositions of the present invention also are useful for the treatment of infections, where the antibody component of the targeted delivery complex specifically binds to a disease-causing microorganism. In the context of the present invention a disease-causing microorganism includes pathogenic bacteria, viruses, fungi and diverse parasites, and the antibody can target these microorganisms, their products or antigens associated with their lesions. Examples of microorganisms include, but are not limited to: *Streptococcus agalactiae, Legionella pneumophilia, Streptococcus pyogenes, Escherichia coli, Neisseria gonorrhoeae, Neisseria meningitidis, Pneumococcus, Haemophilus influenzae B, Treponema pallidum,* Lyme disease spirochetes, *Pseudomonas aeruginosa, Mycobacterium leprae, Brucella abortus, Mycobacterium tuberculosis,* Tetanus toxin, HIV-1, -2, -3, Hepatitis A, B, C, D, Rabies virus, Influenza virus, Cytomegalovirus, Herpes simplex I and II, Human serum parvo-like virus, Papilloma viruses, Polyoma virus, Respiratory syncytial virus, Varicella-Zoster virus, Hepatitis B virus, Papilloma virus, Measles virus, Adenovirus, Human T-cell leukemia viruses, Epstein-Barr virus, Murine leukemia virus, Mumps virus, Vesicular stomatitis virus, Sindbis virus, Lymphocytic choriomeningitis virus, Wart virus, Blue tongue virus, Sendai virus, Feline leukemia virus, Reovirus, Polio virus, Simian virus 40, Mouse mammary tumor virus, Dengue virus, Rubella virus, protozoans, *Plasmodium falciparum, Plasmodium vivax, Toxoplasma gondii, Trypanosoma rangeli, Trypanosoma cruzi, Trypanosoma rhodesiense, Trypanosoma brucei, Schistosoma mansoni, Schistosoma japonicum, Babesia bovis, Eimeria tenella, Onchocerca volvulus, Leishmania tropica, Trichinella spiralis, Theileria parva, Taenia hydatigena, Taenia ovis, Taenia saginata, Echinococcus granulosus, Mesocestoides corti, Mycoplasma arthritidis, M. hyorhinis, M. orale, M. arginini, Acholeplasma laidlawii, M. salivarium,* and *M. pneumoniae.* Monoclonal antibodies that bind to these pathogenic microorganisms are well known in the art.

In one embodiment, a pharmaceutical composition of the present invention may be used to treat a subject having a metabolic disease, such amyloidosis, or a neurodegenerative disease, such as Alzheimer's disease. Bapineuzumab is in clinical trials for Alzheimer's disease therapy. Other antibodies proposed for therapy of Alzheimer's disease include Alz 50 (Ksiezak-Reding et al., 1987, J Biol Chem 263:7943-47), gantenerumab, and solanezumab. Infliximab, an anti-TNF-α antibody, has been reported to reduce amyloid plaques and improve cognition. Anti-CD3 antibodies have been proposed for therapy of type 1 diabetes (Cernea et al., 2010, Diabetes Metab Rev 26:602-05). In addition, a pharmaceutical composition of the present invention may be used to treat a subject having an immune-dysregulatory disorder such as graft-versus-host disease or organ transplant rejection.

In a preferred embodiment, diseases that may be treated using the claimed compositions and methods include cardiovascular diseases, such as fibrin clots, atherosclerosis, myocardial ischemia and infarction. Antibodies to fibrin (e.g., scFv(59D8); T2G1s; MH1) are known and in clinical trials as imaging agents for disclosing said clots and pulmonary emboli, while anti-granulocyte antibodies, such as MN-3, MN-15, anti-NCA95, and anti-CD15 antibodies, can target myocardial infarcts and myocardial ischemia. (See, e.g., U.S. Pat. Nos. 5,487,892; 5,632,968; 6,294,173; 7,541,440, the Examples section of each incorporated herein by reference) Anti-macrophage, anti-low-density lipoprotein (LDL) and anti-CD74 (e.g., hLL1) antibodies can be used to target atherosclerotic plaques. Abciximab (anti-glycoprotein IIb/IIIa) has been approved for adjuvant use for prevention of restenosis in percutaneous coronary interventions and the treatment of unstable angina (Waldmann et al., 2000, Hematol 1:394-408). Anti-CD3 antibodies have been reported to reduce development and progression of atherosclerosis (Steffens et al., 2006, Circulation 114:1977-84). Antibodies against oxidized LDL induced a regression of established atherosclerosis in a mouse model (Ginsberg, 2007, J Am Coll Cardiol 52:2319-21). Anti-ICAM-1 antibody was shown to reduce ischemic cell damage after cerebral artery occlusion in rats (Zhang et al., 1994, Neurology 44:1747-51). Commercially available monoclonal antibodies to leukocyte antigens are represented by: OKT anti-T-cell monoclonal antibodies (available from Ortho Pharmaceutical Company) which bind to normal T-lymphocytes; the monoclonal antibodies produced by the hybridomas having the ATCC accession numbers HB44, HB55, HB12, HB78 and HB2; G7Ell, W8E7, NKP15 and GO22 (Becton Dickinson); NEN9.4 (New England Nuclear); and FMCll (Sera Labs). A description of antibodies against fibrin and platelet antigens is contained in Knight, Semin. Nucl. Med., 20:52-67 (1990).

Antibodies or other targeting molecules of use may bind to any disease-associated antigen known in the art. Where the disease state is cancer, for example, many antigens expressed by or otherwise associated with tumor cells are known in the art, including but not limited to, carbonic anhydrase IX, alpha-fetoprotein, α-actinin-4, A3, antigen specific for A33 antibody, ART-4, B7, Ba 733, BAGE, BrE3-antigen, CA125, CAMEL, CAP-1, CASP-8/m, CCCL19, CCCL21, CD1, CD1a, CD2, CD3, CD4, CD5, CD8, CD11A, CD14, CD15, CD16, CD18, CD19, CD20, CD21, CD22, CD23, CD25, CD29, CD30, CD32b, CD33, CD37, CD38, CD40, CD40L, CD45, CD46, CD52, CD54, CD55, CD59, CD64, CD66a-e, CD67, CD70, CD74, CD79a, CD80, CD83, CD95, CD126, CD133, CD138, CD147, CD154, CDC27, CDK-4/m, CDKN2A, CXCR4, colon-specific antigen-p (CSAp), CEA (CEACAM5), CEACAM6, c-met, DAM, EGFR, EGFRvIII, EGP-1, EGP-2, ELF2-M, Ep-CAM, Flt-1, Flt-3, folate receptor, G250 antigen, GAGE, gp100, GROB, HLA-DR, HM1.24, human chorionic gonadotropin (HCG) and its subunits, HER2/neu, HMGB-1, hypoxia inducible factor (HIF-1), HSP70-2M, HST-2, Ia, IGF-1R, IFN-γ, IFN-α, IFN-β, IL-2, IL-4R, IL-6R, IL-13R, IL-15R, IL-17R, IL-18R, IL-6, IL-8, IL-12, IL-15, IL-17, IL-18, IL-25, insulin-like growth factor-1 (IGF-1), KC4-antigen, KS-1-antigen, KS1-4, Le-Y, LDR/FUT, macrophage migration inhibitory factor (MIF), MAGE, MAGE-3, MART-1, MART-2, NY-ESO-1, TRAG-3, mCRP, MCP-1, MIP-1A, MIP-1B, MIF, MUC1, MUC2, MUC3, MUC4, MUC5, MUM-1/2, MUM-3, NCA66, NCA95, NCA90, antigen specific for PAM-4 antibody, placental growth factor, p53, PLAGL2, prostatic acid phosphatase, PSA, PRAME, PSMA, PlGF, IGF, IGF-1R, IL-6, IL-25, RS5, RANTES, T101, SAGE, 5100, survivin, survivin-2B, TAC, TAG-72, tenascin, TRAIL receptors, TNF-α, Tn antigen, Thomson-Friedenreich antigens, tumor necrosis antigens, VEGFR, ED-B fibronectin, WT-1, 17-1A-antigen, complement factors C3, C3a, C3b, C5a, C5, an angiogenesis marker, bc1-2, bc1-6, Kras, cMET, an oncogene marker and an oncogene product (see, e.g., Sensi et al., Clin Cancer Res 2006, 12:5023-32; Parmiani et al., J Immunol 2007, 178:1975-79; Novellino et al. Cancer Immunol Immunother 2005, 54:187-207).

Exemplary antibodies that may be utilized include, but are not limited to, hR1 (anti-IGF-1R, U.S. patent application Ser. No. 12/722,645, filed Mar. 12, 2010), hPAM4 (anti-mucin, U.S. Pat. No. 7,282,567), hA20 (anti-CD20, U.S. Pat. No. 7,151,164), hA19 (anti-CD19, U.S. Pat. No. 7,109,304), hIMMU31 (anti-AFP, U.S. Pat. No. 7,300,655), hLL1 (anti-CD74, U.S. Pat. No. 7,312,318), hLL2 (anti-CD22, U.S. Pat. No. 5,789,554), hMu-9 (anti-CSAp, U.S. Pat. No. 7,387,772), hL243 (anti-HLA-DR, U.S. Pat. No. 7,612,180), hMN-14 (anti-CEACAM5, U.S. Pat. No. 6,676,924), hMN-15 (anti-CEACAM6, U.S. Pat. No. 8,287,865), hRS7 (anti-EGP-1, U.S. Pat. No. 7,238,785) and hMN-3 (anti-CEACAM6, U.S. Pat. No. 7,541,440) the Examples section of each cited patent or application incorporated herein by reference.

An antibody or antigen-binding fragment of use may be chimeric, humanized or human. The use of chimeric antibodies is preferred to the parent murine antibodies because they possess human antibody constant region sequences and therefore do not elicit as strong a human anti-mouse antibody (HAMA) response as murine antibodies. The use of humanized antibodies is even more preferred, in order to further reduce the possibility of inducing a HAMA reaction. As discussed below, techniques for humanization of murine antibodies by replacing murine framework and constant region sequences with corresponding human antibody framework and constant region sequences are well known in the art and have been applied to numerous murine anti-cancer antibodies. Antibody humanization may also involve the substitution of one or more human framework amino acid residues with the corresponding residues from the parent murine framework region sequences. As also discussed below, techniques for production of human antibodies are also well known.

In certain preferred embodiments the targeted delivery complex may be produced using the dock-and-lock (DNL) technique (see, e.g., U.S. Pat. Nos. 7,550,143; 7,521,056; 7,534,866; 7,527,787 and 7,666,400, the Examples section of each incorporated herein by reference). The DNL technique utilizes the specific binding interactions occurring between a dimerization and docking domain (DDD moiety)

from protein kinase A, and an anchoring domain (AD moiety) from any of a number of known A-kinase anchoring proteins (AKAPs). The DDD moieties spontaneously form dimers which then bind to an AD moiety. By attaching appropriate effector moieties, such as antibodies or fragments thereof and siRNA carriers, to AD and DDD moieties, the DNL technique allows the specific covalent formation of any desired targeted delivery complex. Where the effector moiety is a protein or peptide, such as an antibody fragment, protamine or polylysine, the AD and DDD moieties may be incorporated into fusion proteins conjugated to the effector moieties. Where non-protein effector moieties are utilized, chemical conjugation may be utilized to attach the AD or DDD moiety.

In certain embodiments, disease therapy by targeted delivery of siRNA may be enhanced by combination therapy with one or more other therapeutic agents. Known therapeutic agents of use include toxins, immunomodulators (such as cytokines, lymphokines, chemokines, growth factors and tumor necrosis factors), hormones, hormone antagonists, enzymes, oligonucleotides (such as siRNA or RNAi), photoactive therapeutic agents, anti-angiogenic agents and pro-apoptotic agents. The therapeutic agents may be delivered by conjugation to the same or different antibodies or other targeting molecules or may be administered in unconjugated form. Other therapeutic agents may be administered before, concurrently with or after the siRNA targeted delivery complex.

In a preferred embodiment, the therapeutic agent is a cytotoxic agent, such as a drug or a toxin. Also preferred, the drug is selected from the group consisting of nitrogen mustards, ethylenimine derivatives, alkyl sulfonates, nitrosoureas, gemcitabine, triazenes, folic acid analogs, anthracyclines, taxanes, COX-2 inhibitors, pyrimidine analogs, purine analogs, antibiotics, enzyme inhibitors, epipodophyllotoxins, platinum coordination complexes, vinca alkaloids, substituted ureas, methyl hydrazine derivatives, adrenocortical suppressants, hormone antagonists, endostatin, taxols, camptothecins, SN-38, doxorubicins and their analogs, antimetabolites, alkylating agents, antimitotics, anti-angiogenic agents, tyrosine kinase inhibitors, mTOR inhibitors, heat shock protein (HSP90) inhibitors, proteosome inhibitors, HDAC inhibitors, pro-apoptotic agents, methotrexate, CPT-11, calicheamicin and a combination thereof.

In another preferred embodiment, the therapeutic agent is a toxin selected from the group consisting of ricin, abrin, alpha toxin, saporin, ribonuclease (RNase), DNase I, Staphylococcal enterotoxin-A, pokeweed antiviral protein, gelonin, diphtheria toxin, *Pseudomonas* exotoxin, and *Pseudomonas* endotoxin and combinations thereof. Or an immunomodulator selected from the group consisting of a cytokine, a stem cell growth factor, a lymphotoxin, a hematopoietic factor, a colony stimulating factor (CSF), an interferon (IFN), erythropoietin, thrombopoietin and a combinations thereof.

In other preferred embodiments, the therapeutic agent is a radionuclide selected from the group consisting of $^{111}$In, $^{177}$Lu, $^{212}$Bi, $^{213}$Bi, $^{211}$At, $^{62}$Cu, $^{67}$Cu, $^{90}$Y, $^{125}$I, $^{131}$I, $^{32}$P, $^{33}$P, $^{47}$Sc, $^{111}$Ag, $^{67}$Ga, $^{142}$Pr, $^{153}$Sm, $^{161}$Tb, $^{166}$Dy, $^{166}$Ho, $^{186}$Re, $^{188}$Re, $^{189}$Re, $^{212}$Pb, $^{223}$Ra, $^{225}$Ac, $^{59}$Fe, $^{75}$Se, $^{77}$As, $^{89}$Mo, $^{99}$Mo, $^{105}$Rh, $^{109}$Pd, $^{143}$Pr, $^{149}$Pm, $^{169}$Er, $^{194}$Ir, $^{198}$Au, $^{199}$Au, and $^{211}$Pb. Also preferred are radionuclides that substantially decay with Auger-emitting particles. For example, Co-58, Ga-67, Br-80m, Tc-99m, Rh-103m, Pt-109, In-111, Sb-119, I-125, Ho-161, Os-189m and Ir-192. Decay energies of useful beta-particle-emitting nuclides are preferably <1,000 keV, more preferably <100 keV, and most preferably <70 keV. Also preferred are radionuclides that substantially decay with generation of alpha-particles. Such radionuclides include, but are not limited to: Dy-152, At-211, Bi-212, Ra-223, Rn-219, Po-215, Bi-211, Ac-225, Fr-221, At-217, Bi-213 and Fm-255. Decay energies of useful alpha-particle-emitting radionuclides are preferably 2,000-10,000 keV, more preferably 3,000-8,000 keV, and most preferably 4,000-7,000 keV. Additional potential radioisotopes of use include $^{11}$C, $^{13}$N, $^{15}$O, $^{75}$Br, $^{198}$Au, $^{224}$Ac, $^{126}$I, $^{133}$I, $^{77}$Br, $^{113m}$In, $^{95}$Ru, $^{97}$Ru, $^{103}$Ru, $^{105}$Ru, $^{107}$Hg, $^{203}$Hg, $^{121m}$Te, $^{122m}$Te, $^{125}$Te, $^{165}$Tm, $^{167}$Tm, $^{168}$Tm, $^{197}$Pt, $^{109}$Pd, $^{105}$Rh, $^{142}$Pr, $^{143}$Pr, $^{161}$Tb, $^{166}$Ho, $^{199}$Au, $^{57}$Co, $^{58}$Co, $^{51}$Cr, $^{59}$Fe, $^{75}$Se, $^{201}$Tl, $^{225}$Ac, $^{76}$Br, $^{169}$Yb, and the like. In other embodiments the therapeutic agent is a photoactive therapeutic agent selected from the group consisting of chromogens and dyes.

Alternatively, the therapeutic agent is an enzyme selected from the group consisting of malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. Such enzymes may be used, for example, in combination with prodrugs that are administered in relatively non-toxic form and converted at the target site by the enzyme into a cytotoxic agent. In other alternatives, a drug may be converted into less toxic form by endogenous enzymes in the subject but may be reconverted into a cytotoxic form by the therapeutic enzyme.

DETAILED DESCRIPTION

Definitions

Figure 1:
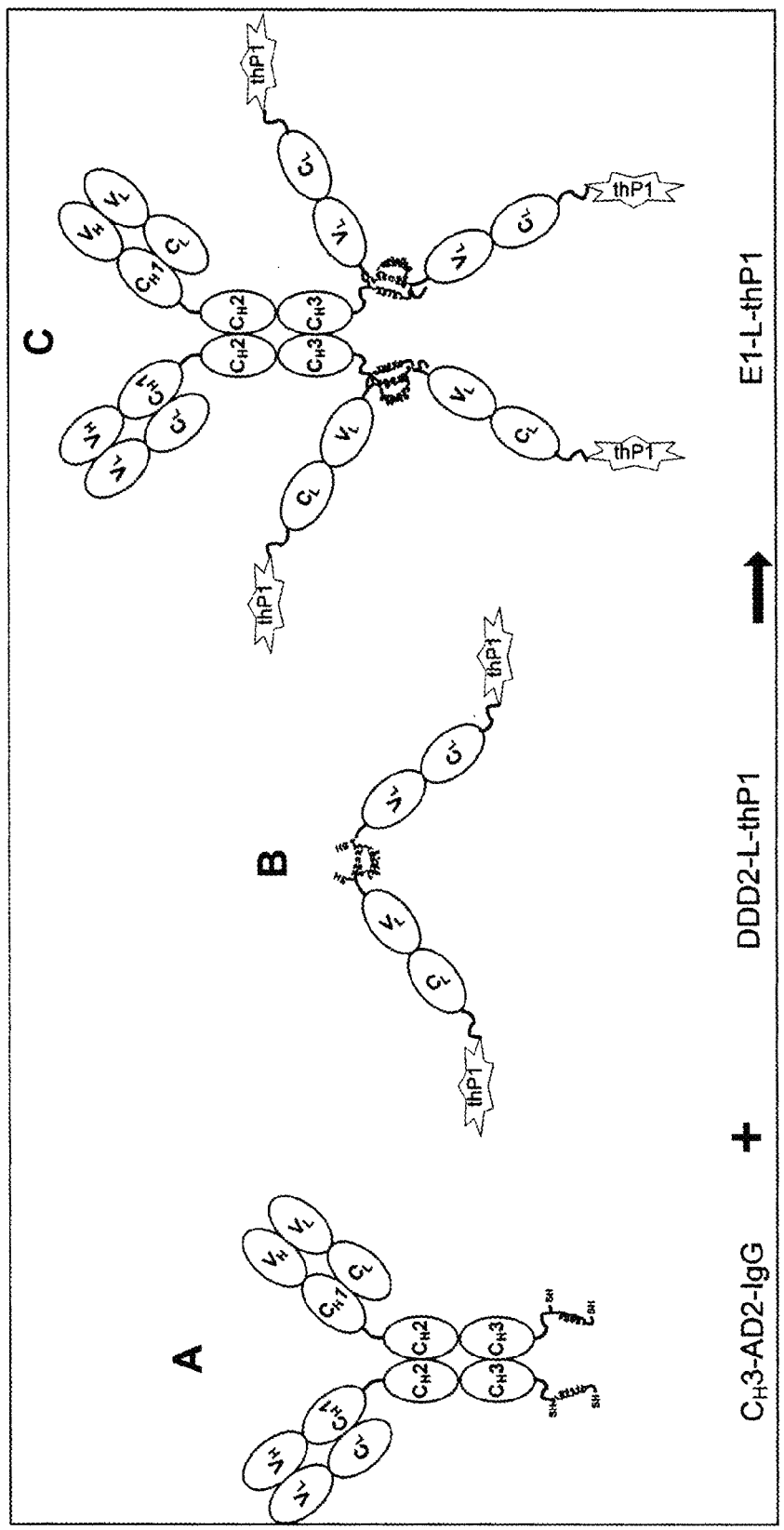
FIG. 1. Synthesis of E1-L-thP1 DNL complex for siRNA delivery. (A) An anti-Trop-2 hRS7 antibody was produced with an AD2 moiety attached to the C-terminal end of each antibody heavy chain. (B) A DDD2-L-thP1 construct was synthesized with a truncated segment of human protamine 1 and a DDD2 moiety attached respectively to the C- and N-terminal ends of a humanized antibody light chain. (C) Incubation of the hRS7-IgG-AD2 and DDD2-L-thP1 under mild reducing conditions resulted in the formation of the protamine-conjugated hRS7 DNL complex, designated E1-L-thP1.

Unless otherwise specified, "a" or "an" means one or more.

As used herein, "about" means plus or minus 10%. For example, "about 100" would include any number between 90 and 110.

An antibody, as described herein, refers to a full-length (i.e., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment.

An antibody fragment is a portion of an antibody such as F(ab')₂, Fab', Fab, Fv, sFv and the like. Regardless of structure, an antibody fragment binds with the same antigen that is recognized by the full-length antibody. The term "antibody fragment" also includes isolated fragments consisting of the variable regions of antibodies, such as the "Fv" fragments consisting of the variable regions of the heavy and light chains and recombinant single chain polypeptide molecules in which light and heavy variable regions are connected by a peptide linker ("scFv proteins").

A chimeric antibody is a recombinant protein that contains the variable domains including the complementarity determining regions (CDRs) of an antibody derived from one species, preferably a rodent antibody, while the constant domains of the antibody molecule are derived from those of a human antibody. For veterinary applications, the constant domains of the chimeric antibody may be derived from that of other species, such as a cat or dog.

A humanized antibody is a recombinant protein in which the CDRs from an antibody from one species; e.g., a rodent antibody, are transferred from the heavy and light variable chains of the rodent antibody into human heavy and light variable domains (e.g., framework region sequences). The constant domains of the antibody molecule are derived from those of a human antibody. In certain embodiments, a limited number of framework region amino acid residues from the parent (rodent) antibody may be substituted into the human antibody framework region sequences.

A human antibody is, e.g., an antibody obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous murine heavy chain and light chain loci. The transgenic mice can synthesize human antibodies specific for particular antigens, and the mice can be used to produce human antibody-secreting hybridomas. Methods for obtaining human antibodies from transgenic mice are described by Green et al., Nature Genet. 7:13 (1994), Lonberg et al., Nature 368:856 (1994), and Taylor et al., Int. Immun. 6:579 (1994). A fully human antibody also can be constructed by genetic or chromosomal transfection methods, as well as phage display technology, all of which are known in the art. See for example, McCafferty et al., Nature 348:552-553 (1990) for the production of human antibodies and fragments thereof in vitro, from immunoglobulin variable domain gene repertoires from unimmunized donors. In this technique, antibody variable domain genes are cloned in-frame into either a major or minor coat protein gene of a filamentous bacteriophage, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. In this way, the phage mimics some of the properties of the B-cell. Phage display can be performed in a variety of formats, for review, see e.g. Johnson and Chiswell, Current Opinion in Structural Biology 3:5564-571 (1993). Human antibodies may also be generated by in vitro activated B-cells. See U.S. Pat. Nos. 5,567,610 and 5,229,275, the Examples section of which is incorporated herein by reference.

A therapeutic agent is a compound, molecule or atom which is administered separately, concurrently or sequentially with an antibody moiety or conjugated to an antibody moiety, i.e., antibody or antibody fragment, or a subfragment, and is useful in the treatment of a disease. Examples of therapeutic agents include antibodies, antibody fragments, drugs, toxins, nucleases, hormones, immunomodulators, pro-apoptotic agents, anti-angiogenic agents, boron compounds, photoactive agents or dyes and radioisotopes. Therapeutic agents of use are described in more detail below.

An immunoconjugate is an antibody, antibody fragment or fusion protein conjugated to at least one therapeutic and/or diagnostic agent.

Interference RNA

The skilled artisan will realize that any siRNA or interference RNA species may be attached to the targeted delivery complexes for delivery to a targeted tissue. Many siRNA species against a wide variety of targets are known in the art, and any such known siRNA may be utilized in the claimed methods and compositions.

Known siRNA species of potential use include those specific for IKK-gamma (U.S. Pat. No. 7,022,828); VEGF, Flt-1 and Flk-1/KDR (U.S. Pat. No. 7,148,342); Bcl2 and EGFR (U.S. Pat. No. 7,541,453); CDC20 (U.S. Pat. No. 7,550,572); transducin (beta)-like 3 (U.S. Pat. No. 7,576,196); KRAS (U.S. Pat. No. 7,576,197); carbonic anhydrase II (U.S. Pat. No. 7,579,457); complement component 3 (U.S. Pat. No. 7,582,746); interleukin-1 receptor-associated kinase 4 (IRAK4) (U.S. Pat. No. 7,592,443); survivin (U.S. Pat. No. 7,608,7070); superoxide dismutase 1 (U.S. Pat. No. 7,632,938); MET proto-oncogene (U.S. Pat. No. 7,632,939); amyloid beta precursor protein (APP) (U.S. Pat. No. 7,635,771); IGF-1R (U.S. Pat. No. 7,638,621); ICAM1 (U.S. Pat. No. 7,642,349); complement factor B (U.S. Pat. No. 7,696,344); p53 (U.S. Pat. No. 7,781,575), and apolipoprotein B (U.S. Pat. No. 7,795,421), the Examples section of each referenced patent incorporated herein by reference.

Additional siRNA species are available from known commercial sources, such as Sigma-Aldrich (St Louis, Mo.), Invitrogen (Carlsbad, Calif.), Santa Cruz Biotechnology (Santa Cruz, Calif.), Ambion (Austin, Tex.), Dharmacon (Thermo Scientific, Lafayette, Colo.), Promega (Madison, Wis.), Mirus Bio (Madison, Wis.) and Qiagen (Valencia, Calif.), among many others. Other publicly available sources of siRNA species include the siRNAdb database at the Stockholm Bioinformatics Centre, the MIT/ICBP siRNA Database, the RNAi Consortium shRNA Library at the Broad Institute, and the Probe database at NCBI. For example, there are 30,852 siRNA species in the NCBI Probe database. The skilled artisan will realize that for any gene of interest, either a siRNA species has already been designed, or one may readily be designed using publicly available software tools. Any such siRNA species may be delivered using the subject DNL complexes.

Exemplary siRNA species known in the art are listed in Table 1. Although siRNA is delivered as a double-stranded molecule, for simplicity only the sense strand sequences are shown in Table 1.

TABLE 1

Exemplary siRNA Sequences

| Target | Sequence | SEQ ID NO |
|---|---|---|
| VEGF R2 | AATGCGGCGGTGGTGACAGTA | SEQ ID NO: 1 |
| VEGF R2 | AAGCTCAGCACACAGAAAGAC | SEQ ID NO: 2 |
| CXCR4 | UAAAAUCUUCCUGCCCACCdTdT | SEQ ID NO: 3 |
| CXCR4 | GGAAGCUGUUGGCUGAAAAdTdT | SEQ ID NO: 4 |
| PPARC1 | AAGACCAGCCUCUUUGCCCAG | SEQ ID NO: 5 |
| Dynamin 2 | GGACCAGGCAGAAAACGAG | SEQ ID NO: 6 |
| Catenin | CUAUCAGGAUGACGCGG | SEQ ID NO: 7 |
| E1A binding protein | UGACACAGGCAGGCUUGACUU | SEQ ID NO: 8 |
| Plasminogen activator | GGTGAAGAAGGGCGTCCAA | SEQ ID NO: 9 |
| K-ras | GATCCGTTGGAGCTGTTGGCGTAGTT CAAGAGACTCGCCAACAGCTCCAACT TTTGGAAA | SEQ ID NO: 10 |
| Sortilin 1 | AGGTGGTGTTAACAGCAGAG | SEQ ID NO: 11 |
| Apolipoprotein E | AAGGTGGAGCAAGCGGTGGAG | SEQ ID NO: 12 |
| Apolipoprotein E | AAGGAGTTGAAGGCCGACAAA | SEQ ID NO: 13 |
| Bcl-X | UAUGGAGCUGCAGAGGAUGdTdT | SEQ ID NO: 14 |
| Raf-1 | TTTGAATATCTGTGCTGAGAACACA GTTCTCAGCACAGATATTCTTTTT | SEQ ID NO: 15 |
| Heat shock transcription factor 2 | AATGAGAAAAGCAAAAGGTGCCCTGTCTC | SEQ ID NO: 16 |
| IGFBP3 | AAUCAUCAUCAAGAAAGGGCA | SEQ ID NO: 17 |
| Thioredoxin | AUGACUGUCAGGAUGUUGCdTdT | SEQ ID NO: 18 |
| CD44 | GAACGAAUCCUGAAGACAUCU | SEQ ID NO: 19 |
| MMP14 | AAGCCTGGCTACAGCAATATGCCTGTCTC | SEQ ID NO: 20 |
| MAPKAPK2 | UGACCAUCACCGAGUUUAUdTdT | SEQ ID NO: 21 |
| FGFR1 | AAGTCGGACGCAACAGAGAAA | SEQ ID NO: 22 |
| ERBB2 | CUACCUUUCUACGGACGUGdTdT | SEQ ID NO: 23 |
| BCL2L1 | CTGCCTAAGGCGGATTTGAAT | SEQ ID NO: 24 |
| ABL1 | TTAUUCCUUCUUCGGGAAGUC | SEQ ID NO: 25 |
| CEACAM1 | AACCTTCTGGAACCCGCCCAC | SEQ ID NO: 26 |
| CD9 | GAGCATCTTCGAGCAAGAA | SEQ ID NO: 27 |
| CD151 | CATGTGGCACCGTTTGCCT | SEQ ID NO: 28 |
| Caspase 8 | AACTACCAGAAAGGTATACCT | SEQ ID NO: 29 |
| BRCA1 | UCACAGUGUCCUUUAUGUAdTdT | SEQ ID NO: 30 |
| p53 | GCAUGAACCGGAGGCCCAUTT | SEQ ID NO: 31 |
| CEACAM6 | CCGGACAGTTCCATGTATA | SEQ ID NO: 32 |

The skilled artisan will realize that Table 1 represents a very small sampling of the total number of siRNA species known in the art, and that any such known siRNA may be utilized in the claimed methods and compositions.

Antibody Preparation

In certain embodiments, the targeted delivery complex may comprise a monoclonal antibody (MAb) or antigen-binding antibody fragment. MAbs can be isolated and purified from hybridoma cultures by a variety of well-established techniques. Such isolation techniques include affinity chromatography with Protein-A or Protein-G Sepharose, size-exclusion chromatography, and ion-exchange chromatography. See, for example, Coligan at pages 2.7.1-2.7.12 and pages 2.9.1-2.9.3. Also, see Baines et al., "Purification of Immunoglobulin G (IgG)," in METHODS IN MOLECULAR BIOLOGY, VOL. 10, pages 79-104 (The Humana Press, Inc. 1992). After the initial raising of antibodies to the immunogen, the antibodies can be sequenced and subsequently prepared by recombinant techniques. Humanization and chimerization of murine antibodies and antibody fragments are well known to those skilled in the art, as discussed below.

Chimeric Antibodies

A chimeric antibody is a recombinant protein in which the variable regions of a human antibody have been replaced by the variable regions of, for example, a mouse antibody, including the complementarity-determining regions (CDRs) of the mouse antibody. Chimeric antibodies exhibit decreased immunogenicity and increased stability when administered to a subject. General techniques for cloning murine immunoglobulin variable domains are disclosed, for example, in Orlandi et al., *Proc. Nat'l Acad. Sci. USA* 6: 3833 (1989). Techniques for constructing chimeric antibodies are well known to those of skill in the art. As an example, Leung et al., *Hybridoma* 13:469 (1994), produced an LL2 chimera by combining DNA sequences encoding the $V_\kappa$ and $V_H$ domains of murine LL2, an anti-CD22 monoclonal antibody, with respective human κ and $IgG_1$ constant region domains.

Humanized Antibodies

Techniques for producing humanized MAbs are well known in the art (see, e.g., Jones et al., *Nature* 321: 522 (1986), Riechmann et al., *Nature* 332: 323 (1988), Verhoeyen et al., *Science* 239: 1534 (1988), Carter et al., *Proc. Nat'l Acad. Sci. USA* 89: 4285 (1992), Sandhu, *Crit. Rev. Biotech.* 12: 437 (1992), and Singer et al., *J. Immun.* 150: 2844 (1993)). A chimeric or murine monoclonal antibody may be humanized by transferring the mouse CDRs from the heavy and light variable chains of the mouse immunoglobulin into the corresponding variable domains of a human antibody. The mouse framework regions (FR) in the chimeric monoclonal antibody are also replaced with human FR sequences. As simply transferring mouse CDRs into human H is often results in a reduction or even loss of antibody affinity, additional modification might be required in order to restore the original affinity of the murine antibody. This can be accomplished by the replacement of one or more human residues in the FR regions with their murine counterparts to obtain an antibody that possesses good binding affinity to its epitope. See, for example, Tempest et al., *Biotechnology* 9:266 (1991) and Verhoeyen et al., *Science* 239: 1534 (1988). Preferred residues for substitution include FR residues that are located within 1, 2, or 3 Angstroms of a CDR residue side chain, that are located adjacent to a CDR sequence, or that are predicted to interact with a CDR residue.

Human Antibodies

Methods for producing fully human antibodies using either combinatorial approaches or transgenic animals transformed with human immunoglobulin loci are known in the art (e.g., Mancini et al., 2004, *New Microbiol.* 27:315-28; Conrad and Scheller, 2005, *Comb. Chem. High Throughput Screen.* 8:117-26; Brekke and Loset, 2003, *Curr. Opin. Pharmacol.* 3:544-50). A fully human antibody also can be constructed by genetic or chromosomal transfection methods, as well as phage display technology, all of which are known in the art. See for example, McCafferty et al., *Nature* 348:552-553 (1990). Such fully human antibodies are expected to exhibit even fewer side effects than chimeric or humanized antibodies and to function in vivo as essentially endogenous human antibodies.

In one alternative, the phage display technique may be used to generate human antibodies (e.g., Dantas-Barbosa et al., 2005, *Genet. Mol. Res.* 4:126-40). Human antibodies may be generated from normal humans or from humans that exhibit a particular disease state, such as cancer (Dantas-Barbosa et al., 2005). The advantage to constructing human antibodies from a diseased individual is that the circulating antibody repertoire may be biased towards antibodies against disease-associated antigens.

In one non-limiting example of this methodology, Dantas-Barbosa et al. (2005) constructed a phage display library of human Fab antibody fragments from osteosarcoma patients. Generally, total RNA was obtained from circulating blood lymphocytes (Id.). Recombinant Fab were cloned from the μ, γ and κ chain antibody repertoires and inserted into a phage display library (Id.). RNAs were converted to cDNAs and used to make Fab cDNA libraries using specific primers against the heavy and light chain immunoglobulin sequences (Marks et al., 1991, *J. Mol. Biol.* 222:581-97). Library construction was performed according to Andris-Widhopf et al. (2000, In: *Phage Display Laboratory Manual*, Barbas et al. (eds), $1^{st}$ edition, Cold Spring Harbor Laboratory Press, Cold Spring Harbor, N.Y. pp. 9.1 to 9.22). The final Fab fragments were digested with restriction endonucleases and inserted into the bacteriophage genome to make the phage display library. Such libraries may be screened by standard phage display methods, as known in the art. Phage display can be performed in a variety of formats, for their review, see e.g. Johnson and Chiswell, *Current Opinion in Structural Biology* 3:5564-571 (1993).

Human antibodies may also be generated by in vitro activated B-cells. See U.S. Pat. Nos. 5,567,610 and 5,229,275, incorporated herein by reference in their entirety. The skilled artisan will realize that these techniques are exemplary and any known method for making and screening human antibodies or antibody fragments may be utilized.

In another alternative, transgenic animals that have been genetically engineered to produce human antibodies may be used to generate antibodies against essentially any immunogenic target, using standard immunization protocols. Methods for obtaining human antibodies from transgenic mice are disclosed by Green et al., *Nature Genet.* 7:13 (1994), Lonberg et al., *Nature* 368:856 (1994), and Taylor et al., *Int. Immun.* 6:579 (1994). A non-limiting example of such a system is the XenoMouse® (e.g., Green et al., 1999, *J. Immunol. Methods* 231:11-23, incorporated herein by reference) from Abgenix (Fremont, Calif.). In the XenoMouse® and similar animals, the mouse antibody genes have been inactivated and replaced by functional human antibody genes, while the remainder of the mouse immune system remains intact.

The XenoMouse® was transformed with germline-configured YACs (yeast artificial chromosomes) that contained portions of the human IgH and Igkappa loci, including the majority of the variable region sequences, along with accessory genes and regulatory sequences. The human variable region repertoire may be used to generate antibody producing B-cells, which may be processed into hybridomas by known techniques. A XenoMouse® immunized with a target antigen will produce human antibodies by the normal immune response, which may be harvested and/or produced by standard techniques discussed above. A variety of strains of XenoMouse® are available, each of which is capable of producing a different class of antibody. Transgenically produced human antibodies have been shown to have therapeutic potential, while retaining the pharmacokinetic properties of normal human antibodies (Green et al., 1999). The skilled artisan will realize that the claimed compositions and methods are not limited to use of the XenoMouse® system but may utilize any transgenic animal that has been genetically engineered to produce human antibodies.

Known Antibodies and Target Antigens

As discussed above, in preferred embodiments the targeted delivery complexes are of use for treatment of malignant disease, cardiovascular disease, infectious disease, inflammatory disease, autoimmune disease, metabolic disease, immune dysfunction disease (e.g., graft versus host disease or organ transplant rejection) or neurological (e.g., neurodegenerative) disease. Exemplary target antigens of use for treating such diseases may include carbonic anhydrase IX, CCL19, CCL21, CSAp, CD1, CD1a, CD2, CD3, CD4, CD5, CD8, CD11A, CD14, CD15, CD16, CD18, CD19, IGF-1R, CD20, CD21, CD22, CD23, CD25, CD29, CD30, CD32b, CD33, CD37, CD38, CD40, CD40L, CD45, CD46, CD52, CD54, CD55, CD59, CD64, CD66a-e, CD67, CD70, CD74, CD79a, CD80, CD83, CD95, CD126, CD133, CD138, CD147, CD154, CXCR4, CXCR7, CXCL12, HIF-1a, AFP, PSMA, CEACAM5, CEACAM6, c-met, B7, ED-B of fibronectin, Factor H, FHL-1, Flt-3, folate receptor, GROB, HMGB-1, hypoxia inducible factor (HIF), HM1.24, insulin-like growth factor-1 (IGF-1), IFN-γ, IFN-α, IFN-β, IL-2, IL-4R, IL-6R, IL-13R, IL-15R, IL-17R, IL-18R, IL-6, IL-8, IL-12, IL-15, IL-17, IL-18, IL-25, IP-10, MAGE, mCRP, MCP-1, MIP-1A, MIP-1B, MIF, MUC1, MUC2, MUC3, MUC4, MUC5, NCA-95, NCA-90, Ia, HM1.24, EGP-1, EGP-2, HLA-DR, tenascin, Le(y), RANTES, T101, TAC, Tn antigen, Thomson-Friedenreich antigens, tumor necrosis antigens, TNF-α, TRAIL receptor (R1 and R2), VEGFR, EGFR, PlGF, complement factors C3, C3a, C3b, C5a, C5, PLAGL2, and an oncogene product.

In certain embodiments, such as treating tumors, antibodies of use may target tumor-associated antigens. These antigenic markers may be substances produced by a tumor or may be substances which accumulate at a tumor site, on tumor cell surfaces or within tumor cells. Among such tumor-associated markers are those disclosed by Herberman, "Immunodiagnosis of Cancer", in Fleisher ed., "The Clinical Biochemistry of Cancer", page 347 (American Association of Clinical Chemists, 1979) and in U.S. Pat. Nos. 4,150,149; 4,361,544; and 4,444,744, the Examples section of each of which is incorporated herein by reference. Reports on tumor associated antigens (TAAs) include Mizukami et al., (2005, *Nature Med.* 11:992-97); Hatfield et al., (2005, *Curr. Cancer Drug Targets* 5:229-48); Vallbohmer et al. (2005, *J. Clin. Oncol.* 23:3536-44); and Ren et al. (2005, *Ann. Surg.* 242:55-63), each incorporated herein by reference with respect to the TAAs identified.

Tumor-associated markers have been categorized by Herberman, supra, in a number of categories including oncofetal antigens, placental antigens, oncogenic or tumor virus associated antigens, tissue associated antigens, organ associated antigens, ectopic hormones and normal antigens or variants thereof. Occasionally, a sub-unit of a tumor-associated marker is advantageously used to raise antibodies having higher tumor-specificity, e.g., the beta-subunit of human chorionic gonadotropin (HCG) or the gamma region of carcinoembryonic antigen (CEA), which stimulate the production of antibodies having a greatly reduced cross-reactivity to non-tumor substances as disclosed in U.S. Pat. Nos. 4,361,644 and 4,444,744.

Another marker of interest is transmembrane activator and CAML-interactor (TACT). See Yu et al. Nat. Immunol. 1:252-256 (2000). Briefly, TACI is a marker for B-cell malignancies (e.g., lymphoma). TACI and B-cell maturation antigen (BCMA) are bound by the tumor necrosis factor homolog—a proliferation-inducing ligand (APRIL). APRIL stimulates in vitro proliferation of primary B and T-cells and increases spleen weight due to accumulation of B-cells in vivo. APRIL also competes with TALL-I (also called BLyS or BAFF) for receptor binding. Soluble BCMA and TACI specifically prevent binding of APRIL and block APRIL-stimulated proliferation of primary B-cells. BCMA-Fc also inhibits production of antibodies against keyhole limpet hemocyanin and Pneumovax in mice, indicating that APRIL and/or TALL-I signaling via BCMA and/or TACI are required for generation of humoral immunity. Thus, APRIL-TALL-I and BCMA-TACI form a two ligand-two receptor pathway involved in stimulation of B and T-cell function.

Where the disease involves a lymphoma, leukemia or autoimmune disorder, targeted antigens may be selected from the group consisting of CD4, CD5, CD8, CD14, CD15, CD19, CD20, CD21, CD22, CD23, CD25, CD33, CD37, CD38, CD40, CD40L, CD46, CD52, CD54, CD67, CD74, CD79a, CD80, CD126, CD138, CD154, CXCR4, B7, MUC1, Ia, Ii, HM1.24, HLA-DR, tenascin, VEGF, PlGF, ED-B fibronectin, an oncogene (e.g., c-met or PLAGL2), an oncogene product, CD66a-d, necrosis antigens, IL-2, T101, TAG, IL-6, MIF, TRAIL-R1 (DR4) and TRAIL-R2 (DR5).

The skilled artisan will realize that any antibody or fragment known in the art that has binding specificity for a target antigen associated with a disease state or condition may be utilized. Such known antibodies include, but are not limited to, hR1 (anti-IGF-1R, U.S. patent application Ser. No. 12/772,645, filed Mar. 12, 2010) hPAM4 (anti-pancreatic cancer mucin, U.S. Pat. No. 7,282,567), hA20 (anti-CD20, U.S. Pat. No. 7,151,164), hA19 (anti-CD19, U.S. Pat. No. 7,109,304), hIMMU31 (anti-AFP, U.S. Pat. No. 7,300, 655), hLL1 (anti-CD74, U.S. Pat. No. 7,312,318), hLL2 (anti-CD22, U.S. Pat. No. 5,789,554), hMu-9 (anti-CSAp, U.S. Pat. No. 7,387,772), hL243 (anti-HLA-DR, U.S. Pat. No. 7,612,180), hMN-14 (anti-CEACAM5, U.S. Pat. No. 6,676,924), hMN-15 (anti-CEACAM6, U.S. Pat. No. 7,662, 378, U.S. patent application Ser. No. 12/846,062, filed Jul. 29, 2010, now issued U.S. Pat. No. 8,287,865), hRS7 (anti-EGP-1, U.S. Pat. No. 7,238,785), hMN-3 (anti-CEACAM6, U.S. Pat. No. 7,541,440), Ab124 and Ab125 (anti-CXCR4, U.S. Pat. No. 7,138,496) the Examples section of each cited patent or application incorporated herein by reference.

Various other antibodies of use are known in the art (e.g., U.S. Pat. Nos. 5,686,072; 5,874,540; 6,107,090; 6,183,744; 6,306,393; 6,653,104; 6,730,300; 6,899,864; 6,926,893; 6,962,702; 7,074,403; 7,230,084; 7,238,785; 7,238,786; 7,256,004; 7,282,567; 7,300,655; 7,312,318; 7,585,491; 7,612,180; 7,642,239 and U.S. Patent Application Publ. No. 20060193865; each incorporated herein by reference.)

Antibodies of use may be commercially obtained from a wide variety of known sources. For example, a variety of antibody secreting hybridoma lines are available from the American Type Culture Collection (ATCC, Manassas, Va.). A large number of antibodies against various disease targets, including but not limited to tumor-associated antigens, have been deposited at the ATCC and/or have published variable region sequences and are available for use in the claimed methods and compositions. See, e.g., U.S. Pat. Nos. 7,312,318; 7,282,567; 7,151,164; 7,074,403; 7,060,802; 7,056,509; 7,049,060; 7,045,132; 7,041,803; 7,041,802; 7,041,293; 7,038,018; 7,037,498; 7,012,133; 7,001,598; 6,998,468; 6,994,976; 6,994,852; 6,989,241; 6,974,863; 6,965,018; 6,964,854; 6,962,981; 6,962,813; 6,956,107; 6,951,924; 6,949,244; 6,946,129; 6,943,020; 6,939,547; 6,921,645; 6,921,645; 6,921,533; 6,919,433; 6,919,078; 6,916,475; 6,905,681; 6,899,879; 6,893,625; 6,887,468; 6,887,466; 6,884,594; 6,881,405; 6,878,812; 6,875,580; 6,872,568; 6,867,006; 6,864,062; 6,861,511; 6,861,227; 6,861,226; 6,838,282; 6,835,549; 6,835,370; 6,824,780; 6,824,778; 6,812,206; 6,793,924; 6,783,758; 6,770,450; 6,767,711; 6,764,688; 6,764,681; 6,764,679; 6,743,898; 6,733,981; 6,730,307; 6,720,155; 6,716,966; 6,709,653; 6,693,176; 6,692,908; 6,689,607; 6,689,362; 6,689,355; 6,682,737; 6,682,736; 6,682,734; 6,673,344; 6,653,104; 6,652,852; 6,635,482; 6,630,144; 6,610,833; 6,610,294; 6,605,441; 6,605,279; 6,596,852; 6,592,868; 6,576,745; 6,572,856; 6,566,076; 6,562,618; 6,545,130; 6,544,749; 6,534,058; 6,528,625; 6,528,269; 6,521,227; 6,518,404; 6,511,665; 6,491,915; 6,488,930; 6,482,598; 6,482,408; 6,479,247; 6,468,531; 6,468,529; 6,465,173; 6,461,823; 6,458,356; 6,455,044; 6,455,040; 6,451,310; 6,444,206, 6,441,143; 6,432,404; 6,432,402; 6,419,928; 6,413,726; 6,406,694; 6,403,770; 6,403,091; 6,395,276; 6,395,274; 6,387,350; 6,383,759; 6,383,484; 6,376,654; 6,372,215; 6,359,126; 6,355,481; 6,355,444; 6,355,245; 6,355,244; 6,346,246; 6,344,198; 6,340,571; 6,340,459; 6,331,175; 6,306,393; 6,254,868; 6,187,287; 6,183,744; 6,129,914; 6,120,767; 6,096,289; 6,077,499; 5,922,302; 5,874,540; 5,814,440; 5,798,229; 5,789,554; 5,776,456; 5,736,119; 5,716,595; 5,677,136; 5,587,459; 5,443,953, 5,525,338. These are exemplary only and a wide variety of other antibodies and their hybridomas are known in the art. The skilled artisan will realize that antibody sequences or antibody-secreting hybridomas against almost any disease-associated antigen may be obtained by a simple search of the ATCC, NCBI and/or USPTO databases for antibodies against a selected disease-associated target of interest. The antigen binding domains of the cloned antibodies may be amplified, excised, ligated into an expression vector, transfected into an adapted host cell and used for protein production, using standard techniques well known in the art.

Antibody Fragments

Antibody fragments are antigen binding portions of an antibody, such as $F(ab')_2$, Fab', $F(ab)_2$, Fab, Fv, sFv, scFv and the like. Antibody fragments which recognize specific epitopes can be generated by known techniques. $F(ab')_2$ fragments, for example, can be produced by pepsin digestion of the antibody molecule. These and other methods are described, for example, by Goldenberg, U.S. Pat. Nos. 4,036,945 and 4,331,647 and references contained therein. Also, see Nisonoff et al., Arch Biochem. Biophys. 89: 230 (1960); Porter, Biochem. J. 73: 119 (1959), Edelman et al., in METHODS IN ENZYMOLOGY VOL. 1, page 422 (Academic Press 1967), and Coligan at pages 2.8.1-2.8.10 and 2.10.-2.10.4. Alternatively, Fab' expression libraries can be constructed (Huse et al., 1989, Science, 246:1274-1281) to allow rapid and easy identification of monoclonal Fab' fragments with the desired specificity.

A single chain Fv molecule (scFv) comprises a VL domain and a VH domain. The VL and VH domains associate to form a target binding site. These two domains are further covalently linked by a peptide linker (L). A scFv molecule is denoted as either VL-L-VH if the VL domain is the N-terminal part of the scFv molecule, or as VH-L-VL if the VH domain is the N-terminal part of the scFv molecule. Methods for making scFv molecules and designing suitable peptide linkers are described in U.S. Pat. No. 4,704,692, U.S. Pat. No. 4,946,778, R. Raag and M. Whitlow, "Single Chain Fvs." FASEB Vol 9:73-80 (1995) and R. E. Bird and B. W. Walker, Single Chain Antibody Variable Regions, TIBTECH, Vol 9: 132-137 (1991).

Other antibody fragments, for example single domain antibody fragments, are known in the art and may be used in the claimed constructs. Single domain antibodies (VHH) may be obtained, for example, from camels, alpacas or llamas by standard immunization techniques. (See, e.g., Muyldermans et al., TIBS 26:230-235, 2001; Yau et al., J Immunol Methods 281:161-75, 2003; Maass et al., J Immunol Methods 324:13-25, 2007). The VHH may have potent antigen-binding capacity and can interact with novel epitopes that are inaccessible to conventional VH-VL pairs. (Muyldermans et al., 2001). Alpaca serum IgG contains about 50% camelid heavy chain only IgG antibodies (HCAbs) (Maass et al., 2007). Alpacas may be immunized with known antigens, such as TNF-α, and VHHs can be isolated that bind to and neutralize the target antigen (Maass et al., 2007). PCR primers that amplify virtually all alpaca VHH coding sequences have been identified and may be used to construct alpaca VHH phage display libraries, which can be used for antibody fragment isolation by standard biopanning techniques well known in the art (Maass et al., 2007).

An antibody fragment can also be prepared by proteolytic hydrolysis of a full-length antibody or by expression in E. coli or another host of the DNA coding for the fragment. An antibody fragment can be obtained by pepsin or papain digestion of full-length antibodies by conventional methods. For example, an antibody fragment can be produced by enzymatic cleavage of antibodies with pepsin to provide an approximate 100 Kd fragment denoted $F(ab')_2$. This fragment can be further cleaved using a thiol reducing agent, and optionally a blocking group for the sulfhydryl groups resulting from cleavage of disulfide linkages, to produce an approximate 50 Kd Fab' monovalent fragment. Alternatively, an enzymatic cleavage using papain produces two monovalent Fab fragments and an Fc fragment directly.

Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody.

General Techniques for Antibody Cloning and Production

Various techniques, such as production of chimeric or humanized antibodies, may involve procedures of antibody cloning and construction. The antigen-binding V (variable light chain) and $V_H$ (variable heavy chain) sequences for an antibody of interest may be obtained by a variety of molecular cloning procedures, such as RT-PCR, 5'-RACE, and cDNA library screening. The V genes of a MAb from a cell that expresses a murine MAb can be cloned by PCR amplification and sequenced. To confirm their authenticity, the cloned $V_L$ and $V_H$ genes can be expressed in cell culture as a chimeric Ab as described by Orlandi et al., (Proc. Natl. Acad. Sci., USA, 86: 3833 (1989)). Based on the V gene sequences, a humanized MAb can then be designed and constructed as described by Leung et al. (Mol. Immunol., 32: 1413 (1995)).

cDNA can be prepared from any known hybridoma line or transfected cell line producing a murine MAb by general molecular cloning techniques (Sambrook et al., Molecular Cloning, A laboratory manual, 2$^{nd}$ Ed (1989)). The V sequence for the MAb may be amplified using the primers VK1BACK and VK1FOR (Orlandi et al., 1989) or the extended primer set described by Leung et al. (*BioTechniques*, 15: 286 (1993)). The V$_H$ sequences can be amplified using the primer pair VH1BACK/VH1FOR (Orlandi et al., 1989) or the primers annealing to the constant region of murine IgG described by Leung et al. (Hybridoma, 13:469 (1994)). Humanized V genes can be constructed by a combination of long oligonucleotide template syntheses and PCR amplification as described by Leung et al. (*Mol. Immunol.*, 32: 1413 (1995)).

PCR products for V can be subcloned into a staging vector, such as a pBR327-based staging vector, VKpBR, that contains an Ig promoter, a signal peptide sequence and convenient restriction sites. PCR products for V$_H$ can be subcloned into a similar staging vector, such as the pBluescript-based VHpBS. Expression cassettes containing the V and V$_H$ sequences together with the promoter and signal peptide sequences can be excised from VKpBR and VHpBS and ligated into appropriate expression vectors, such as pKh and pG1g, respectively (Leung et al., Hybridoma, 13:469 (1994)). The expression vectors can be co-transfected into an appropriate cell and supernatant fluids monitored for production of a chimeric, humanized or human MAb. Alternatively, the V and V$_H$ expression cassettes can be excised and subcloned into a single expression vector, such as pdHL2, as described by Gillies et al. (*J. Immunol. Methods* 125:191 (1989) and also shown in Losman et al., *Cancer*, 80:2660 (1997)).

In an alternative embodiment, expression vectors may be transfected into host cells that have been pre-adapted for transfection, growth and expression in serum-free medium. Exemplary cell lines that may be used include the Sp/EEE, Sp/ESF and Sp/ESF-X cell lines (see, e.g., U.S. Pat. Nos. 7,531,327; 7,537,930 and 7,608,425; the Examples section of each of which is incorporated herein by reference). These exemplary cell lines are based on the Sp2/0 myeloma cell line, transfected with a mutant Bcl-EEE gene, exposed to methotrexate to amplify transfected gene sequences and pre-adapted to serum-free cell line for protein expression.

Dock-and-Lock (DNL)

In certain embodiments, targeted delivery complexes may be produced using the dock-and-lock technology (see, e.g., U.S. Pat. Nos. 7,550,143; 7,521,056; 7,534,866; 7,527,787 and 7,666,400, the Examples section of each incorporated herein by reference). The DNL method exploits specific protein/protein interactions that occur between the regulatory (R) subunits of cAMP-dependent protein kinase (PKA) and the anchoring domain (AD) of A-kinase anchoring proteins (AKAPs) (Baillie et al., FEBS Letters. 2005; 579: 3264. Wong and Scott, Nat. Rev. Mol. Cell. Biol. 2004; 5: 959). PKA, which plays a central role in one of the best studied signal transduction pathways triggered by the binding of the second messenger cAMP to the R subunits, was first isolated from rabbit skeletal muscle in 1968 (Walsh et al., J. Biol. Chem. 1968; 243:3763). The structure of the holoenzyme consists of two catalytic subunits held in an inactive form by the R subunits (Taylor, J. Biol. Chem. 1989; 264:8443). Isozymes of PKA are found with two types of R subunits (RI and RII), and each type has α and β isoforms (Scott, Pharmacol. Ther. 1991; 50:123). The R subunits have been isolated only as stable dimers and the dimerization domain has been shown to consist of the first 44 amino-terminal residues (Newlon et al., Nat. Struct. Biol. 1999; 6:222). Binding of cAMP to the R subunits leads to the release of active catalytic subunits for a broad spectrum of serine/threonine kinase activities, which are oriented toward selected substrates through the compartmentalization of PKA via its docking with AKAPs (Scott et al., J. Biol. Chem. 1990; 265; 21561)

Since the first AKAP, microtubule-associated protein-2, was characterized in 1984 (Lohmann et al., Proc. Natl. Acad. Sci. USA. 1984; 81:6723), more than 50 AKAPs that localize to various sub-cellular sites, including plasma membrane, actin cytoskeleton, nucleus, mitochondria, and endoplasmic reticulum, have been identified with diverse structures in species ranging from yeast to humans (Wong and Scott, Nat. Rev. Mol. Cell. Biol. 2004; 5:959). The AD of AKAPs for PKA is an amphipathic helix of 14-18 residues (Carr et al., J. Biol. Chem. 1991; 266:14188). The amino acid sequences of the AD are quite varied among individual AKAPs, with the binding affinities reported for RII dimers ranging from 2 to 90 nM (Alto et al., Proc. Natl. Acad. Sci. USA. 2003; 100:4445). AKAPs will only bind to dimeric R subunits. For human RIIα, the AD binds to a hydrophobic surface formed by the 23 amino-terminal residues (Colledge and Scott, Trends Cell Biol. 1999; 6:216). Thus, the dimerization domain and AKAP binding domain of human RIIα are both located within the same N-terminal 44 amino acid sequence (Newlon et al., Nat. Struct. Biol. 1999; 6:222; Newlon et al., EMBO J. 2001; 20:1651), which is termed the DDD herein.

We have developed a platform technology to utilize the DDD of human RIIα and the AD of AKAP as an excellent pair of linker modules for docking any two entities, referred to hereafter as A and B, into a noncovalent complex, which could be further locked into a stably tethered structure through the introduction of cysteine residues into both the DDD and AD at strategic positions to facilitate the formation of disulfide bonds. The general methodology of the "dock-and-lock" approach is as follows. Entity A is constructed by linking a DDD sequence to a precursor of A, resulting in a first component hereafter referred to as a. Because the DDD sequence would effect the spontaneous formation of a dimer, A would thus be composed of $a_2$. Entity B is constructed by linking an AD sequence to a precursor of B, resulting in a second component hereafter referred to as b. The dimeric motif of DDD contained in $a_2$ will create a docking site for binding to the AD sequence contained in b, thus facilitating a ready association of $a_2$ and b to form a binary, trimeric complex composed of $a_2b$. This binding event is made irreversible with a subsequent reaction to covalently secure the two entities via disulfide bridges, which occurs very efficiently based on the principle of effective local concentration because the initial binding interactions should bring the reactive thiol groups placed onto both the DDD and AD into proximity (Chmura et al., Proc. Natl. Acad. Sci. USA. 2001; 98:8480) to ligate site-specifically. Using various combinations of linkers, adaptor modules and precursors, a wide variety of DNL constructs of different stoichiometry may be produced and used, including but not limited to dimeric, trimeric, tetrameric, pentameric and hexameric DNL constructs (see, e.g., U.S. Pat. Nos. 7,550,143; 7,521, 056; 7,534,866; 7,527,787 and 7,666,400.)

By attaching the DDD and AD away from the functional groups of the two precursors, such site-specific ligations are also expected to preserve the original activities of the two precursors. This approach is modular in nature and potentially can be applied to link, site-specifically and covalently, a wide range of substances, including peptides, proteins, antibodies, antibody fragments, and other effector moieties with a wide range of activities. Utilizing the fusion protein method of constructing AD and DDD conjugated effectors described in the Examples below, virtually any protein or peptide may be incorporated into a DNL construct. However, the technique is not limiting and other methods of conjugation may be utilized.

A variety of methods are known for making fusion proteins, including nucleic acid synthesis, hybridization and/or amplification to produce a synthetic double-stranded nucleic acid encoding a fusion protein of interest. Such double-stranded nucleic acids may be inserted into expression vectors for fusion protein production by standard molecular biology techniques (see, e.g. Sambrook et al., Molecular Cloning, A laboratory manual, $2^{nd}$ Ed, 1989). In such preferred embodiments, the AD and/or DDD moiety may be attached to either the N-terminal or C-terminal end of an effector protein or peptide. However, the skilled artisan will realize that the site of attachment of an AD or DDD moiety to an effector moiety may vary, depending on the chemical nature of the effector moiety and the part(s) of the effector moiety involved in its physiological activity. Site-specific attachment of a variety of effector moieties may be performed using techniques known in the art, such as the use of bivalent cross-linking reagents and/or other chemical conjugation techniques.

Immunoconjugates

In preferred embodiments, a moiety such as a siRNA carrier moiety may be covalently attached to an antibody or antibody fragment to form an immunoconjugate. Carrier moieties may be attached, for example to reduced SH groups and/or to carbohydrate side chains. A carrier moiety can be attached at the hinge region of a reduced antibody component via disulfide bond formation. Alternatively, such agents can be attached using a heterobifunctional cross-linker, such as N-succinyl 3-(2-pyridyldithio)propionate (SPDP). Yu et al., Int. J. Cancer 56: 244 (1994). General techniques for such conjugation are well-known in the art. See, for example, Wong, CHEMISTRY OF PROTEIN CONJUGATION AND CROSS-LINKING (CRC Press 1991); Upeslacis et al., "Modification of Antibodies by Chemical Methods," in MONOCLONAL ANTIBODIES: PRINCIPLES AND APPLICATIONS, Birch et al. (eds.), pages 187-230 (Wiley-Liss, Inc. 1995); Price, "Production and Characterization of Synthetic Peptide-Derived Antibodies," in MONOCLONAL ANTIBODIES: PRODUCTION, ENGINEERING AND CLINICAL APPLICATION, Ritter et al. (eds.), pages 60-84 (Cambridge University Press 1995). Alternatively, the carrier moiety can be conjugated via a carbohydrate moiety in the Fc region of the antibody.

Methods for conjugating functional groups to antibodies via an antibody carbohydrate moiety are well-known to those of skill in the art. See, for example, Shih et al., Int. J. Cancer 41: 832 (1988); Shih et al., Int. J. Cancer 46: 1101 (1990); and Shih et al., U.S. Pat. No. 5,057,313, the Examples section of which is incorporated herein by reference. The general method involves reacting an antibody having an oxidized carbohydrate portion with a carrier polymer that has at least one free amine function. This reaction results in an initial Schiff base (imine) linkage, which can be stabilized by reduction to a secondary amine to form the final conjugate.

The Fc region may be absent if the antibody component of the immunoconjugate is an antibody fragment. However, it is possible to introduce a carbohydrate moiety into the light chain variable region of a full length antibody or antibody fragment. See, for example, Leung et al., J. Immunol. 154: 5919 (1995); U.S. Pat. Nos. 5,443,953 and 6,254,868, the Examples section of which is incorporated herein by reference. The engineered carbohydrate moiety is used to attach the therapeutic or diagnostic agent.

An alternative method for attaching carrier moieties to a targeting molecule involves use of click chemistry reactions. The click chemistry approach was originally conceived as a method to rapidly generate complex substances by joining small subunits together in a modular fashion. (See, e.g., Kolb et al., 2004, Angew Chem Int Ed 40:3004-31; Evans, 2007, Aust J Chem 60:384-95.) Various forms of click chemistry reaction are known in the art, such as the Huisgen 1,3-dipolar cycloaddition copper catalyzed reaction (Tornoe et al., 2002, J Organic Chem 67:3057-64), which is often referred to as the "click reaction." Other alternatives include cycloaddition reactions such as the Diels-Alder, nucleophilic substitution reactions (especially to small strained rings like epoxy and aziridine compounds), carbonyl chemistry formation of urea compounds and reactions involving carbon-carbon double bonds, such as alkynes in thiol-yne reactions.

The azide alkyne Huisgen cycloaddition reaction uses a copper catalyst in the presence of a reducing agent to catalyze the reaction of a terminal alkyne group attached to a first molecule. In the presence of a second molecule comprising an azide moiety, the azide reacts with the activated alkyne to form a 1,4-disubstituted 1,2,3-triazole. The copper catalyzed reaction occurs at room temperature and is sufficiently specific that purification of the reaction product is often not required. (Rostovstev et al., 2002, Angew Chem Int Ed 41:2596; Tornoe et al., 2002, J Org Chem 67:3057.) The azide and alkyne functional groups are largely inert towards biomolecules in aqueous medium, allowing the reaction to occur in complex solutions. The triazole formed is chemically stable and is not subject to enzymatic cleavage, making the click chemistry product highly stable in biological systems. Although the copper catalyst is toxic to living cells, the copper-based click chemistry reaction may be used in vitro for immunoconjugate formation.

A copper-free click reaction has been proposed for covalent modification of biomolecules. (See, e.g., Agard et al., 2004, J Am Chem Soc 126:15046-47.) The copper-free reaction uses ring strain in place of the copper catalyst to promote a [3+2] azide-alkyne cycloaddition reaction (Id.) For example, cyclooctyne is an 8-carbon ring structure comprising an internal alkyne bond. The closed ring structure induces a substantial bond angle deformation of the acetylene, which is highly reactive with azide groups to form a triazole. Thus, cyclooctyne derivatives may be used for copper-free click reactions (Id.)

Another type of copper-free click reaction was reported by Ning et al. (2010, Angew Chem Int Ed 49:3065-68), involving strain-promoted alkyne-nitrone cycloaddition. To address the slow rate of the original cyclooctyne reaction, electron-withdrawing groups are attached adjacent to the triple bond (Id.) Examples of such substituted cyclooctynes include difluorinated cyclooctynes, 4-dibenzocyclooctynol and azacyclooctyne (Id.) An alternative copper-free reaction involved strain-promoted akyne-nitrone cycloaddition to give N-alkylated isoxazolines (Id.) The reaction was reported to have exceptionally fast reaction kinetics and was used in a one-pot three-step protocol for site-specific modification of peptides and proteins (Id.) Nitrons were prepared by the condensation of appropriate aldehydes with N-methylhydroxylamine and the cycloaddition reaction took place in a mixture of acetonitrile and water (Id.) These and other known click chemistry reactions may be used to attach carrier moieties to antibodies in vitro.

Methods of Therapeutic Treatment

Various embodiments concern methods of treating a cancer in a subject, comprising administering a therapeutically effective amount of a targeted delivery complex, such as an antibody conjugated to a siRNA carrier and loaded with siRNA moieties.

The targeted delivery complexes can be supplemented with the administration, either concurrently or sequentially, of at least one other therapeutic agent. Multimodal therapies may include therapy with other antibodies, such as anti-CD22, anti-CD19, anti-CD20, anti-CD21, anti-CD74, anti-CD80, anti-CD23, anti-CD45, anti-CD46, anti-MIF, anti-EGP-1, anti-CEACAM5, anti-CEACAM6, anti-pancreatic cancer mucin, anti-IGF-1R or anti-HLA-DR (including the invariant chain) antibodies in the form of naked antibodies, fusion proteins, or as immunoconjugates. Various antibodies of use, such as anti-CD19, anti-CD20, and anti-CD22 antibodies, are known to those of skill in the art. See, for example, Ghetie et al., *Cancer Res.* 48:2610 (1988); Hekman et al., *Cancer Immunol. Immunother.* 32:364 (1991); Longo, *Curr. Opin. Oncol.* 8:353 (1996), U.S. Pat. Nos. 5,798,554; 6,187,287; 6,306,393; 6,676,924; 7,109,304; 7,151,164; 7,230,084; 7,230,085; 7,238,785; 7,238,786; 7,282,567; 7,300,655; 7,312,318; 7,612,180; 7,501,498; the Examples section of each of which is incorporated herein by reference.

In another form of multimodal therapy, subjects receive targeted delivery complexes in conjunction with standard cancer chemotherapy. For example, "CVB" (1.5 g/m$^2$ cyclophosphamide, 200-400 mg/m$^2$ etoposide, and 150-200 mg/m$^2$ carmustine) is a regimen used to treat non-Hodgkin's lymphoma. Patti et al., *Eur. J. Haematol.* 51: 18 (1993). Other suitable combination chemotherapeutic regimens are well-known to those of skill in the art. See, for example, Freedman et al., "Non-Hodgkin's Lymphomas," in CANCER MEDICINE, VOLUME 2, 3rd Edition, Holland et al. (eds.), pages 2028-2068 (Lea & Febiger 1993). As an illustration, first generation chemotherapeutic regimens for treatment of intermediate-grade non-Hodgkin's lymphoma (NHL) include C-MOPP (cyclophosphamide, vincristine, procarbazine and prednisone) and CHOP (cyclophosphamide, doxorubicin, vincristine, and prednisone). A useful second generation chemotherapeutic regimen is m-BACOD (methotrexate, bleomycin, doxorubicin, cyclophosphamide, vincristine, dexamethasone and leucovorin), while a suitable third generation regimen is MACOP-B (methotrexate, doxorubicin, cyclophosphamide, vincristine, prednisone, bleomycin and leucovorin). Additional useful drugs include phenyl butyrate, bendamustine, and bryostatin-1.

In a preferred multimodal therapy, both chemotherapeutic drugs and cytokines are co-administered with a targeted delivery complex. The cytokines, chemotherapeutic drugs and targeted delivery complex can be administered in any order, or together.

Targeted delivery complexes can be formulated according to known methods to prepare pharmaceutically useful compositions, whereby the targeted delivery complex is combined in a mixture with a pharmaceutically suitable excipient. Sterile phosphate-buffered saline is one example of a pharmaceutically suitable excipient. Other suitable excipients are well-known to those in the art. See, for example, Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The targeted delivery complex of the present invention can be formulated for intravenous administration via, for example, bolus injection or continuous infusion. Preferably, the targeted delivery complex is infused over a period of less than about 4 hours, and more preferably, over a period of less than about 3 hours. For example, the first 25-50 mg could be infused within 30 minutes, preferably even 15 min, and the remainder infused over the next 2-3 hrs. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

The targeted delivery complex may also be administered to a mammal subcutaneously or even by other parenteral routes. Moreover, the administration may be by continuous infusion or by single or multiple boluses. Preferably, the targeted delivery complex is infused over a period of less than about 4 hours, and more preferably, over a period of less than about 3 hours.

More generally, the dosage of an administered targeted delivery complex for humans will vary depending upon such factors as the patient's age, weight, height, sex, general medical condition and previous medical history. It may be desirable to provide the recipient with a dosage of targeted delivery complex that is in the range of from about 1 mg/kg to 25 mg/kg as a single intravenous infusion, although a lower or higher dosage also may be administered as circumstances dictate. A dosage of 1-20 mg/kg for a 70 kg patient, for example, is 70-1,400 mg, or 41-824 mg/m$^2$ for a 1.7-m patient. The dosage may be repeated as needed, for example, once per week for 4-10 weeks, once per week for 8 weeks, or once per week for 4 weeks. It may also be given less frequently, such as every other week for several months, or monthly or quarterly for many months, as needed in a maintenance therapy.

Alternatively, a targeted delivery complex may be administered as one dosage every 2 or 3 weeks, repeated for a total of at least 3 dosages. Or, the targeted delivery complex may be administered twice per week for 4-6 weeks. If the dosage is lowered to approximately 200-300 mg/m$^2$ (340 mg per dosage for a 1.7-m patient, or 4.9 mg/kg for a 70 kg patient), it may be administered once or even twice weekly for 4 to 10 weeks. Alternatively, the dosage schedule may be decreased, namely every 2 or 3 weeks for 2-3 months. It has been determined, however, that even higher doses, such as 20 mg/kg once weekly or once every 2-3 weeks can be administered by slow i.v. infusion, for repeated dosing cycles. The dosing schedule can optionally be repeated at other intervals and dosage may be given through various parenteral routes, with appropriate adjustment of the dose and schedule.

In preferred embodiments, the subject targeted delivery complexes are of use for therapy of cancer. Examples of cancers include, but are not limited to, carcinoma, lymphoma, glioblastoma, melanoma, sarcoma, and leukemia, myeloma, or lymphoid malignancies. More particular examples of such cancers are noted below and include: squamous cell cancer (e.g., epithelial squamous cell cancer), Ewing sarcoma, Wilms tumor, astrocytomas, lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma multiforme, cervical cancer, ovarian cancer, liver cancer, bladder cancer, hepatoma, hepatocellular carcinoma, neuroendocrine tumors, medullary thyroid cancer, differentiated thyroid carcinoma, breast cancer, ovarian cancer, colon cancer, rectal cancer, endometrial cancer or uterine carcinoma, salivary gland carcinoma, kidney or renal cancer, prostate cancer, vulvar cancer, anal carcinoma, penile carcinoma, as well as head-and-neck cancer. The term "cancer" includes primary malignant cells or tumors (e.g., those whose cells have not migrated to sites in the subject's body other than the site of the original malignancy or tumor) and secondary malignant cells or tumors (e.g., those arising from metastasis, the migration of malignant cells or tumor cells to secondary sites that are different from the site of the original tumor).

Other examples of cancers or malignancies include, but are not limited to: Acute Childhood Lymphoblastic Leukemia, Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Lymphoma, Adult Lymphocytic Leukemia, Adult Non-Hodgkin's Lymphoma, Adult Primary Liver Cancer, Adult Soft Tissue Sarcoma, AIDS-Related Lymphoma, AIDS-Related Malignancies, Anal Cancer, Astrocytoma, Bile Duct Cancer, Bladder Cancer, Bone Cancer, Brain Stem Glioma, Brain Tumors, Breast Cancer, Cancer of the Renal Pelvis and Ureter, Central Nervous System (Primary) Lymphoma, Central Nervous System Lymphoma, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukemia, Childhood Acute Myeloid Leukemia, Childhood Brain Stem Glioma, Childhood Cerebellar Astrocytoma, Childhood Cerebral Astrocytoma, Childhood Extracranial Germ Cell Tumors, Childhood Hodgkin's Disease, Childhood Hodgkin's Lymphoma, Childhood Hypothalamic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumors, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T-Cell Lymphoma, Endocrine Pancreas Islet Cell Carcinoma, Endometrial Cancer, Ependymoma, Epithelial Cancer, Esophageal Cancer, Ewing's Sarcoma and Related Tumors, Exocrine Pancreatic Cancer, Extracranial Germ Cell Tumor, Extragonadal Germ Cell Tumor, Extrahepatic Bile Duct Cancer, Eye Cancer, Female Breast Cancer, Gaucher's Disease, Gallbladder Cancer, Gastric Cancer, Gastrointestinal Carcinoid Tumor, Gastrointestinal Tumors, Germ Cell Tumors, Gestational Trophoblastic Tumor, Hairy Cell Leukemia, Head and Neck Cancer, Hepatocellular Cancer, Hodgkin's Lymphoma, Hypergammaglobulinemia, Hypopharyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Cancer, Lung Cancer, Lymphoproliferative Disorders, Macroglobulinemia, Male Breast Cancer, Malignant Mesothelioma, Malignant Thymoma, Medulloblastoma, Melanoma, Mesothelioma, Metastatic Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myelogenous Leukemia, Myeloid Leukemia, Myeloproliferative Disorders, Nasal Cavity and Paranasal Sinus Cancer, Nasopharyngeal Cancer, Neuroblastoma, Non-Hodgkin's Lymphoma, Nonmelanoma Skin Cancer, Non-Small Cell Lung Cancer, Occult Primary Metastatic Squamous Neck Cancer, Oropharyngeal Cancer, Osteo-/Malignant Fibrous Sarcoma, Osteosarcoma/Malignant Fibrous Histiocytoma, Osteosarcoma/Malignant Fibrous Histiocytoma of Bone, Ovarian Epithelial Cancer, Ovarian Germ Cell Tumor, Ovarian Low Malignant Potential Tumor, Pancreatic Cancer, Paraproteinemias, Polycythemia vera, Parathyroid Cancer, Penile Cancer, Pheochromocytoma, Pituitary Tumor, Primary Central Nervous System Lymphoma, Primary Liver Cancer, Prostate Cancer, Rectal Cancer, Renal Cell Cancer, Renal Pelvis and Ureter Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumors, T-Cell Lymphoma, Testicular Cancer, Thymoma, Thyroid Cancer, Transitional Cell Cancer of the Renal Pelvis and Ureter, Transitional Renal Pelvis and Ureter Cancer, Trophoblastic Tumors, Ureter and Renal Pelvis Cell Cancer, Urethral Cancer, Uterine Cancer, Uterine Sarcoma, Vaginal Cancer, Visual Pathway and Hypothalamic Glioma, Vulvar Cancer, Waldenstrom's Macroglobulinemia, Wilms' Tumor, and any other hyperproliferative disease, besides neoplasia, located in an organ system listed above.

The methods and compositions described and claimed herein may be used to treat malignant or premalignant conditions and to prevent progression to a neoplastic or malignant state, including but not limited to those disorders described above. Such uses are indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, Basic Pathology, 2d Ed., W. B. Saunders Co., Philadelphia, pp. 68-79 (1976)).

Dysplasia is frequently a forerunner of cancer, and is found mainly in the epithelia. It is the most disorderly form of non-neoplastic cell growth, involving a loss in individual cell uniformity and in the architectural orientation of cells. Dysplasia characteristically occurs where there exists chronic irritation or inflammation. Dysplastic disorders which can be treated include, but are not limited to, anhidrotic ectodermal dysplasia, anterofacial dysplasia, asphyxiating thoracic dysplasia, atriodigital dysplasia, bronchopulmonary dysplasia, cerebral dysplasia, cervical dysplasia, chondroectodermal dysplasia, cleidocranial dysplasia, congenital ectodermal dysplasia, craniodiaphysial dysplasia, craniocarpotarsal dysplasia, craniometaphysial dysplasia, dentin dysplasia, diaphysial dysplasia, ectodermal dysplasia, enamel dysplasia, encephalo-ophthalmic dysplasia, dysplasia epiphysialis hemimelia, dysplasia epiphysialis multiplex, dysplasia epiphysialis punctata, epithelial dysplasia, faciodigitogenital dysplasia, familial fibrous dysplasia of jaws, familial white folded dysplasia, fibromuscular dysplasia, fibrous dysplasia of bone, florid osseous dysplasia, hereditary renal-retinal dysplasia, hidrotic ectodermal dysplasia, hypohidrotic ectodermal dysplasia, lymphopenic thymic dysplasia, mammary dysplasia, mandibulofacial dysplasia, metaphysial dysplasia, Mondini dysplasia, monostotic fibrous dysplasia, mucoepithelial dysplasia, multiple epiphysial dysplasia, oculoauriculovertebral dysplasia, oculodentodigital dysplasia, oculovertebral dysplasia, odontogenic dysplasia, opthalmomandibulomelic dysplasia, periapical cemental dysplasia, polyostotic fibrous dysplasia, pseudoachondroplastic spondyloepiphysial dysplasia, retinal dysplasia, septo-optic dysplasia, spondyloepiphysial dysplasia, and ventriculoradial dysplasia.

Additional pre-neoplastic disorders which can be treated include, but are not limited to, benign dysproliferative disorders (e.g., benign tumors, fibrocystic conditions, tissue hypertrophy, intestinal polyps or adenomas, and esophageal dysplasia), leukoplakia, keratoses, Bowen's disease, Farmer's Skin, solar cheilitis, and solar keratosis.

In preferred embodiments, the method of the invention is used to inhibit growth, progression, and/or metastasis of cancers, in particular those listed above.

Additional hyperproliferative diseases, disorders, and/or conditions include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, emangioblastoma, acoustic neuroma, oligodendroglioma, meningioma, melanoma, neuroblastoma, and retinoblastoma.

Other Therapeutic Agents

A wide variety of therapeutic reagents can be administered concurrently or sequentially with the targeted delivery complex. For example, drugs, toxins, oligonucleotides, immunomodulators, hormones, hormone antagonists, enzymes, enzyme inhibitors, radionuclides, angiogenesis inhibitors, etc. The therapeutic agents recited here are those agents that also are useful for administration separately with a targeted delivery complex as described above. Therapeutic agents include, for example, chemotherapeutic drugs such as vinca alkaloids, anthracyclines, gemcitabine, epipodophyllotoxins, taxanes, antimetabolites, alkylating agents, antibiotics, SN-38, COX-2 inhibitors, antimitotics, anti-angiogenic and pro-apoptotic agents, particularly doxorubicin, methotrexate, taxol, CPT-11, camptothecins, proteosome inhibitors, mTOR inhibitors, HDAC inhibitors, tyrosine kinase inhibitors, and others.

Other useful cancer chemotherapeutic drugs include nitrogen mustards, alkyl sulfonates, nitrosoureas, triazenes, folic acid analogs, COX-2 inhibitors, antimetabolites, pyrimidine analogs, purine analogs, platinum coordination complexes, mTOR inhibitors, tyrosine kinase inhibitors, proteosome inhibitors, HDAC inhibitors, camptothecins, hormones, and the like. Suitable chemotherapeutic agents are described in REMINGTON'S PHARMACEUTICAL SCIENCES, 19th Ed. (Mack Publishing Co. 1995), and in GOODMAN AND GILMAN'S THE PHARMACOLOGICAL BASIS OF THERAPEUTICS, 7th Ed. (MacMillan Publishing Co. 1985), as well as revised editions of these publications. Other suitable chemotherapeutic agents, such as experimental drugs, are known to those of skill in the art.

In a preferred embodiment, conjugates of camptothecins and related compounds, such as SN-38, may be conjugated to an anti-cancer antibody, for example as disclosed in U.S. Pat. No. 7,591,994; and U.S. Ser. No. 11/388,032, filed Mar. 23, 2006, the Examples section of each of which is incorporated herein by reference.

A toxin can be of animal, plant or microbial origin. A toxin, such as *Pseudomonas* exotoxin, may also be complexed to or form the therapeutic agent portion of an immunoconjugate. Other toxins include ricin, abrin, ribonuclease (RNase), DNase I, Staphylococcal enterotoxin-A, pokeweed antiviral protein, onconase, gelonin, diphtheria toxin, *Pseudomonas* exotoxin, and *Pseudomonas* endotoxin. See, for example, Pastan et al., Cell 47:641 (1986), Goldenberg, Calif.—A Cancer Journal for Clinicians 44:43 (1994), Sharkey and Goldenberg, Calif.—A Cancer Journal for Clinicians 56:226 (2006). Additional toxins suitable for use are known to those of skill in the art and are disclosed in U.S. Pat. No. 6,077,499, the Examples section of which is incorporated herein by reference.

As used herein, the term "immunomodulator" includes a cytokine, a lymphokine, a monokine, a stem cell growth factor, a lymphotoxin, a hematopoietic factor, a colony stimulating factor (CSF), an interferon (IFN), parathyroid hormone, thyroxine, insulin, proinsulin, relaxin, prorelaxin, follicle stimulating hormone (FSH), thyroid stimulating hormone (TSH), luteinizing hormone (LH), hepatic growth factor, prostaglandin, fibroblast growth factor, prolactin, placental lactogen, OB protein, a transforming growth factor (TGF), TGF-$\alpha$, TGF-$\beta$, insulin-like growth factor (IGF), erythropoietin, thrombopoietin, tumor necrosis factor (TNF), TNF-$\alpha$, TNF-$\beta$, a mullerian-inhibiting substance, mouse gonadotropin-associated peptide, inhibin, activin, vascular endothelial growth factor, integrin, interleukin (IL), granulocyte-colony stimulating factor (G-CSF), granulocyte macrophage-colony stimulating factor (GM-CSF), interferon-$\alpha$, interferon-$\beta$, interferon-$\gamma$, S1 factor, IL-1, IL-1 cc, IL-2, IL-3, IL-4, IL-5, IL-6, IL-7, IL-8, IL-9, IL-10, IL-11, IL-12, IL-13, IL-14, IL-15, IL-16, IL-17, IL-18 IL-21 and IL-25, LIF, kit-ligand, FLT-3, angiostatin, thrombospondin, endostatin and LT, and the like.

The targeted delivery complex may be administered with an immunoconjugate comprising one or more radioactive isotopes useful for treating diseased tissue. Particularly useful therapeutic radionuclides include, but are not limited to $^{111}$In, $^{177}$Lu, $^{212}$Bi, $^{213}$Bi, $^{211}$At, $^{62}$Cu, $^{64}$Cu, $^{67}$Cu, $^{90}$Y, $^{125}$I, $^{131}$I, $^{32}$P, $^{33}$P, $^{47}$Sc, $^{111}$Ag, $^{67}$Ga, $^{142}$Pr, $^{153}$Sm, $^{161}$Tb, $^{166}$Dy, $^{166}$Ho, $^{186}$Re, $^{188}$Re, $^{189}$Re, $^{212}$Pb, $^{223}$Ra, $^{225}$Ac, $^{59}$Fe, $^{75}$Se, $^{77}$As, $^{89}$Mo, $^{99}$Mo, $^{105}$Rh, $^{109}$Pd, $^{143}$Pr, $^{149}$Pm, $^{169}$Er, $^{194}$Ir, $^{198}$Au, $^{199}$Au, and $^{211}$Pb. The therapeutic radionuclide preferably has a decay energy in the range of 20 to 6,000 keV, preferably in the ranges 60 to 200 keV for an Auger emitter, 100-2,500 keV for a beta emitter, and 4,000-6,000 keV for an alpha emitter. Maximum decay energies of useful beta-particle-emitting nuclides are preferably 20-5,000 keV, more preferably 100-4,000 keV, and most preferably 500-2,500 keV. Also preferred are radionuclides that substantially decay with Auger-emitting particles. For example, Co-58, Ga-67, Br-80m, Tc-99m, Rh-103m, Pt-109, In-111, Sb-119, I-125, Ho-161, Os-189m and Ir-192. Decay energies of useful beta-particle-emitting nuclides are preferably <1,000 keV, more preferably <100 keV, and most preferably <70 keV. Also preferred are radionuclides that substantially decay with generation of alpha-particles. Such radionuclides include, but are not limited to: Dy-152, At-211, Bi-212, Ra-223, Rn-219, Po-215, Bi-211, Ac-225, Fr-221, At-217, Bi-213 and Fm-255. Decay energies of useful alpha-particle-emitting radionuclides are preferably 2,000-10,000 keV, more preferably 3,000-8,000 keV, and most preferably 4,000-7,000 keV.

Additional potential therapeutic radioisotopes include $^{11}$C, $^{13}$N, $^{15}$O, $^{75}$Br, $^{198}$Au, $^{224}$Ac, $^{126}$I, $^{133}$I, $^{77}$Br, $^{113m}$In, $^{95}$Ru, $^{97}$Ru, $^{103}$Ru, $^{105}$Ru, $^{107}$Hg, $^{203}$Hg, $^{121m}$Te, $^{122m}$Te, $^{125m}$Te, $^{165}$Tm, $^{167}$Tm, $^{168}$Tm, $^{197}$Pt, $^{109}$Pd, $^{105}$Rh, $^{142}$Pr, $^{143}$Pr, $^{161}$Tb, $^{166}$Ho, $^{199}$Au, $^{57}$Co, $^{58}$Co, $^{51}$Cr, $^{59}$Fe, $^{75}$Se, $^{201}$Tl, $^{225}$Ac, $^{76}$Br, $^{169}$Yb, and the like.

Pharmaceutically Suitable Excipients

The targeted delivery complexes to be delivered to a subject can comprise one or more pharmaceutically suitable excipients, one or more additional ingredients, or some combination of these. The targeted delivery complex can be formulated according to known methods to prepare pharmaceutically useful compositions, whereby the targeted delivery complex is combined in a mixture with a pharmaceutically suitable excipient. Sterile phosphate-buffered saline is one example of a pharmaceutically suitable excipient. Other suitable excipients are well-known to those in the art. See, for example, Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The targeted delivery complex can be formulated for intravenous administration via, for example, bolus injection or continuous infusion. Formulations for injection can be presented in unit dosage form, e.g., in ampules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

Kits

Various embodiments may concern kits containing components suitable for treating or diagnosing diseased tissue in a patient. Exemplary kits may contain at least one targeted delivery complex as described herein. If the composition containing components for administration is not formulated for delivery via the alimentary canal, such as by oral delivery, a device capable of delivering the kit components through some other route may be included. One type of device, for applications such as parenteral delivery, is a syringe that is used to inject the composition into the body of a subject. Inhalation devices may also be used. In certain embodiments, a targeted delivery complex may be provided in the form of a prefilled syringe or autoinjection pen containing a sterile, liquid formulation or lyophilized preparation of antibody (e.g., Kivitz et al., Clin. Ther. 2006, 28:1619-29).

The kit components may be packaged together or separated into two or more containers. In some embodiments, the containers may be vials that contain sterile, lyophilized formulations of a composition that are suitable for reconstitution. A kit may also contain one or more buffers suitable for reconstitution and/or dilution of other reagents. Other containers that may be used include, but are not limited to, a pouch, tray, box, tube, or the like. Kit components may be packaged and maintained sterilely within the containers. Another component that can be included is instructions for use of the kit.

EXAMPLES

The examples below are illustrative of embodiments of the current invention and are not limiting to the scope of the claims.

Example 1

Preparation of Dock-and-Lock (DNL) Constructs

DDD and AD Fusion Proteins

The DNL technique can be used to make dimers, trimers, tetramers, hexamers, etc. comprising virtually any antibody, antibody fragment, siRNA carrier or other effector moieties. For certain preferred embodiments, the antibodies and carrier moieties of the subject targeted delivery complex may be produced as fusion proteins comprising either a dimerization and docking domain (DDD) or anchoring domain (AD) sequence. Although in preferred embodiments the DDD and AD moieties may be joined to targeting molecules and siRNA carriers as fusion proteins, the skilled artisan will realize that other methods of conjugation exist, particularly for non-protein siRNA carriers, such as chemical cross-linking, click chemistry reaction, etc.

The technique is not limiting and any protein or peptide of use may be produced as an AD or DDD fusion protein for incorporation into a DNL construct. Where chemical cross-linking is utilized, the AD and DDD conjugates may comprise any molecule that may be cross-linked to an AD or DDD sequence using any cross-linking technique known in the art. In certain exemplary embodiments, a dendrimer or other polymeric moiety such as polyethyleneimine or polyethylene glycol (PEG), may be incorporated into a DNL construct, as described in further detail below.

For different types of DNL constructs, different AD or DDD sequences may be utilized. Exemplary DDD and AD sequences are provided below.

```
DDD1:
                                    (SEQ ID NO: 33)
SHIQIPPGLTELLQGYTVEVLRQQPPDLVEFAVEYFTRLREARA

DDD2:
                                    (SEQ ID NO: 34)
CGHIQIPPGLTELLQGYTVEVLRQQPPDLVEFAVEYFTRLREARA

AD1:
                                    (SEQ ID NO: 35)
QIEYLAKQIVDNAIQQA

AD2:
                                    (SEQ ID NO: 36)
CGQIFYLAKQIVDNAIQQAGC
```

The skilled artisan will realize that DDD1 and DDD2 comprise the DDD sequence of the human RIIα form of protein kinase A. However, in alternative embodiments, the DDD and AD moieties may be based on the DDD sequence of the human RIα form of protein kinase A and a corresponding AKAP sequence, as exemplified in DDD3, DDD3C and AD3 below.

DDD3

(SEQ ID NO: 37)
SLRECELYVQKHNIQALLKDSIVQLCTARPERPMAFLREYFERLEKEEAK

DDD3C (SEQ ID NO: 38)
MSCGGSLRECELYVQKHNIQALLKDSIVQLCTARPERPMAFLREYFERLE
KEEAK

AD3

(SEQ ID NO: 39)
CGFEELAWKIAKMIWSDVFQQGC

Expression Vectors

The plasmid vector pdHL2 has been used to produce a number of antibodies and antibody-based constructs. See Gillies et al., J Immunol Methods (1989), 125:191-202; Losman et al., Cancer (Phila) (1997), 80:2660-6. The di-cistronic mammalian expression vector directs the synthesis of the heavy and light chains of IgG. The vector sequences are mostly identical for many different IgG-pdHL2 constructs, with the only differences existing in the variable domain (VH and VL) sequences. Using molecular biology tools known to those skilled in the art, these IgG expression vectors can be converted into Fab-DDD or Fab-AD expression vectors. To generate Fab-DDD expression vectors, the coding sequences for the hinge, CH2 and CH3 domains of the heavy chain are replaced with a sequence encoding the first 4 residues of the hinge, a 14 residue Gly-Ser linker and the first 44 residues of human RIIα (referred to as DDD1). To generate Fab-AD expression vectors, the sequences for the hinge, CH2 and CH3 domains of IgG are replaced with a sequence encoding the first 4 residues of the hinge, a 15 residue Gly-Ser linker and a 17 residue synthetic AD called AKAP-IS (referred to as AD1), which was generated using bioinformatics and peptide array technology and shown to bind RIIα dimers with a very high affinity (0.4 nM). See Alto, et al. Proc. Natl. Acad. Sci., U.S.A. (2003), 100:4445-50.

Two shuttle vectors were designed to facilitate the conversion of IgG-pdHL2 vectors to either Fab-DDD1 or Fab-AD1 expression vectors, as described below.

Preparation of CH1

The CH1 domain was amplified by PCR using the pdHL2 plasmid vector as a template. The left PCR primer consisted of the upstream (5') end of the CH1 domain and a SacII restriction endonuclease site, which is 5' of the CH1 coding sequence. The right primer consisted of the sequence coding for the first 4 residues of the hinge (PKSC) followed by four glycines and a serine, with the final two codons (GS) comprising a Bam HI restriction site. The 410 bp PCR amplimer was cloned into the PGEMT® PCR cloning vector (PROMEGA®, Inc.) and clones were screened for inserts in the T7 (5') orientation.

A duplex oligonucleotide was synthesized to code for the amino acid sequence of DDD1 preceded by 11 residues of the linker peptide, with the first two codons comprising a BamHI restriction site. A stop codon and an EagI restriction site are appended to the 3' end. The encoded polypeptide sequence is shown below.

(SEQ ID NO: 40)
GSGGGGSGGGGSHIQIPPGLTELLQGYTVEVLRQQPPDLVEFAVEYFTR
LREARA

Two oligonucleotides, designated RIIA1-44 top and RIIA1-44 bottom, which overlap by 30 base pairs on their 3' ends, were synthesized and combined to comprise the central 154 base pairs of the 174 bp DDD1 sequence. The oligonucleotides were annealed and subjected to a primer extension reaction with Taq polymerase. Following primer extension, the duplex was amplified by PCR. The amplimer was cloned into PGEMT® and screened for inserts in the T7 (5') orientation.

A duplex oligonucleotide was synthesized to code for the amino acid sequence of AD1 preceded by 11 residues of the linker peptide with the first two codons comprising a BamHI restriction site. A stop codon and an EagI restriction site are appended to the 3' end. The encoded polypeptide sequence is shown below.

(SEQ ID NO: 41)
GSGGGGSGGGGSQIEYLAKQIVDNAIQQA

Two complimentary overlapping oligonucleotides encoding the above peptide sequence, designated AKAP-IS Top and AKAP-IS Bottom, were synthesized and annealed. The duplex was amplified by PCR. The amplimer was cloned into the PGEMT® vector and screened for inserts in the T7 (5') orientation.

Ligating DDD1 with CH1

A 190 bp fragment encoding the DDD1 sequence was excised from PGEMT® with BamHI and NotI restriction enzymes and then ligated into the same sites in CH1-PGEMT® to generate the shuttle vector CH1-DDD1-PGEMT®.

Ligating AD1 with CH1

A 110 bp fragment containing the AD1 sequence was excised from PGEMT® with BamHI and NotI and then ligated into the same sites in CH1-PGEMT® to generate the shuttle vector CH1-AD1-PGEMT®.

Cloning CH1-DDD1 or CH1-AD1 into pdHL2-Based Vectors

With this modular design either CH1-DDD1 or CH1-AD1 can be incorporated into any IgG construct in the pdHL2 vector. The entire heavy chain constant domain is replaced with one of the above constructs by removing the SacII/EagI restriction fragment (CH1-CH3) from pdHL2 and replacing it with the SacII/EagI fragment of CH1-DDD1 or CH1-AD1, which is excised from the respective pGemT shuttle vector.

Construction of h679-Fd-AD1-pdHL2 h679-Fd-AD1-pdHL2 is an expression vector for production of h679 Fab with AD1 coupled to the carboxyl terminal end of the CH1 domain of the Fd via a flexible Gly/Ser peptide spacer composed of 14 amino acid residues. A pdHL2-based vector containing the variable domains of h679 was converted to h679-Fd-AD1-pdHL2 by replacement of the SacII/EagI fragment with the CH1-AD1 fragment, which was excised from the CH1-AD1-SV3 shuttle vector with SacII and EagI.

Construction of C-DDD1-Fd-hMN-14-pdHL2

C-DDD1-Fd-hMN-14-pdHL2 is an expression vector for production of a stable dimer that comprises two copies of a fusion protein C-DDD1-Fab-hMN-14, in which DDD1 is linked to hMN-14 Fab at the carboxyl terminus of CH1 via a flexible peptide spacer. The plasmid vector hMN-14(I)-pdHL2, which has been used to produce hMN-14 IgG, was converted to C-DDD1-Fd-hMN-14-pdHL2 by digestion with SacII and EagI restriction endonucleases to remove the CH1-CH3 domains and insertion of the CH1-DDD1 fragment, which was excised from the CH1-DDD1-SV3 shuttle vector with SacII and EagI.

The same technique has been utilized to produce plasmids for Fab expression of a wide variety of known antibodies, such as hLL1, hLL2, hPAM4, hR1, hRS7, hMN-14, hMN-15, hA19, hA20 and many others. Generally, the antibody variable region coding sequences were present in a pdHL2 expression vector and the expression vector was converted for production of an AD- or DDD-fusion protein as described above. The AD- and DDD-fusion proteins comprising a Fab fragment of any of such antibodies may be combined, in an approximate ratio of two DDD-fusion proteins per one AD-fusion protein, to generate a trimeric DNL construct comprising two Fab fragments of a first antibody and one Fab fragment of a second antibody.

Construction of N-DDD1-Fd-hMN-14-pdHL2

N-DDD1-Fd-hMN-14-pdHL2 is an expression vector for production of a stable dimer that comprises two copies of a fusion protein N-DDD1-Fab-hMN-14, in which DDD1 is linked to hMN-14 Fab at the amino terminus of VH via a flexible peptide spacer. The expression vector was engineered as follows. The DDD1 domain was amplified by PCR.

As a result of the PCR, an NcoI restriction site and the coding sequence for part of the linker containing a BamHI restriction were appended to the 5' and 3' ends, respectively. The 170 bp PCR amplimer was cloned into the pGemT vector and clones were screened for inserts in the T7 (5') orientation. The 194 bp insert was excised from the pGemT vector with NcoI and SalI restriction enzymes and cloned into the SV3 shuttle vector, which was prepared by digestion with those same enzymes, to generate the intermediate vector DDD1-SV3.

The hMN-14 Fd sequence was amplified by PCR. As a result of the PCR, a BamHI restriction site and the coding sequence for part of the linker were appended to the 5' end of the amplimer. A stop codon and EagI restriction site was appended to the 3' end. The 1043 bp amplimer was cloned into pGemT. The hMN-14-Fd insert was excised from pGemT with BamHI and EagI restriction enzymes and then ligated with DDD1-SV3 vector, which was prepared by digestion with those same enzymes, to generate the construct N-DDD1-hMN-14Fd-SV3.

The N-DDD1-hMN-14 Fd sequence was excised with XhoI and EagI restriction enzymes and the 1.28 kb insert fragment was ligated with a vector fragment that was prepared by digestion of C-hMN-14-pdHL2 with those same enzymes. The final expression vector was N-DDD1-Fd-hMN-14-pDHL2. The N-linked Fab fragment exhibited similar DNL complex formation and antigen binding characteristics as the C-linked Fab fragment (not shown).

C-DDD2-Fd-hMN-14-pdHL2

C-DDD2-Fd-hMN-14-pdHL2 is an expression vector for production of C-DDD2-Fab-hMN-14, which possesses a dimerization and docking domain sequence of DDD2 appended to the carboxyl terminus of the Fd of hMN-14 via a 14 amino acid residue Gly/Ser peptide linker. The fusion protein secreted is composed of two identical copies of hMN-14 Fab held together by non-covalent interaction of the DDD2 domains.

The expression vector was engineered as follows. Two overlapping, complimentary oligonucleotides, which comprise the coding sequence for part of the linker peptide and residues 1-13 of DDD2, were made synthetically. The oligonucleotides were annealed and phosphorylated with T4 PNK, resulting in overhangs on the 5' and 3' ends that are compatible for ligation with DNA digested with the restriction endonucleases BamHI and PstI, respectively.

The duplex DNA was ligated with the shuttle vector CH1-DDD1-PGEMT®, which was prepared by digestion with BamHI and PstI, to generate the shuttle vector CH1-DDD2-PGEMT®. A 507 bp fragment was excised from CH1-DDD2-PGEMT® with SacII and EagI and ligated with the IgG expression vector hMN-14(I)-pdHL2, which was prepared by digestion with SacII and EagI. The final expression construct was designated C-DDD2-Fd-hMN-14-pdHL2. Similar techniques have been utilized to generated DDD2-fusion proteins of the Fab fragments of a number of different humanized antibodies.

h679-Fd-AD2-pdHL2 h679-Fab-AD2, was designed to pair as B to C-DDD2-Fab-hMN-14 as A. h679-Fd-AD2-pdHL2 is an expression vector for the production of h679-Fab-AD2, which possesses an anchoring domain sequence of AD2 appended to the carboxyl terminal end of the CH1 domain via a 14 amino acid residue Gly/Ser peptide linker. AD2 has one cysteine residue preceding and another one following the anchor domain sequence of AD1.

The expression vector was engineered as follows. Two overlapping, complimentary oligonucleotides (AD2 Top and AD2 Bottom), which comprise the coding sequence for AD2 and part of the linker sequence, were made synthetically. The oligonucleotides were annealed and phosphorylated with T4 PNK, resulting in overhangs on the 5' and 3' ends that are compatible for ligation with DNA digested with the restriction endonucleases BamHI and SpeI, respectively.

The duplex DNA was ligated into the shuttle vector CH1-AD1-PGEMT®, which was prepared by digestion with BamHI and SpeI, to generate the shuttle vector CH1-AD2-PGEMT®. A 429 base pair fragment containing CH1 and AD2 coding sequences was excised from the shuttle vector with SacII and EagI restriction enzymes and ligated into h679-pdHL2 vector that prepared by digestion with those same enzymes. The final expression vector is h679-Fd-AD2-pdHL2.

Example 2

Generation of TF1 DNL Construct

A large scale preparation of a DNL construct, referred to as TF1, was carried out as follows. N-DDD2-Fab-hMN-14 (Protein L-purified) and h679-Fab-AD2 (IMP-291-purified) were first mixed in roughly stoichiometric concentrations in 1 mM EDTA, PBS, pH 7.4. Before the addition of TCEP, SE-HPLC did not show any evidence of $a_2b$ formation (not shown). Instead there were peaks representing $a_4$ (7.97 mM; 200 kDa), $a_2$ (8.91 mM; 100 kDa) and B (10.01 min; 50 kDa). Addition of 5 mM TCEP rapidly resulted in the formation of the $a_2b$ complex as demonstrated by a new peak at 8.43 mM, consistent with a 150 kDa protein (not shown). Apparently there was excess B in this experiment as a peak attributed to h679-Fab-AD2 (9.72 mM) was still evident yet no apparent peak corresponding to either $a_2$ or $a_4$ was observed. After reduction for one hour, the TCEP was removed by overnight dialysis against several changes of PBS. The resulting solution was brought to 10% DMSO and held overnight at room temperature.

When analyzed by SE-HPLC, the peak representing $a_2b$ appeared to be sharper with a slight reduction of the retention time by 0.1 mM to 8.31 mM (not shown), which, based on our previous findings, indicates an increase in binding affinity. The complex was further purified by IMP-291 affinity chromatography to remove the kappa chain contaminants. As expected, the excess h679-AD2 was co-purified and later removed by preparative SE-HPLC (not shown).

TF1 is a highly stable complex. When TF1 was tested for binding to an HSG (IMP-239) sensorchip, there was no apparent decrease of the observed response at the end of sample injection. In contrast, when a solution containing an equimolar mixture of both C-DDD1-Fab-hMN-14 and h679-Fab-AD1 was tested under similar conditions, the observed increase in response units was accompanied by a detectable drop during and immediately after sample injection, indicating that the initially formed $a_2b$ structure was unstable. Moreover, whereas subsequent injection of WI2 gave a substantial increase in response units for TF1, no increase was evident for the C-DDD1/AD1 mixture.

The additional increase of response units resulting from the binding of WI2 to TF1 immobilized on the sensorchip corresponds to two fully functional binding sites, each contributed by one subunit of N-DDD2-Fab-hMN-14. This was confirmed by the ability of TF1 to bind two Fab fragments of WI2 (not shown). When a mixture containing h679-AD2 and N-DDD1-hMN14, which had been reduced and oxidized exactly as TF1, was analyzed by BIAcore, there was little additional binding of WI2 (not shown), indicating that a disulfide-stabilized $a_2b$ complex such as TF1 could only form through the interaction of DDD2 and AD2.

Two improvements to the process were implemented to reduce the time and efficiency of the process. First, a slight molar excess of N-DDD2-Fab-hMN-14 present as a mixture of $a_4/a_2$ structures was used to react with h679-Fab-AD2 so that no free h679-Fab-AD2 remained and any $a_4/a_2$ structures not tethered to h679-Fab-AD2, as well as light chains, would be removed by IMP-291 affinity chromatography. Second, hydrophobic interaction chromatography (HIC) has replaced dialysis or diafiltration as a means to remove TCEP following reduction, which would not only shorten the process time but also add a potential viral removing step. N-DDD2-Fab-hMN-14 and 679-Fab-AD2 were mixed and reduced with 5 mM TCEP for 1 hour at room temperature. The solution was brought to 0.75 M ammonium sulfate and then loaded onto a Butyl FF HIC column. The column was washed with 0.75 M ammonium sulfate, 5 mM EDTA, PBS to remove TCEP. The reduced proteins were eluted from the HIC column with PBS and brought to 10% DMSO. Following incubation at room temperature overnight, highly purified TF1 was isolated by IMP-291 affinity chromatography (not shown). No additional purification steps, such as gel filtration, were required.

Example 3

Generation of TF2 DNL Construct

A trimeric DNL construct designated TF2 was obtained by reacting C-DDD2-Fab-hMN-14 with h679-Fab-AD2. A pilot batch of TF2 was generated with >90% yield as follows. Protein L-purified C-DDD2-Fab-hMN-14 (200 mg) was mixed with h679-Fab-AD2 (60 mg) at a 1.4:1 molar ratio. The total protein concentration was 1.5 mg/ml in PBS containing 1 mM EDTA. Subsequent steps involved TCEP reduction, HIC chromatography, DMSO oxidation, and IMP 291 affinity chromatography. Before the addition of TCEP, SE-HPLC did not show any evidence of $a_2b$ formation. Addition of 5 mM TCEP rapidly resulted in the formation of $a_2b$ complex consistent with a 157 kDa protein expected for the binary structure. TF2 was purified to near homogeneity by IMP 291 affinity chromatography (not shown). IMP 291 is a synthetic peptide containing the HSG hapten to which the 679 Fab binds (Rossi et al., 2005, Clin Cancer Res 11:7122s-29s). SE-HPLC analysis of the IMP 291 unbound fraction demonstrated the removal of $a_4$, $a_2$ and free kappa chains from the product (not shown).

The functionality of TF2 was determined by BIACORE® assay. TF2, C-DDD1-hMN-14+h679-AD1 (used as a control sample of noncovalent $a_2b$ complex), or C-DDD2-hMN-14+h679-AD2 (used as a control sample of unreduced $a_2$ and b components) were diluted to 1 µg/ml (total protein) and passed over a sensorchip immobilized with HSG. The response for TF2 was approximately two-fold that of the two control samples, indicating that only the h679-Fab-AD component in the control samples would bind to and remain on the sensorchip. Subsequent injections of WI2 IgG, an anti-idiotype antibody for hMN-14, demonstrated that only TF2 had a DDD-Fab-hMN-14 component that was tightly associated with h679-Fab-AD as indicated by an additional signal response. The additional increase of response units resulting from the binding of WI2 to TF2 immobilized on the sensorchip corresponded to two fully functional binding sites, each contributed by one subunit of C-DDD2-Fab-hMN-14. This was confirmed by the ability of TF2 to bind two Fab fragments of WI2 (not shown).

Example 4

Production of TF10 Bispecific Antibody

A similar protocol was used to generate a trimeric TF10 DNL construct, comprising two copies of a C-DDD2-Fab-hPAM4 and one copy of C-AD2-Fab-679. The cancer-targeting antibody component in TF10 was derived from hPAM4, a humanized anti-pancreatic cancer mucin MAb that has been studied in detail as a radiolabeled MAb (e.g., Gold et al., Clin. Cancer Res. 13: 7380-7387, 2007). The hapten-binding component was derived from h679, a humanized anti-histaminyl-succinyl-glycine (HSG) MAb. The TF10 bispecific ([hPAM4]$_2$×h679) antibody was produced using the method disclosed for production of the (anti CEA)$_2$×anti HSG bsAb TP2, as described above. The TF10 construct bears two humanized PAM4 Fabs and one humanized 679 Fab.

The two fusion proteins (hPAM4-DDD and h679-AD2) were expressed independently in stably transfected myeloma cells. The tissue culture supernatant fluids were combined, resulting in a two-fold molar excess of hPAM4-DDD. The reaction mixture was incubated at room temperature for 24 hours under mild reducing conditions using 1 mM reduced glutathione. Following reduction, the DNL reaction was completed by mild oxidation using 2 mM oxidized glutathione. TF10 was isolated by affinity chromatography using IMP 291-affigel resin, which binds with high specificity to the h679 Fab.

The skilled artisan will realize that the DNL techniques disclosed above may be used to produce complexes comprising any combination of antibodies, immunoconjugates, siRNA carrier moieties or other effector moieties that may be attached to an AD or DDD moiety.

Example 5

Production of AD- and DDD-Linked Fab and IgG Fusion Proteins from Multiple Antibodies Using the techniques described in the preceding Examples, the IgG and Fab fusion proteins shown in Table 2 were constructed and incorporated into DNL constructs. The fusion proteins retained the antigen-binding characteristics of the parent antibodies and the DNL constructs exhibited the antigen-binding activities of the incorporated antibodies or antibody fragments.

TABLE 2

Fusion proteins comprising IgG or Fab

| Fusion Protein | Binding Specificity |
|---|---|
| C-AD1-Fab-h679 | HSG |
| C-AD2-Fab-h679 | HSG |
| C-(AD)₂-Fab-h679 | HSG |
| C-AD2-Fab-h734 | Indium-DTPA |
| C-AD2-Fab-hA20 | CD20 |
| C-AD2-Fab-hA20L | CD20 |
| C-AD2-Fab-hL243 | HLA-DR |
| C-AD2-Fab-hLL2 | CD22 |
| N-AD2-Fab-hLL2 | CD22 |
| C-AD2-IgG-hMN-14 | CEACAM5 |
| C-AD2-IgG-hR1 | IGF-1R |
| C-AD2-IgG-hRS7 | EGP-1 |
| C-AD2-IgG-hPAM4 | MUC |
| C-AD2-IgG-hLL1 | CD74 |
| C-DDD1-Fab-hMN-14 | CEACAM5 |
| C-DDD2-Fab-hMN-14 | CEACAM5 |
| C-DDD2-Fab-h679 | HSG |
| C-DDD2-Fab-hA19 | CD19 |
| C-DDD2-Fab-hA20 | CD20 |
| C-DDD2-Fab-hAFP | AFP |
| C-DDD2-Fab-hL243 | HLA-DR |
| C-DDD2-Fab-hLL1 | CD74 |
| C-DDD2-Fab-hLL2 | CD22 |
| C-DDD2-Fab-hMN-3 | CEACAM6 |
| C-DDD2-Fab-hMN-15 | CEACAM6 |
| C-DDD2-Fab-hPAM4 | MUC |
| C-DDD2-Fab-hR1 | IGF-1R |
| C-DDD2-Fab-hRS7 | EGP-1 |
| N-DDD2-Fab-hMN-14 | CEACAM5 |

Example 6

Sequence Variants for DNL

In certain preferred embodiments, the AD and DDD sequences incorporated into the DNL construct comprise the amino acid sequences of AD1, AD2, AD3, DDD1, DDD2, DDD3 or DDD3C as discussed above. However, in alternative embodiments sequence variants of AD and/or DDD moieties may be utilized in construction of the DNL complexes. For example, there are only four variants of human PKA DDD sequences, corresponding to the DDD moieties of PKA RIα, RIIα, RIβ and RIIβ. The RIIα DDD sequence is the basis of DDD1 and DDD2 disclosed above. The four human PKA DDD sequences are shown below. The DDD sequence represents residues 1-44 of RIIα, 1-44 of RIIβ, 12-61 of RIα and 13-66 of RIβ. (Note that the sequence of DDD1 is modified slightly from the human PKA RIIα DDD moiety.)

PKA RIα

(SEQ ID NO: 42)
SLRECELYVQKHNIQALLKDVSIVQLCTARPERPMAFLREYFEKLEKEE
AK

PKA RIβ

(SEQ ID NO: 43)
SLKGCELYVQLHGIQQVLKDCIVHLCISKPERPMKFLREHFEKLEKEEN
RQILA

PKA RIIα

(SEQ ID NO: 44)
SHIQIPPGLTELLQGYTVEVGQQPPDLVDFAVEYFTRLREARRQ

PKA RIIβ

(SEQ ID NO: 45)
SIEIPAGLTELLQGFTVEVLRHQPADLLEFALQHFTRLQQENER

The structure-function relationships of the AD and DDD domains have been the subject of investigation. (See, e.g., Burns-Hamuro et al., 2005, Protein Sci 14:2982-92; Carr et al., 2001, J Biol Chem 276:17332-38; Alto et al., 2003, Proc Natl Acad Sci USA 100:4445-50; Hundsrucker et al., 2006, Biochem J 396:297-306; Stokka et al., 2006, Biochem J 400:493-99; Gold et al., 2006, Mol Cell 24:383-95; Kinderman et al., 2006, Mol Cell 24:397-408, the entire text of each of which is incorporated herein by reference.)

For example, Kinderman et al. (2006) examined the crystal structure of the AD-DDD binding interaction and concluded that the human DDD sequence contained a number of conserved amino acid residues that were important in either dimer formation or AKAP binding, underlined in SEQ ID NO:33 below. (See FIG. 1 of Kinderman et al., 2006, incorporated herein by reference.) The skilled artisan will realize that in designing sequence variants of the DDD sequence, one would desirably avoid changing any of the underlined residues, while conservative amino acid substitutions might be made for residues that are less critical for dimerization and AKAP binding.

(SEQ ID NO: 33)
SHIQIPPGLTELLQGYTVEVLRQQPPDLVEFAVEYFTRLREARA

Alto et al. (2003) performed a bioinformatic analysis of the AD sequence of various AKAP proteins to design an RII selective AD sequence called AKAP-IS (SEQ ID NO:35), with a binding constant for DDD of 0.4 nM. The AKAP-IS sequence was designed as a peptide antagonist of AKAP binding to PKA. Residues in the AKAP-IS sequence where substitutions tended to decrease binding to DDD are underlined in SEQ ID NO:35. The skilled artisan will realize that in designing sequence variants of the AD sequence, one would desirably avoid changing any of the underlined residues, while conservative amino acid substitutions might be made for residues that are less critical for DDD binding.

AKAP-IS sequence (SEQ ID NO: 35)
QIEYLAKQIVDNAIQQA

Gold (2006) utilized crystallography and peptide screening to develop a SuperAKAP-IS sequence (SEQ ID NO:46), exhibiting a five order of magnitude higher selectivity for the RII isoform of PKA compared with the RI isoform. Underlined residues indicate the positions of amino acid substitutions, relative to the AKAP-IS sequence, which increased binding to the DDD moiety of RIIα. In this sequence, the N-terminal Q residue is numbered as residue number 4 and the C-terminal A residue is residue number 20. Residues where substitutions could be made to affect the affinity for RIIα were residues 8, 11, 15, 16, 18, 19 and 20 (Gold et al., 2006). It is contemplated that in certain alternative embodiments, the SuperAKAP-IS sequence may be substituted for the AKAP-IS AD moiety sequence to prepare DNL constructs. Other alternative sequences that might be substituted for the AKAP-IS AD sequence are shown in SEQ ID NO:47-49. Substitutions relative to the AKAP-IS sequence are underlined. It is anticipated that, as with the AD2 sequence shown in SEQ ID NO:46, the AD moiety may also include the additional N-terminal residues cysteine and glycine and C-terminal residues glycine and cysteine.

```
SuperAKAP-IS
                                      (SEQ ID NO: 46)
QIEYVAKQIVDYAIHQA Alternative AKAP sequences
                                      (SEQ ID NO: 47)
QIEYKAKQIVDHAIHQA (SEQ ID NO: 48)
QIEYHAKQIVDHAIHQA (SEQ ID NO: 49)
QIEYVAKQIVDHAIHQA
```

Figure 2:
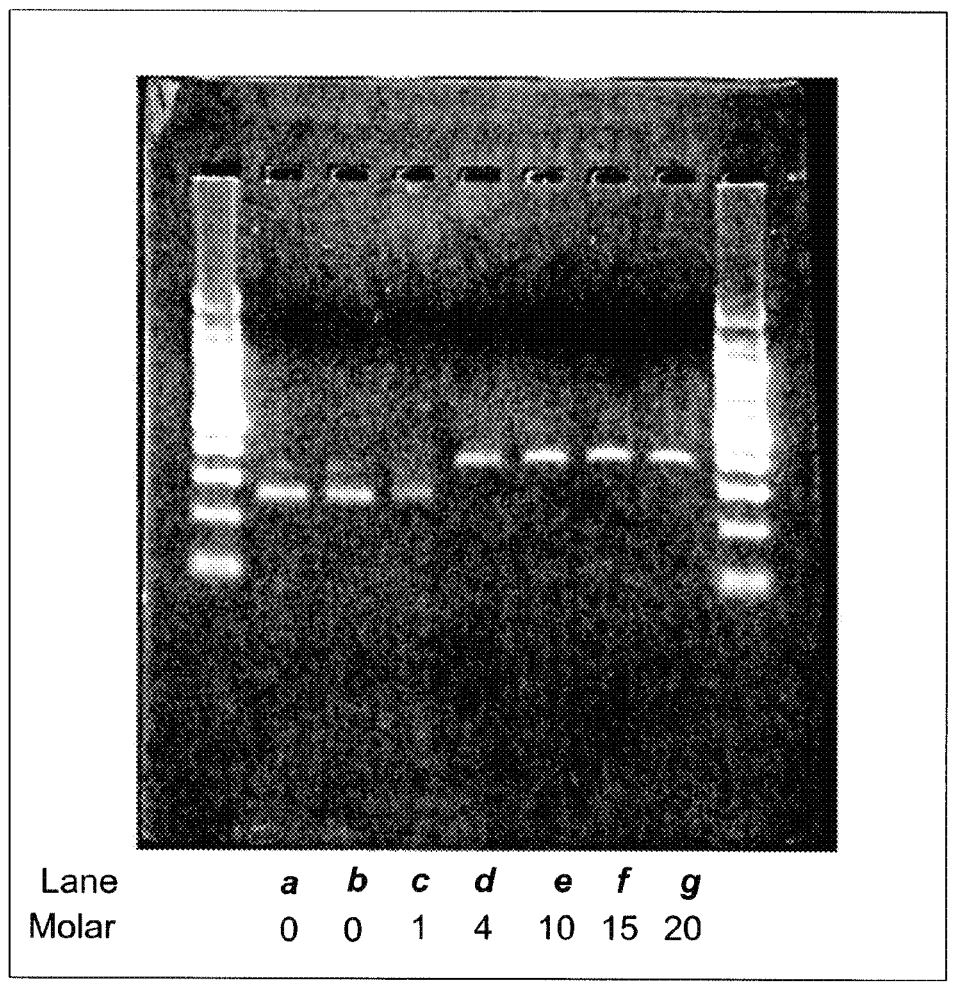
FIG. 2. Gel shift assay for DNA binding by E1-L-thP1.

FIG. 2 of Gold et al. disclosed additional DDD-binding sequences from a variety of AKAP proteins, shown below.

```
RII-Specific AKAPs
AKAP-KL
                                      (SEQ ID NO: 50)
PLEYQAGLLVQNAIQQAI

AKAP79
                                      (SEQ ID NO: 51)
LLIETASSLVKNAIQLSI

AKAP-Lbc
                                      (SEQ ID NO: 52)
LIEEAASRIVDAVIEQVK

RI-Specific AKAPs
AKAPce
                                      (SEQ ID NO: 53)
ALYQFADRFSELVISEAL

RIAD
                                      (SEQ ID NO: 54)
LEQYANQLADQIIKEAT

PV38
                                      (SEQ ID NO: 55)
FEELAWKIAKMIWSDVF

Dual-Specificity AKAPs
AKAP7
                                      (SEQ ID NO: 56)
ELVRLSKRLVENAVLKAV

MAP2D
                                      (SEQ ID NO: 57)
TAEEVSARIVQVVTAEAV

DAKAP1
                                      (SEQ ID NO: 58)
QIKQAAFQLISQVILEAT

DAKAP2
                                      (SEQ ID NO: 59)
LAWKIAKMIVSDVMQQ
```

Stokka et al. (2006) also developed peptide competitors of AKAP binding to PKA, shown in SEQ ID NO:60-62. The peptide antagonists were designated as Ht31 (SEQ ID NO:60), RIAD (SEQ ID NO:61) and PV-38 (SEQ ID NO:62). The Ht-31 peptide exhibited a greater affinity for the RH isoform of PKA, while the RIAD and PV-38 showed higher affinity for RI.

```
Ht31
                                      (SEQ ID NO: 60)
DLIEEAASRIVDAVIEQVKAAGAY

RIAD
                                      (SEQ ID NO: 61)
LEQYANQLADQIIKEATE

PV-38
                                      (SEQ ID NO: 62)
FEELAWKIAKMIWSDVFQQC
```

Hundsrucker et al. (2006) developed still other peptide competitors for AKAP binding to PKA, with a binding constant as low as 0.4 nM to the DDD of the RII form of PKA. The sequences of various AKAP antagonistic peptides are provided in Table 1 of Hundsrucker et al., reproduced in Table 3 below. AKAPIS represents a synthetic RII subunit-binding peptide. All other peptides are derived from the RII-binding domains of the indicated AKAPs.

TABLE 3

| AKAP Peptide sequences | |
|---|---|
| | Peptide Sequence |
| AKAPIS | QIEYLAKQIVDNAIQQA (SEQ ID NO: 35) |
| AKAPIS-P | QIEYLAKQIPDNAIQQA (SEQ ID NO: 63) |
| Ht31 | KGADLIEEAASRIVDAVIEQVKAAG (SEQ ID NO: 64) |
| Ht31-P | KGADLIEEAASRIPDAPIEQVKAAG (SEQ ID NO: 65) |
| AKAP7δ-wt-pep | PEDAELVRLSKRLVENAVLKAVQQY (SEQ ID NO: 66) |
| AKAP7δ-L304T-pep | PEDAELVRTSKRLVENAVLKAVQQY (SEQ ID NO: 67) |
| AKAP7δ-L308D-pep | PEDAELVRLSKRDVENAVLKAVQQY (SEQ ID NO: 68) |
| AKAP7δP-pep | PEDAELVRLSKRLPENAVLKAVQQY (SEQ ID NO: 69) |
| AKAP7δ-PP-pep | PEDAELVRLSKRLPENAPLKAVQQY (SEQ ID NO: 70) |
| AKAP7δ-L314E-pep | PEDAELVRLSKRLVENAVEKAVQQY (SEQ ID NO: 71) |
| AKAP1-pep | EEGLDRNEEIKRAAFQIISQVISEA (SEQ ID NO: 72) |
| AKAP2-pep | LVDDPLEYQAGLLVQNAIQQAIAEQ (SEQ ID NO: 73) |
| AKAP5-pep | QYETLLIETASSLVKNAIQLSIEQL (SEQ ID NO: 74) |

TABLE 3-continued

AKAP Peptide sequences

| | Peptide Sequence |
|---|---|
| AKAP9-pep | LEKQYQEQLEEEVAKVIVSMSIAFA (SEQ ID NO: 75) |
| AKAP10-pep | NTDEAQEELAWKIAKMIVSDIMQQA (SEQ ID NO: 76) |
| AKAP11-pep | VNLDKKAVLAEKIVAEAIEKAEREL (SEQ ID NO: 77) |
| AKAP12-pep | NGILELETKSSKLVQNIIQTAVDQF (SEQ ID NO: 78) |
| AKAP14-pep | TQDKNYEDELTQVALALVEDVINYA (SEQ ID NO: 79) |
| Rab32-pep | ETSAKDNINIEEAARFLVEKILVNH (SEQ ID NO: 80) |

Residues that were highly conserved among the AD domains of different AKAP proteins are indicated below by underlining with reference to the AKAP IS sequence (SEQ ID NO:35). The residues are the same as observed by Alto et al. (2003), with the addition of the C-terminal alanine residue. (See FIG. 4 of Hundsrucker et al. (2006), incorporated herein by reference.) The sequences of peptide antagonists with particularly high affinities for the RII DDD sequence were those of AKAP-IS, AKAP7δ-wt-pep, AKAP7δ-L304T-pep and AKAP7δ-L308D-pep.

```
          AKAP-IS
                              (SEQ ID NO: 35)
          QIEYLAKQIVDNAIQQA
```

Carr et al. (2001) examined the degree of sequence homology between different AKAP-binding DDD sequences from human and non-human proteins and identified residues in the DDD sequences that appeared to be the most highly conserved among different DDD moieties. These are indicated below by underlining with reference to the human PKA RIIα DDD sequence of SEQ ID NO:33. Residues that were particularly conserved are further indicated by italics. The residues overlap with, but are not identical to those suggested by Kinderman et al. (2006) to be important for binding to AKAP proteins. The skilled artisan will realize that in designing sequence variants of DDD, it would be most preferred to avoid changing the most conserved residues (italicized), and it would be preferred to also avoid changing the conserved residues (underlined), while conservative amino acid substitutions may be considered for residues that are neither underlined nor italicized.

```
                                          (SEQ ID NO: 33)
SHIQIPPGLTELLQGYTVEVLRQQPPDLVEFAVEYFTRLREARA
```

The skilled artisan will realize that these and other amino acid substitutions in the antibody moiety or linker portions of the DNL constructs may be utilized to enhance the therapeutic and/or pharmacokinetic properties of the resulting DNL constructs.

Example 7

Antibody-Dendrimer DNL Complex for siRNA

Cationic polymers, such as polylysine, polyethylenimine, or polyamidoamine (PAMAM)-based dendrimers, form complexes with nucleic acids. However, their potential applications as non-viral vectors for delivering therapeutic genes or siRNAs remain a challenge. One approach to improve selectivity and potency of a dendrimeric nanoparticle may be achieved by conjugation with an antibody that internalizes upon binding to target cells.

We synthesized and characterized a novel immunoconjugate, designated E1-G5/2, which was made by the DNL method to comprise half of a generation 5 (G5) PAMAM dendrimer (G5/2) site-specifically linked to a stabilized dimer of Fab derived from hRS7, a humanized antibody that is rapidly internalized upon binding to the Trop-2 antigen expressed on various solid cancers.

Methods

E1-G5/2 was prepared by combining two self-assembling modules, AD2-G5/2 and hRS7-Fab-DDD2, under mild redox conditions, followed by purification on a Protein L column. To make AD2-G5/2, we derivatized the AD2 peptide with a maleimide group to react with the single thiol generated from reducing a G5 PAMAM with a cystamine core and used reversed-phase HPLC to isolate AD2-G5/2. We produced hRS7-Fab-DDD2 as a fusion protein in myeloma cells, as described in the Examples above.

The molecular size, purity and composition of E1-G5/2 were analyzed by size-exclusion HPLC, SDS-PAGE, and Western blotting. The biological functions of E1-G5/2 were assessed by binding to an anti-idiotype antibody against hRS7, a gel retardation assay, and a DNase protection assay.

Results

E1-G5/2 was shown by size-exclusion HPLC to consist of a major peak (>90%) flanked by several minor peaks. The three constituents of E1-G5/2 (Fd-DDD2, the light chain, and AD2-G5/2) were detected by reducing SDS-PAGE and confirmed by Western blotting. Anti-idiotype binding analysis revealed E1-G5/2 contained a population of antibody-dendrimer conjugates of different size, all of which were capable of recognizing the anti-idiotype antibody, thus suggesting structural variability in the size of the purchased G5 dendrimer. Gel retardation assays showed E1-G5/2 was able to maximally condense plasmid DNA at a charge ratio of 6:1 (+/−), with the resulting dendriplexes completely protecting the complexed DNA from degradation by DNase I.

Conclusion

The DNL technique can be used to build dendrimer-based nanoparticles that are targetable with antibodies. Such agents have improved properties as carriers of drugs, plasmids or siRNAs for applications in vitro and in vivo.

Example 8

Maleimide AD2 Conjugate for DNL Dendrimers (SEQ ID NO: 36)

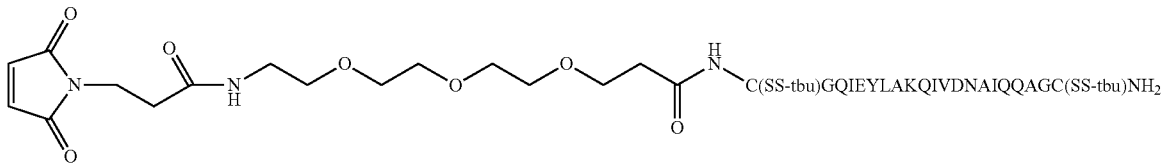

IMP 498

The peptide IMP 498 up to and including the PEG moiety was synthesized on a Protein Technologies PS3 peptide synthesizer by the Fmoc method on Sieber Amide resin (0.1 mmol scale). The maleimide was added manually by mixing the β-maleimidopropionic acid NHS ester with diisopropylethylamine and DMF with the resin for 4 hr. The peptide was cleaved from the resin with 15 mL TFA, 0.5 mL $H_2O$, 0.5 mL triisopropylsilane, and 0.5 mL thioanisole for 3 hr at room temperature. The peptide was purified by reverse phase HPLC using $H_2O/CH_3CN$ TFA buffers to obtain about 90 mg of purified product after lyophilization.

Synthesis of Reduced G5 Dendrimer (G5/2)

The G-5 dendrimer (10% in MeOH, Dendritic Nanotechnologies), 2.03 g, $7.03 \times 10^{-6}$ mol was reduced with 0.1426 TCEP.HCl 1:1 MeOH/$H_2O$ (~4 mL) and stirred overnight at room temperature. The reaction mixture was purified by reverse phase HPLC on a C-18 column eluted with 0.1% TFA $H_2O/CH_3CN$ buffers to obtain 0.0633 g of the desired product after lyophilization.

Synthesis of G5/2 Dendrimer-AD2 Conjugate

The G5/2 Dendrimer, 0.0469 g ($3.35 \times 10^{-6}$ mol) was mixed with 0.0124 g of IMP 498 ($4.4 \times 10^{-6}$ mol) and dissolved in 1:1 MeOH/1M $NaHCO_3$ and mixed for 19 hr at room temperature followed by treatment with 0.0751 g dithiothreitol and 0.0441 g TCEP.HCl. The solution was mixed overnight at room temperature and purified on a C4 reverse phase HPLC column using 0.1% TFA $H_2O/CH_3CN$ buffers to obtain 0.0033 g of material containing the conjugated AD2 and dendrimer as judged by gel electrophoresis and Western blot.

Example 9

Targeted Delivery of siRNA Using Protamine Linked Antibodies

Summary

RNA interference (RNAi) has been shown to down-regulate the expression of various proteins such as HER2, VEGF, Raf-1, bcl-2, EGFR and numerous others in preclinical studies. Despite the potential of RNAi to silence specific genes, the full therapeutic potential of RNAi remains to be realized due to the lack of an effective delivery system to target cells in vivo.

To address this critical need, we developed novel DNL constructs having multiple copies of human protamine tethered to a tumor-targeting, internalizing hRS7 (anti-Trop-2) antibody for targeted delivery of siRNAs in vivo. A DDD2-L-thP1 module comprising truncated human protamine (thP1, residues 8 to 29 of human protamine 1) was produced, in which the sequences of DDD2 and thP1 were fused respectively to the N- and C-terminal ends of a humanized antibody light chain (FIG. 1). The sequence of the truncated hP1 (thP1) is shown below. Reaction of DDD2-L-thP1 with the antibody hRS7-IgG-AD2 under mild redox conditions, as described in the Examples above, resulted in the formation of an E1-L-thP1 complex (FIG. 1), comprising four copies of thP1 attached to the carboxyl termini of the hRS7 heavy chains.

thP1
(SEQ ID NO: 81)
RSQSRSRYYRQRQRSRRRRRRS

The purity and molecular integrity of E1-L-thP1 following Protein A purification were determined by size-exclusion HPLC and SDS-PAGE (not shown). In addition, the ability of E1-L-thP1 to bind plasmid DNA or siRNA was demonstrated by the gel shift assay (FIG. 2). E1-L-thP1 was effective at binding short double-stranded oligonucleotides (FIG. 2) and in protecting bound DNA from digestion by nucleases added to the sample or present in serum (not shown).

Figure 3:
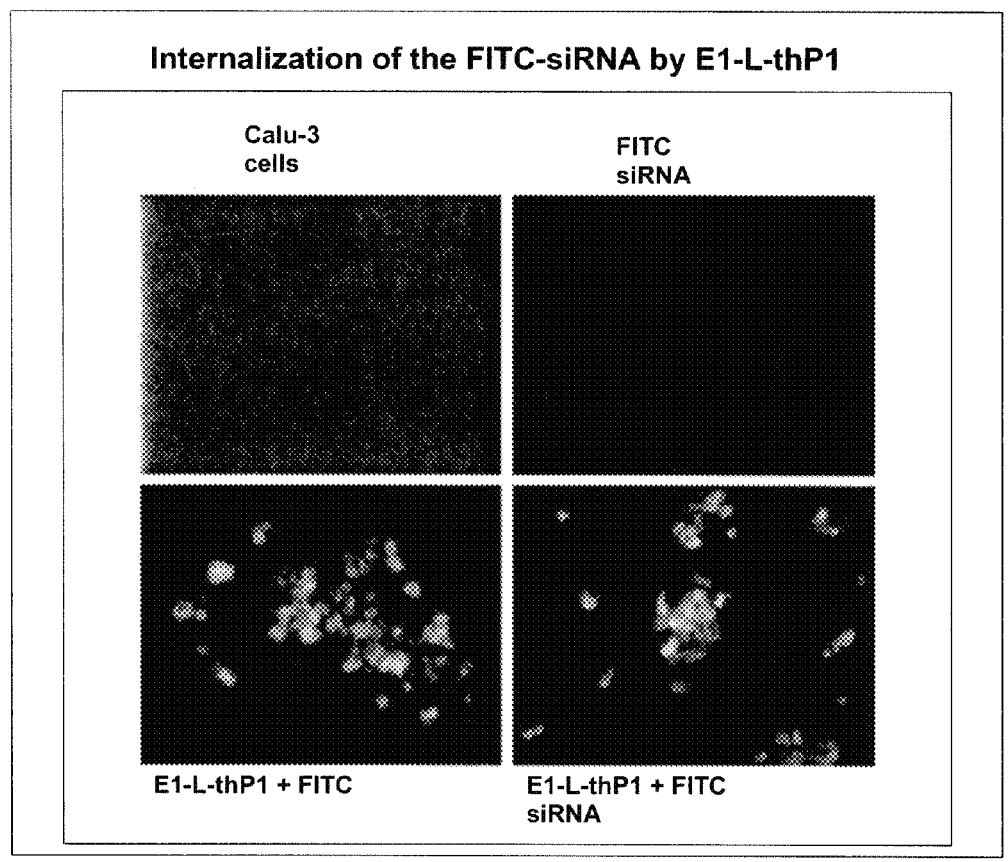
FIG. 3. Internalization of siRNA mediated by E1-L-thP1 binding.

The ability of the E1-L-thP1 construct to internalize siRNAs into Trop-2-expressing cancer cells was confirmed by fluorescence microscopy using FITC-conjugated siRNA and the human Calu-3 lung cancer cell line (FIG. 3).

Methods

The DNL technique was employed to generate E1-L-thP1 (FIG. 1). The hRS7 IgG-AD module (FIG. 1A), constructed as described in the Examples above, was expressed in myeloma cells and purified from the culture supernatant using Protein A affinity chromatography. The DDD2-L-thP1 module (FIG. 1B) was expressed as a fusion protein in myeloma cells and was purified by Protein L affinity chromatography. Since the CH3-AD2-IgG module possesses two AD2 peptides and each can bind to a DDD2 dimer, with each DDD2 monomer attached to a protamine moiety, the resulting E1-L-thP1 conjugate comprises four protamine groups (FIG. 1C). E1-L-thp1 was formed in nearly quantitative yield from the constituent modules and was purified to near homogeneity (not shown) with Protein A.

DDD2-L-thP1 was purified using Protein L affinity chromatography and assessed by size exclusion HPLC analysis and SDS-PAGE under reducing and nonreducing conditions (data not shown). A major peak was observed at 9.6 min (not shown). SDS-PAGE showed a major band between 30 and 40 kDa in reducing gel and a major band about 60 kDa (indicating a dimeric form of DDD2-L-thP1) in nonreducing gel (not shown). The results of Western blotting confirmed the presence of monomeric DDD2-L-tP1 and dimeric DDD2-L-tP1 on probing with anti-DDD antibodies (not shown).

To prepare the E1-L-thP1, hRS7-IgG-AD2 and DDD2-L-thP1 were combined in approximately equal amounts and reduced glutathione (final concentration 1 mM) was added. Following an overnight incubation at room temperature, oxidized glutathione was added (final concentration 2 mM) and the incubation continued for another 24 h. E1-L-thP1 was purified from the reaction mixture by Protein A column chromatography and eluted with 0.1 M sodium citrate buffer (pH 3.5). The product peak was neutralized, concentrated, dialyzed with PBS, filtered, and stored in PBS containing 5% glycerol at 2 to 8° C. The composition of E1-L-thP1 was confirmed by reducing SDS-PAGE (not shown), which showed the presence of all three constituents (AD2-appended heavy chain, DDD2-L-htP1, and light chain).

The ability of DDD2-L-thP1 (not shown) and E1-L-thP1 (FIG. 2) to bind DNA was evaluated by gel shift assay. DDD2-L-thP1 retarded the mobility of 500 ng of a linear form of 3-kb DNA fragment in 1% agarose at a molar ratio of 6 or higher (not shown). FIG. 2 shows that E1-L-thP1 retarded the mobility of 250 ng of a linear 200-bp DNA duplex in 2% agarose at a molar ratio of 4 or higher (FIG. 2, lanes d-g), whereas no such effect was observed for hRS7-IgG-AD2 alone (FIG. 2, lane a). The ability of E1-L-thP1 to protect bound DNA from degradation by exogenous DNase and serum nucleases was also demonstrated (not shown).

The ability of E1-L-thP1 to promote internalization of bound siRNA was examined in the Trop-2 expressing ME-180 cervical cell line (FIG. 3). Internalization of the E1-L-thP1 complex was monitored using FITC conjugated goat anti-human antibodies (FIG. 3, lower left). The cells alone showed no fluorescence (FIG. 3, upper left). Addition of FITC-labeled siRNA alone resulted in minimal internalization of the siRNA (FIG. 3, upper right). Internalization of E1-L-thP1 alone was observed in 60 minutes at 37° C. (FIG. 3, lower left). E1-L-thP1 was able to effectively promote internalization of bound FITC-conjugated siRNA (FIG. 3, lower right). E1-L-thP1 (10 µg) was mixed with FITC-siRNA (300 nM) and allowed to form E1-L-thP1-siRNA complexes which were then added to Trop-2-expressing Calu-3 cells. After incubation for 4 h at 37° C. the cells were checked for internalization of siRNA by fluorescence microscopy (FIG. 3, lower right).

Figure 4:
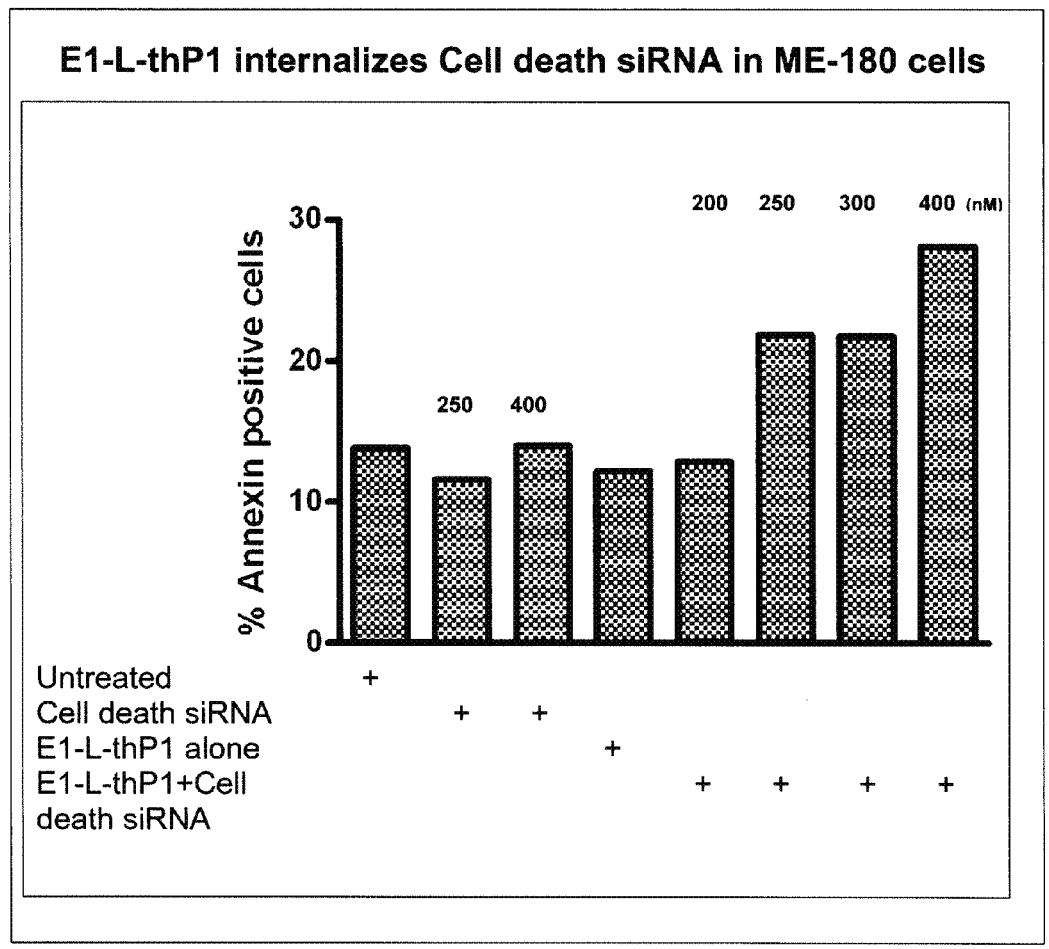
FIG. 4. Apoptosis induced by E1-L-thP1 internalization of siRNA.

The ability of E1-L-thP1 to induce apoptosis by internalization of siRNA was examined (FIG. 4). E1-L-thP1 (10 µg) was mixed with varying amounts of siRNA (AllStars Cell Death siRNA, Qiagen, Valencia, Calif.). The E1-L-thP1-siRNA complex was added to ME-180 cells. After 72 h of incubation, cells were trypsinized and annexin V staining was performed to evaluate apoptosis (FIG. 4). The Cell Death siRNA alone or E1-L-thP1 alone had no effect on apoptosis (FIG. 4). Addition of increasing amounts of E1-L-thP1-siRNA produced a dose-dependent increase in apoptosis (FIG. 4). These results show that E1-L-thP1 could effectively deliver siRNA molecules into the cells and induce apoptosis of target cells.

Conclusions

The DNL technology provides a modular approach to efficiently tether multiple protamine molecules to the anti-Trop-2 hRS7 antibody resulting in the novel molecule E1-L-thP1.

SDS-PAGE demonstrated the homogeneity and purity of E1-L-thP1. DNase protection and gel shift assays showed the DNA binding activity of E1-L-thP1. E1-L-thP1 internalized in the cells like the parental hRS7 antibody and was able to effectively internalize siRNA molecules into Trop-2-expressing cells, such as ME-180 and Calu-3.

The skilled artisan will realize that the DNL technique is not limited to any specific antibody or siRNA species. Rather, the same methods and compositions demonstrated herein can be used to make targeted delivery complexes comprising any antibody, any siRNA carrier and any siRNA species. The use of a bivalent IgG in targeted delivery complexes would result in prolonged circulating half-life and higher binding avidity to target cells, resulting in increased uptake and improved efficacy. This approach to siRNA mediated cell death is particularly appropriate for diseases like pancreatic cancer, where present therapies are ineffective. Pancreatic cancers are known to express CEACAM6 and CD74, both of which are associated with the invasiveness of pancreatic cancer. Suppression of either CD74 or CEACAM6 expression via RNAi has been reported to prevent tumor growth in culture and in experimental animals.

Example 10

Apoptosis of Pancreatic Cancer Using siRNAs Against CD74 and CEACAM6

The siRNAs for CD74 (sc-35023, Santa Cruz Biotechnology, Santa Cruz, Calif.) and CEACAM6 [sense strand 5'-CCGGACAGUUCCAUGUAUAdTdT-3' (SEQ ID NO:82)], are obtained from commercial sources. Sense and antisense siRNAs are dissolved in 30 mM HEPES buffer to a final concentration of 20 µM, heated to 90° C. for 1 min and incubated at 37° C. for 60 min to form duplex siRNA. The duplex siRNA is mixed with E1-L-thP1 and incubated with BxPC-3 (CEACAM6-siRNA) and Capan2 (CD74-siRNA) cells. After 24 h, the changes in the levels of mRNA for the corresponding proteins are determined by real time quantitative PCR analysis. The levels CD74 and CEACAM6 proteins are determined by Western blot analysis and immunohistochemistry. Controls include nonspecific siRNA and the non-targeting DNL complex 20-L-thP1, which contains a humanized anti-CD20 antibody (hA20).

The effects of reduced expression of CD74 and CEACAM6 on the growth of pancreatic cancer cells is determined using the clonogenic assay. About $1\times10^3$ BxPC-3 cells are plated and treated with E1-L-thP1 carrying CEACAM6-siRNA. Media is changed every 3-4 days and after 14 days colonies are fixed with 4% para-formaldehyde solution, stained with 0.5 trypan blue and counted. Similar experiments are performed for Capan2 cells using E1-L-thP1 carrying CD74-siRNA. The effect of E1-L-thP1 carrying both CEACAM6- and CD74-siRNAs on inhibiting the growth of BxPC-3 and Capan2 cells is determined. Cell proliferation by the MTS assay is performed.

Two xenograft models are established in female athymic nu/nu mice (5 weeks of age, weighing 18-20 g). The subcutaneous model has BxPC-3 (ATCC No. CRL-1687) and Capan2 (ATCC No. HTB-80) implanted in opposite flanks of each animal with treatment initiated once tumors reach 50 mm³. The orthotopic model bears only BxPC-3 cells and treatment is started 2 weeks after implantation.

For the subcutaneous model, the efficacy of E1-L-thP1 to deliver a mixture of CEACAM6- and CD74-siRNAs is assessed and compared to that of E1-L-thP1 to deliver CEACAM6-, CD74-, or control siRNA individually. Additional controls are saline and the use of 20-L-thP1 instead of E1-L-thP1 to deliver the specific and control siRNAs. The dosage, schedule, and administration are 150 µg/kg based on siRNA, twice weekly for 6 weeks, and via tail vein injection (Table 4). Cells are expanded in tissue culture, harvested with Trypsin/EDTA, and re-suspended with matrigel (1:1) to deliver 5×10$^6$ cells in 300 µL.

Animals are monitored daily for signs of toxicity and weighed twice weekly. Tumor dimensions are measured weekly and tumor volumes calculated.

The orthotopic model is set up as follows. Briefly, nude mice are anesthetized and a left lateral abdominal incision is made. The spleen and attached pancreas are exteriorized with forceps. Then 50 µL of a BxPC-3 cell suspension (2×10$^6$ cells) is injected into the pancreas. The spleen and pancreas are placed back into the abdominal cavity and the incision closed. Therapy begins two weeks after implantation. Mice are treated systemically with CEACAM6- or control siRNA bound to E1-L-thP1 or 20-L-thP1 with the same dosing schedule and route as the subcutaneous model. Animals are monitored daily and weighed weekly.

TABLE 4

Subcutaneous model with dual tumors

| Group | (N) | Treatment | Dose/Schedule |
|---|---|---|---|
| | | Specific Therapy | |
| 1 | 12 | E1-L-thP1-CEACAM6-siRNA | 150 µg/kg i.v. (twice weekly ×6) |
| 2 | 12 | E1-L-thP1-CD74-siRNA | 150 µg/kg i.v. (twice weekly ×6) |
| 3 | 12 | E1-L-thP1-CEACAM6-siRNA + E1-L-thP1-CD74-siRNA | 150 µg/kg each i.v. (twice weekly ×6) |
| | | Controls | |
| 4 | 12 | Saline | 100 µL i.v. (twice weekly ×6) |
| 5 | 12 | 20-L-thP1-CEACAM6-siRNA | 150 µg/kg i.v. (twice weekly ×6) |
| 6 | 12 | 20-L-thP1-CD74-siRNA | 150 µg/kg i.v. (twice weekly ×6) |
| 7 | 12 | E1-L-thP1-control-siRNA | 150 µg/kg each i.v. (twice weekly ×6) |
| 8 | 12 | 20-L-thP1-control-siRNA | 150 µg/kg each i.v. (twice weekly ×6) |

The results of the study show that both CEACAM6 and CD74 siRNA are internalized into pancreatic cancer cells by the E1-L-thP1 DNL construct and induce apoptosis of pancreatic cancer, while the control DNL construct with non-targeting anti-CD20 antibody is ineffective to induce siRNA uptake or cancer cell death.

It will be apparent to those skilled in the art that various modifications and variations can be made to the products, compositions, methods and processes of this invention. Thus, it is intended that the present invention cover such modifications and variations, provided they come within the scope of the appended claims and their equivalents.

What is claimed is:

1. A complex comprising:
   a) an antibody or antigen-binding fragment thereof attached to one or more anchoring domain (AD) moieties from an AKAP protein; and
   b) one or more siRNA carrier moieties, wherein the siRNA carrier is a human protamine 1, each siRNA carrier attached to a DDD moiety, wherein the amino acid sequence of the DDD moiety is residues 1-44 of human PKA regulatory subunit RIIα, and one or more siRNA attached to the one or more siRNA carrier moieties;

wherein two copies of the DDD moiety form a dimer and bind to the AD moiety to form the complex.

2. The complex of claim 1, wherein the antibody fragment is a F(ab')$_2$, Fab', Fab or scFv antibody fragment.

3. The complex of claim 1, wherein the antibody is a chimeric, humanized or human antibody.

4. A kit comprising the complex according to claim 1.

* * * * *

SEQUENCE LISTING

```
<160> NUMBER OF SEQ ID NOS: 82

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
aatgcggcgg tggtgacagt a                                            21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
aagctcagca cacagaaaga c                                            21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule: Synthetic
      oligonucleotide

<400> SEQUENCE: 3
```

```
uaaaaucuuc ugcccacct t                                         21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 4
ggaagcuguu ggcugaaaat t                                        21

<210> SEQ ID NO 5
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
aagaccagcc ucuuugccca g                                        21

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ggaccaggca gaaaacgag                                           19

<210> SEQ ID NO 7
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
cuaucaggau gacgcgg                                             17

<210> SEQ ID NO 8
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
ugacacaggc aggcuugacu u                                        21

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
```

-continued

<400> SEQUENCE: 9
ggtgaagaag ggcgtccaa                                                       19

<210> SEQ ID NO 10
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gatccgttgg agctgttggc gtagttcaag agactcgcca acagctccaa cttttggaaa         60

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
aggtggtgtt aacagcagag                                                      20

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
aaggtggagc aagcggtgga g                                                    21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
aaggagttga aggccgacaa a                                                    21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 14
uauggagcug cagaggaugu t                                                    21

<210> SEQ ID NO 15
<211> LENGTH: 49
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 15
tttgaatatc tgtgctgaga acacagttct cagcacagat attctttt                         49

<210> SEQ ID NO 16
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
aatgagaaaa gcaaaaggtg ccctgtctc                                              29

<210> SEQ ID NO 17
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
aaucaucauc aagaaagggc a                                                      21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 18
augacuguca ggauguugct t                                                      21

<210> SEQ ID NO 19
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
gaacgaaucc ugaagacauc u                                                      21

<210> SEQ ID NO 20
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
aagcctggct acagcaatat gcctgtctc                                              29

<210> SEQ ID NO 21
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 21
ugaccaucac cgaguuuaut t                                           21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
aagtcggacg caacagagaa a                                           21

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 23
cuaccuuucu acggacgugt t                                           21

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ctgcctaagg cggatttgaa t                                           21

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 25
ttauuccuuc uucgggaagu c                                           21

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 26
aaccttctgg aacccgccca c                                      21

<210> SEQ ID NO 27
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gagcatcttc gagcaagaa                                         19

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
catgtggcac cgtttgcct                                         19

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
aactaccaga aaggtatacc t                                      21

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 30
ucacaguguc cuuuauguat t                                      21

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 31
gcaugaaccg gaggcccaut t                                      21

<210> SEQ ID NO 32
<211> LENGTH: 19
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 32
ccggacagtt ccatgtata                                                      19

<210> SEQ ID NO 33
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 34
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Cys Gly His Ile Gln Ile Pro Pro Gly Leu Thr Glu Leu Leu Gln Gly
1               5                   10                  15

Tyr Thr Val Glu Val Leu Arg Gln Gln Pro Pro Asp Leu Val Glu Phe
            20                  25                  30

Ala Val Glu Tyr Phe Thr Arg Leu Arg Glu Ala Arg Ala
        35                  40                  45

<210> SEQ ID NO 35
<211> LENGTH: 17
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gln Ile Glu Tyr Leu Ala Lys Gln Ile Val Asp Asn Ala Ile Gln Gln
1               5                   10                  15

Ala

<210> SEQ ID NO 36
<211> LENGTH: 21
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Cys Gly Gln Ile Glu Tyr Leu Ala Lys Gln Ile Val Asp Asn Ala Ile
1               5                   10                  15
```

```
Gln Gln Ala Gly Cys
            20

<210> SEQ ID NO 37
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Ser Leu Arg Glu Cys Glu Leu Tyr Val Gln Lys His Asn Ile Gln Ala
1               5                   10                  15

Leu Leu Lys Asp Ser Ile Val Gln Leu Cys Thr Ala Arg Pro Glu Arg
            20                  25                  30

Pro Met Ala Phe Leu Arg Glu Tyr Phe Glu Arg Leu Glu Lys Glu Glu
        35                  40                  45

Ala Lys
    50

<210> SEQ ID NO 38
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Met Ser Cys Gly Gly Ser Leu Arg Glu Cys Glu Leu Tyr Val Gln Lys
1               5                   10                  15

His Asn Ile Gln Ala Leu Leu Lys Asp Ser Ile Val Gln Leu Cys Thr
            20                  25                  30

Ala Arg Pro Glu Arg Pro Met Ala Phe Leu Arg Glu Tyr Phe Glu Arg
        35                  40                  45

Leu Glu Lys Glu Glu Ala Lys
    50                  55

<210> SEQ ID NO 39
<211> LENGTH: 23
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Cys Gly Phe Glu Glu Leu Ala Trp Lys Ile Ala Lys Met Ile Trp Ser
1               5                   10                  15

Asp Val Phe Gln Gln Gly Cys
            20

<210> SEQ ID NO 40
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Gly Ser Gly Gly Gly Gly Ser Gly Gly Gly Gly Ser His Ile Gln Ile
1               5                   10                  15
```

```
Pro Pro Gly Leu Thr Glu Leu Leu Gln Gly Tyr Thr Val Glu Val Leu
            20                  25                  30

Arg Gln Gln Pro Pro Asp Leu Val Glu Phe Ala Val Glu Tyr Phe Thr
            35                  40                  45

Arg Leu Arg Glu Ala Arg Ala
            50                  55

<210> SEQ ID NO 41
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gly Ser Gly Gly Gly Gly Ser Gly Gly Gly Ser Gln Ile Glu Tyr
1               5                   10                  15

Leu Ala Lys Gln Ile Val Asp Asn Ala Ile Gln Gln Ala
            20                  25

<210> SEQ ID NO 42
<211> LENGTH: 51
<212> TYPE: PRT
<213> ORGANISM: Homo sapiens

<400> SEQUENCE: 42

Ser Leu Arg Glu Cys Glu Leu Tyr Val Gln Lys His Asn Ile Gln Ala
1               5                   10                  15

Leu Leu Lys Asp Val Ser Ile Val Gln Leu Cys Thr Ala Arg Pro Glu
            20                  25                  30

Arg Pro Met Ala Phe Leu Arg Glu Tyr Phe Glu Lys Leu Glu Lys Glu
            35                  40                  45

Glu Ala Lys
    50

<210> SEQ ID NO 43
<211> LENGTH: 54
<212> TYPE: PRT
<213> ORGANISM: Homo sapiens

<400> SEQUENCE: 43

Ser Leu Lys Gly Cys Glu Leu Tyr Val Gln Leu His Gly Ile Gln Gln
1               5                   10                  15

Val Leu Lys Asp Cys Ile Val His Leu Cys Ile Ser Lys Pro Glu Arg
            20                  25                  30

Pro Met Lys Phe Leu Arg Glu His Phe Glu Lys Leu Glu Lys Glu Glu
            35                  40                  45

Asn Arg Gln Ile Leu Ala
    50

<210> SEQ ID NO 44
<211> LENGTH: 44
<212> TYPE: PRT
<213> ORGANISM: Homo sapiens

<400> SEQUENCE: 44

Ser His Ile Gln Ile Pro Pro Gly Leu Thr Glu Leu Leu Gln Gly Tyr
1               5                   10                  15

Thr Val Glu Val Gly Gln Gln Pro Pro Asp Leu Val Asp Phe Ala Val
```

```
                    20                  25                  30

Glu Tyr Phe Thr Arg Leu Arg Glu Ala Arg Arg Gln
            35                  40

<210> SEQ ID NO 45
<211> LENGTH: 44
<212> TYPE: PRT
<213> ORGANISM: Homo sapiens

<400> SEQUENCE: 45

Ser Ile Glu Ile Pro Ala Gly Leu Thr Glu Leu Leu Gln Gly Phe Thr
1               5                   10                  15

Val Glu Val Leu Arg His Gln Pro Ala Asp Leu Leu Glu Phe Ala Leu
            20                  25                  30

Gln His Phe Thr Arg Leu Gln Gln Glu Asn Glu Arg
            35                  40

<210> SEQ ID NO 46
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gln Ile Glu Tyr Val Ala Lys Gln Ile Val Asp Tyr Ala Ile His Gln
1               5                   10                  15

Ala

<210> SEQ ID NO 47
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gln Ile Glu Tyr Lys Ala Lys Gln Ile Val Asp His Ala Ile His Gln
1               5                   10                  15

Ala

<210> SEQ ID NO 48
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gln Ile Glu Tyr His Ala Lys Gln Ile Val Asp His Ala Ile His Gln
1               5                   10                  15

Ala

<210> SEQ ID NO 49
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 49

Gln Ile Glu Tyr Val Ala Lys Gln Ile Val Asp His Ala Ile His Gln
1               5                   10                  15

Ala

<210> SEQ ID NO 50
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Pro Leu Glu Tyr Gln Ala Gly Leu Leu Val Gln Asn Ala Ile Gln Gln
1               5                   10                  15

Ala Ile

<210> SEQ ID NO 51
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Leu Leu Ile Glu Thr Ala Ser Ser Leu Val Lys Asn Ala Ile Gln Leu
1               5                   10                  15

Ser Ile

<210> SEQ ID NO 52
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Leu Ile Glu Glu Ala Ala Ser Arg Ile Val Asp Ala Val Ile Glu Gln
1               5                   10                  15

Val Lys

<210> SEQ ID NO 53
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ala Leu Tyr Gln Phe Ala Asp Arg Phe Ser Glu Leu Val Ile Ser Glu
1               5                   10                  15

Ala Leu

<210> SEQ ID NO 54
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 54

Leu Glu Gln Val Ala Asn Gln Leu Ala Asp Gln Ile Ile Lys Glu Ala
1               5                   10                  15

Thr

<210> SEQ ID NO 55
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Phe Glu Glu Leu Ala Trp Lys Ile Ala Lys Met Ile Trp Ser Asp Val
1               5                   10                  15

Phe

<210> SEQ ID NO 56
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Glu Leu Val Arg Leu Ser Lys Arg Leu Val Glu Asn Ala Val Leu Lys
1               5                   10                  15

Ala Val

<210> SEQ ID NO 57
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Thr Ala Glu Glu Val Ser Ala Arg Ile Val Gln Val Val Thr Ala Glu
1               5                   10                  15

Ala Val

<210> SEQ ID NO 58
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gln Ile Lys Gln Ala Ala Phe Gln Leu Ile Ser Gln Val Ile Leu Glu
1               5                   10                  15

Ala Thr

<210> SEQ ID NO 59
<211> LENGTH: 16
<212> TYPE: PRT
<213> ORGANISM: Artificial Sequence
<220> FEATURE:
<223> OTHER INFORMATION: Description of Artificial Sequence: Synthetic
```

```
                            peptide

<400> SEQUENCE: 59

Leu Ala Trp Lys Ile Ala Lys Met Ile Val Ser Asp Val Met Gln Gln
1               5                   10                  15

<210> SEQ ID NO 60
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Asp Leu Ile Glu Glu Ala Ala Ser Arg Ile Val Asp Ala Val Ile Glu
1               5                   10                  15

Gln Val Lys Ala Ala Gly Ala Tyr
            20

<210> SEQ ID NO 61
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Leu Glu Gln Tyr Ala Asn Gln Leu Ala Asp Gln Ile Ile Lys Glu Ala
1               5                   10                  15

Thr Glu

<210> SEQ ID NO 62
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Phe Glu Glu Leu Ala Trp Lys Ile Ala Lys Met Ile Trp Ser Asp Val
1               5                   10                  15

Phe Gln Gln Cys
            20

<210> SEQ ID NO 63
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gln Ile Glu Tyr Leu Ala Lys Gln Ile Pro Asp Asn Ala Ile Gln Gln
1               5                   10                  15

Ala

<210> SEQ ID NO 64
<211> LENGTH: 25
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 64

Lys Gly Ala Asp Leu Ile Glu Glu Ala Ala Ser Arg Ile Val Asp Ala
1               5                   10                  15

Val Ile Glu Gln Val Lys Ala Ala Gly
            20                  25

<210> SEQ ID NO 65
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Lys Gly Ala Asp Leu Ile Glu Glu Ala Ala Ser Arg Ile Pro Asp Ala
1               5                   10                  15

Pro Ile Glu Gln Val Lys Ala Ala Gly
            20                  25

<210> SEQ ID NO 66
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Pro Glu Asp Ala Glu Leu Val Arg Leu Ser Lys Arg Leu Val Glu Asn
1               5                   10                  15

Ala Val Leu Lys Ala Val Gln Gln Tyr
            20                  25

<210> SEQ ID NO 67
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Pro Glu Asp Ala Glu Leu Val Arg Thr Ser Lys Arg Leu Val Glu Asn
1               5                   10                  15

Ala Val Leu Lys Ala Val Gln Gln Tyr
            20                  25

<210> SEQ ID NO 68
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Pro Glu Asp Ala Glu Leu Val Arg Leu Ser Lys Arg Asp Val Glu Asn
1               5                   10                  15

Ala Val Leu Lys Ala Val Gln Gln Tyr
            20                  25
```

<210> SEQ ID NO 69
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Pro Glu Asp Ala Glu Leu Val Arg Leu Ser Lys Arg Leu Pro Glu Asn
1               5                   10                  15

Ala Val Leu Lys Ala Val Gln Gln Tyr
            20                  25

<210> SEQ ID NO 70
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Pro Glu Asp Ala Glu Leu Val Arg Leu Ser Lys Arg Leu Pro Glu Asn
1               5                   10                  15

Ala Pro Leu Lys Ala Val Gln Gln Tyr
            20                  25

<210> SEQ ID NO 71
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Pro Glu Asp Ala Glu Leu Val Arg Leu Ser Lys Arg Leu Val Glu Asn
1               5                   10                  15

Ala Val Glu Lys Ala Val Gln Gln Tyr
            20                  25

<210> SEQ ID NO 72
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Glu Glu Gly Leu Asp Arg Asn Glu Glu Ile Lys Arg Ala Ala Phe Gln
1               5                   10                  15

Ile Ile Ser Gln Val Ile Ser Glu Ala
            20                  25

<210> SEQ ID NO 73
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

-continued

Leu Val Asp Asp Pro Leu Glu Tyr Gln Ala Gly Leu Leu Val Gln Asn
1               5                   10                  15

Ala Ile Gln Gln Ala Ile Ala Glu Gln
            20                  25

<210> SEQ ID NO 74
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gln Tyr Glu Thr Leu Leu Ile Glu Thr Ala Ser Ser Leu Val Lys Asn
1               5                   10                  15

Ala Ile Gln Leu Ser Ile Glu Gln Leu
            20                  25

<210> SEQ ID NO 75
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Leu Glu Lys Gln Tyr Gln Glu Gln Leu Glu Glu Val Ala Lys Val
1               5                   10                  15

Ile Val Ser Met Ser Ile Ala Phe Ala
            20                  25

<210> SEQ ID NO 76
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Asn Thr Asp Glu Ala Gln Glu Glu Leu Ala Trp Lys Ile Ala Lys Met
1               5                   10                  15

Ile Val Ser Asp Ile Met Gln Gln Ala
            20                  25

<210> SEQ ID NO 77
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Val Asn Leu Asp Lys Lys Ala Val Leu Ala Glu Lys Ile Val Ala Glu
1               5                   10                  15

Ala Ile Glu Lys Ala Glu Arg Glu Leu
            20                  25

<210> SEQ ID NO 78
<211> LENGTH: 25
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 78

Asn Gly Ile Leu Glu Leu Glu Thr Lys Ser Ser Lys Leu Val Gln Asn
1               5                   10                  15

Ile Ile Gln Thr Ala Val Asp Gln Phe
            20                  25

<210> SEQ ID NO 79
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Thr Gln Asp Lys Asn Tyr Glu Asp Glu Leu Thr Gln Val Ala Leu Ala
1               5                   10                  15

Leu Val Glu Asp Val Ile Asn Tyr Ala
            20                  25

<210> SEQ ID NO 80
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Glu Thr Ser Ala Lys Asp Asn Ile Asn Ile Glu Glu Ala Ala Arg Phe
1               5                   10                  15

Leu Val Glu Lys Ile Leu Val Asn His
            20                  25

<210> SEQ ID NO 81
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Arg Ser Gln Ser Arg Ser Arg Tyr Tyr Arg Gln Arg Gln Arg Ser Arg
1               5                   10                  15

Arg Arg Arg Arg Arg Ser
            20

<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 82
ccggacaguu ccauguauat t                                          21
```